United States Patent
Jin et al.

(10) Patent No.: US 10,570,185 B2
(45) Date of Patent: Feb. 25, 2020

(54) METHOD TO DETECT AUTOANTIBODY REACTIVITY FOR DEAMIDATED INSULIN AUTOANTIGEN IN DIABETES

(71) Applicant: Northwestern University, Evanston, IL (US)

(72) Inventors: Jing Jin, Hinsdale, IL (US); Xunrong Luo, Chicago, IL (US); Grazia Aleppo, Chicago, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 230 days.

(21) Appl. No.: 15/152,093

(22) Filed: May 11, 2016

(65) Prior Publication Data
US 2016/0355564 A1    Dec. 8, 2016

Related U.S. Application Data

(60) Provisional application No. 62/159,755, filed on May 11, 2015.

(51) Int. Cl.
| | | |
|---|---|---|
| C07K 14/26 | (2006.01) | |
| C07K 14/62 | (2006.01) | |
| C07K 16/26 | (2006.01) | |
| G01N 33/74 | (2006.01) | |
| G01N 33/68 | (2006.01) | |
| A61K 38/00 | (2006.01) | |

(52) U.S. Cl.
CPC .............. *C07K 14/62* (2013.01); *C07K 16/26* (2013.01); *G01N 33/6893* (2013.01); *G01N 33/74* (2013.01); *A61K 38/00* (2013.01); *C07K 2317/34* (2013.01); *G01N 2333/62* (2013.01); *G01N 2440/16* (2013.01); *G01N 2800/042* (2013.01); *G01N 2800/50* (2013.01)

(58) Field of Classification Search
None
See application file for complete search history.

(56) References Cited

U.S. PATENT DOCUMENTS

2017/0045529 A1 * 2/2017 Anderson ............ G01N 33/564

FOREIGN PATENT DOCUMENTS

WO    WO 2001077342       10/2001
WO    WO-2015006833 A1 *  1/2015 ............. A61K 38/28

OTHER PUBLICATIONS

Melani, F., et al. PNAS 1970;67(1):148-155.*
Allmendinger et al., Fluoroolefin dipeptide isosteres—I.: The synthesis of Glyψ CF=CH)Gly and racemic Pheψy(CF=CH)Gly, Tetrahedron Lett., 1990, 31:7297-7300.
Boerner et al., Production of antigen-specific human monoclonal antibodies from in vitro-primed human splenocytes, J. Immunol., 1991, 147:86-95.
Brennan et al.,Preparation of bispecific antibodies by chemical recombination of monoclonal immunoglobulin G1 fragments, Science, 1985, 229:81-83.
Chorev et al., A dozen years of retro-inverso peptidomimetics, Acc. Chem. Res, 1993, 26:266-273.
Clackson et al., Making antibody fragments using phage display libraries, Nature, 1991, 352:624-628.
Cole et al., The EBV-Hybridoma Technique and Its Application to Human Lung Cancer, Monoclonal Antibodies and Cancer Therapy, Alan R. Liss Inc., 1985, pp. 77-96.
Gombotz et al., Biodegradable polymers for protein and peptide drug delivery, Bioconjug Chem. Jul.-Aug. 1995;6(4):332-51.
Gruber et al., Efficient tumor cell lysis mediated by a bispecific single chain antibody expressed in *Escherichia coli*, J. Immunol., 1994, 152:5368-5374.
Hoffman et al., The Stereoselective Synthesis of 2-Alkyl .gamma.-Keto Acid and Heterocyclic Ketomethylene Peptide Isostere Core Units Using Chiral Alkylation by 2-Triflyloxy Esters, J. Org. Chem., 1995, 60:5107-5113.
Hoogenboom et al., By-passing immunisation. Human antibodies from synthetic repertoires of germline VH gene segments rearranged in vitro, J. Mol. Biol., 1991, 227:381-388.
Hudson et al., Engineered antibodies, Nat Med. Jan. 2003;9(1):129-34.
Jones et al., Replacing the complementarity-determining regions in a human antibody with those from a mouse, Nature, 1986, 321:522-525.
Kohler et al., Continuous cultures of fused cells secreting antibody of predefined specificity, Nature, 1975, 256:495-497.
Kostelny et al., Formation of a bispecific antibody by the use of leucine zippers, J. Immunol., 1992, 148:1547-1553.
Lavielle et al., Importance of the leucine side-chain to the spasmogenic activity and binding of substance P analogues, Int J Pept Protein Res. Sep. 1993;42(3):270-7.
Luisi et al., Ψ(SO₂-NH) transition state isosteres of peptides. Synthesis of the glutathione disulfide analogue, Tetrahedron Lett. 1993, 34:2391-2392.
Luthman et al., Peptides and Petidomimetics, in Drug Design and Development, Chapter 14, Krogsgaard-Larsen, Liljefors and Madsen (Eds) 1996, Horwood Acad. pp. 386-406.
Marks et al., By-passing immunization. Human antibodies from V-gene libraries displayed on phage, J. Mol. Biol., 1991, 222:581-597.
McCafferty et al., Phage antibodies: filamentous phage displaying antibody variable domains, Nature, 1990, 348:552-554.
Millstein et al., Hybrid hybridomas and their use in immunohistochemistry, Nature, 1983, 305:537-539.

(Continued)

*Primary Examiner* — G. R. Ewoldt
(74) *Attorney, Agent, or Firm* — Benesch, Friedlander, Coplan & Aronoff LLP

(57) ABSTRACT

Provided herein are epitopes and mimotopes thereof useful in the diagnosis and treatment of type 1 diabetes (T1D), as well as antibodies recognizing such epitopes, and diagnostics, therapeutics, kits, and methods of use thereof.

5 Claims, 22 Drawing Sheets

Specification includes a Sequence Listing.

(56) References Cited

OTHER PUBLICATIONS

Ostresh et al., "Libraries from libraries": chemical transformation of combinatorial libraries to extend the range and repertoire of chemical diversity, Proc Natl Acad Sci U S A. Nov. 8, 1994;91(23):11138-42.
Reichmann et al., Reshaping human antibodies for therapy, Nature, 1988, 332:323-327.
Sasaki et al., Protection of ψ(CH2NH) Peptide Bond with 2, 4-Dimethoxybenzyl Group in Solid-Phase Peptide Synthesis, J. Chem. Pharm. Bull., 1997, 45:13-17.
Schmidt et al., Structure-activity relationships of dermorphin analogues containing N-substituted amino acids in the 2-position of the peptide sequence, Int J Pept Protein Res. Jul. 1995;46(1):47-55.
Shalaby et al., Development of humanized bispecific antibodies reactive with cytotoxic lymphocytes and tumor cells overexpressing the HER2 protooncogene, J. Exp. Med., 1992, 175:217-225.
Sheets et al., Efficient construction of a large nonimmune phage antibody library: the production of high-affinity human single-chain antibodies to protein antigens, PNAS, 1998, 95:6157-6162.
Sherman et al. , Compatibility of thioamides with reverse turn features: synthesis and conformational analysis of two model cyclic pseudopeptides containing thioamides as backbone modifications, J. Am. Chem. Soc., 1990, 112:433-441.
Spatola, Synthesis of Pseudopeptides, Methods Neurosci, 1993, 13:19-42.
Suresh et al, Bispecific monoclonal antibodies from hybrid hybridomas, Methods in Enzymol., 1986, 121:210-228.
Traunecker et al., Bispecific single chain molecules (Janusins) target cytotoxic lymphocytes on HIV infected cells, EMBO J., 1991, 10:3655-3659.
Vaughan et al., Human antibodies with sub-nanomolar affinities isolated from a large non-immunized phage display library, Nature Biotechnology, 1996, 14:309-314.
Verhoeyen et al., Reshaping human antibodies: grafting an antilysozyme activity, Science, 1988, 239:1534-1536.

\* cited by examiner

)1 GPGAGSLEPL- Deamidated (E) proinsulin epitope (Quary)
: 92 PGAGAVEP-- Human herpesvirus 4 strain GD1 (EBV)*
: 93 PGACALEP-- Human herpesvirus 5 strain TR-BAC*
): 94 PGAGAPEP-- Cercopithecine herpesvirus 8 strain*
: 95 PGAGGPEP-- Cercopithecine herpesvirus 2 strain SA8*
)6 GAGAGEGEPL- Equine herpesvirus 2 strain 86 67*

*Putative viral envelope protein of glycoprotein G

FIG. 22

| Animal ID | Clone ID | Specificity | V_H Gene | V_L Gene |
|---|---|---|---|---|
| #29 | 11D10 | Dm-Ins2 | IGHV4-1 | IGKV3-12 |
| #27 | 6E6 | Dm-Ins2 | IGHV1-53 | IGKV8-28 |
| #2 | 5B8 | Dm-Ins2 | IGHV1-53 | IGKV8-28 |
| #11 | 8G9 | Dm-Ins2 | IGHV1-53 | IGKV8-28 |
| #9 | 6G9 | Dm-Ins1/2 | IGHV2-2 | IGKV8-28 |
| #27 | 10F8 | Dm-Ins1/2 | IGHV2-2 | IGKV1-110 |
| #27 | 5G7 | Dm-Ins1/2 | IGHV2-2 | IGKV1-110 |
| #27 | 5F7 | Dm-Ins1/2 | IGHV2-2 | IGKV1-110 |
| #27 | 6E9 | Dm-Ins1/2 | IGHV2-2 | IGKV1-132 |
| #27 | 6F6 | Dm-Ins2 | IGHV4-2 | IGKV1-110 |

| | | | | | | | | | |
|---|---|---|---|---|---|---|---|---|---|
| 10F8 | F | Q | G | T | H | V | P | Y | A | : 97
| 5G7 | F | Q | G | T | H | V | P | Y | T | : 98
| 5F7 | F | Q | G | T | H | V | P | R | A | : 99

METHOD TO DETECT AUTOANTIBODY REACTIVITY FOR DEAMIDATED INSULIN AUTOANTIGEN IN DIABETES

CROSS-REFERENCE TO RELATED APPLICATIONS

The present application claims the priority benefit of U.S. Provisional Patent Application 62/159,755, filed May 11, 2015, which is incorporated by reference in its entirety.

FIELD

Provided herein are epitopes and mimotopes thereof useful in the diagnosis and treatment of type 1 diabetes (T1D), as well as antibodies recognizing such epitopes, and diagnostics, therapeutics, kits, and methods of use thereof.

BACKGROUND

In Type 1 diabetes (T1D, insulin-dependent diabetes, or juvenile diabetes), the immune system mounts a misguided destruction of insulin-producing islet cells. Thus T1D is classified as an autoimmune disorder, where the immune system fails to recognize certain cells of the body as "self" Type 1 diabetes (T1D) is characterized by a progressive loss of functional pancreatic beta cell mass triggered by cell directed autoimmunity (FIG. 1). Insulin is the primary autoantigen in T1D, and the strongest susceptibility locus IDDM1 encodes MHC-II receptors on antigen presenting cells.

SUMMARY

Provided herein are epitopes and mimotopes thereof useful in the diagnosis and treatment of type 1 diabetes (T1D), as well as antibodies recognizing such epitopes, and diagnostics, therapeutics, kits, and methods of use thereof.

In some embodiments, provided herein are compositions comprising a peptide or polypeptide comprising at least 70% (e.g., 70%, 75%, 80%, 85%, 90%, 95%, or more, more ranges therebetween) sequence identity to a sequence of one of SEQ ID Nos: 101-111. In some embodiments, provided herein are compositions comprising a peptide or polypeptide comprising at least 70% (e.g., 70%, 75%, 80%, 85%, 90%, 95%, or more, more ranges therebetween) sequence similarity (e.g., conservative or semi-conservative) to a sequence of one of SEQ ID NOs: 101-111. In some embodiments, the peptide or polypeptide comprises at least one Q to E substitution relative to SEQ ID NO: 2. In some embodiments, the peptide or polypeptide is pharmaceutically-formulated for administration to a subject for the treatment or prevention of type 1 diabetes. In some embodiments, peptide or polypeptide further comprises a detectable label. In some embodiments, the peptide or polypeptide is attached to a solid surface (e.g., plate, chip, bead, resin, etc.).

In some embodiments, provided herein are methods comprising administering a peptide or polypeptide comprising a deamidated insulin-based sequence to a subject for the treatment or prevention of type 1 diabetes. In some embodiments, provided herein is the use of a peptide or polypeptide comprising a deamidated insulin-based sequence to induce immune tolerance against diabetogenic autoimmunity in a subject. In some embodiments, the subject is at risk of developing type 1 diabetes (e.g., but does not yet suffer from diabetes or symptoms thereof).

In some embodiments, provided herein are methods of diagnosing a subject as having type 1 diabetes or of being at increased risk for developing type 1 diabetes comprising contacting a peptide or polypeptide comprising a deamidated insulin-based sequence with a sample from the subject, and detecting the presence of antibodies in the sample that bind to the peptide or polypeptide.

In some embodiments, provided herein are compositions comprising an antibody or antibody fragment that selectively binds to a deamidated insulin sequence having a portion with at least 70% (e.g., 70%, 75%, 80%, 85%, 90%, 95%, or more, more ranges therebetween) sequence identity to a sequence of one of SEQ ID Nos: 101-111. In some embodiments, provided herein are compositions comprising an antibody or antibody fragment that selectively binds to a deamidated insulin sequence having a portion with at least 70% (e.g., 70%, 75%, 80%, 85%, 90%, 95%, or more, more ranges therebetween) sequence similarity (e.g., conservative, semi-conservative, etc.) to a sequence of one of SEQ ID Nos: 101-111. In some embodiments, the antibody or antibody fragment further comprises a detectable label. In some embodiments, the antibody or antibody fragment is attached to a solid surface.

In some embodiments, provided herein are methods comprising administering an antibody or antibody fragment described herein to a subject for the treatment or prevention of type 1 diabetes.

In some embodiments, provided herein are methods of diagnosing a subject as having type 1 diabetes or of being at increased risk for developing type 1 diabetes comprising contacting an antibody or antibody fragment described herein with a sample (e.g., blood, plasma, serum, cells, etc.) from the subject, and detecting the presence of deamidated insulin in the sample.

In some embodiments, provided herein are methods of treating or preventing type 1 diabetes in a subject comprising interfering with the deamidation of at least one glutamine residue in a pro-insulin of the subject. In some embodiments, the at least one glutamine residue is a C-peptide glutamine.

In some embodiments, provided herein are methods of treating or preventing type 1 diabetes in a subject comprising interfering with the recognition of deamidated pro-insulin by autoantibodies of the subject.

These embodiments and other embodiments within the scope herein are described in greater detail in the Detailed Description.

BRIEF DESCRIPTION OF THE DRAWINGS

FIG. 22 shows a table demonstrating that antibody gene type matches antigen specificity.

DEFINITIONS

Figure 1:
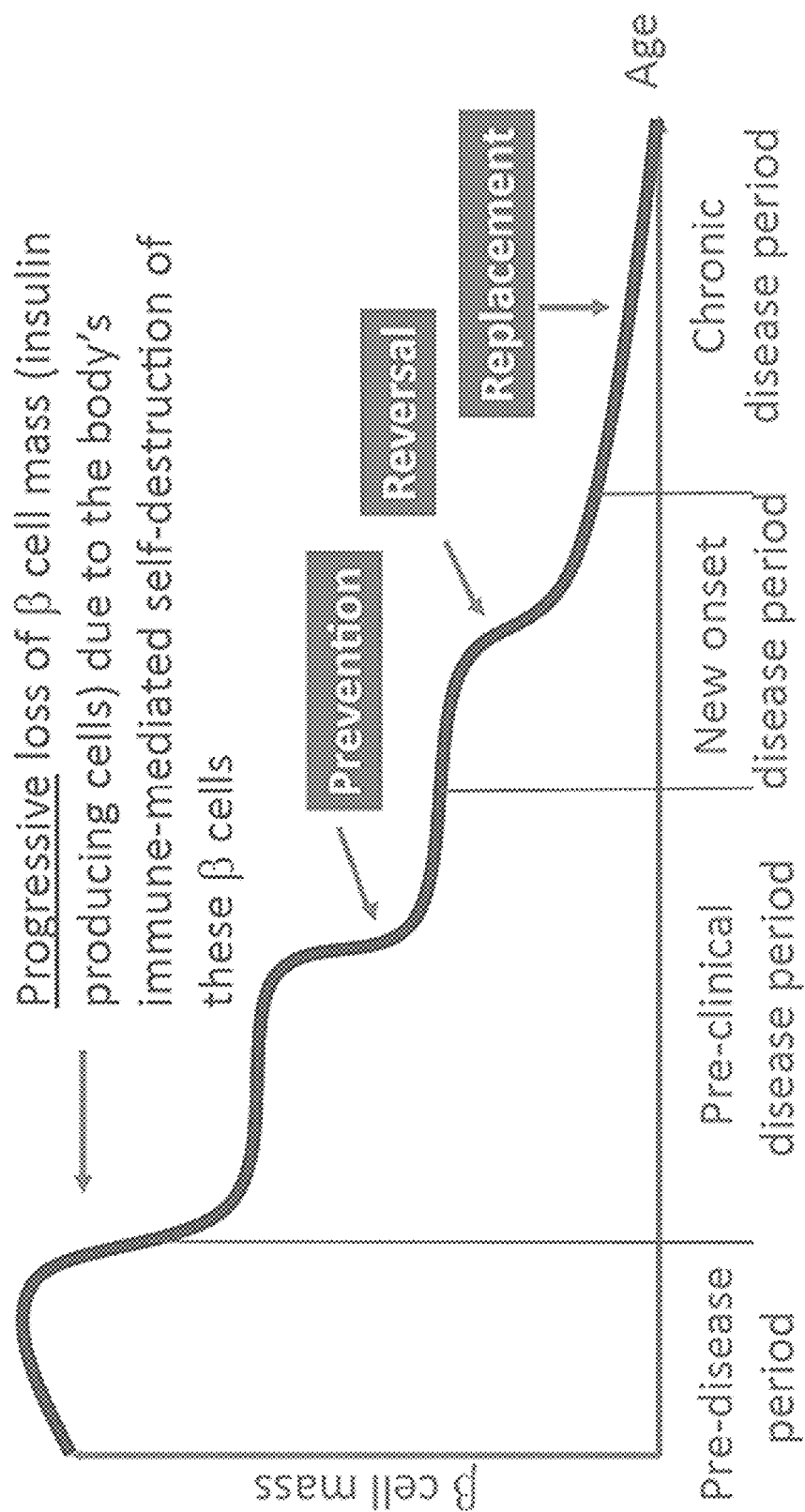
FIG. 1 depicts progressive β cell loss during the course of T1D pathogenesis.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a deamidated insulin mimotope" is a reference to one or more deamidated insulin mimotopes and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition.

As used herein, the term "sample" is used in its broadest sense. In one sense, it is meant to include a specimen or culture obtained from any source, as well as biological samples. Biological samples may be obtained from animals (including humans) and encompass fluids, solids, tissues, and gases. Biological samples include blood products, such as plasma, serum and the like. Sample may also refer to cell lysates or purified forms of the peptides and/or polypeptides described herein. Cell lysates may include cells that have been lysed with a lysing agent or lysates such as rabbit reticulocyte or wheat germ lysates. Sample may also include cell-free expression systems. Such examples are not however to be construed as limiting the sample types applicable to the present invention.

As used herein, the term "antibody" refers to a whole antibody molecule or a fragment thereof (e.g., fragments such as Fab, Fab', and F(ab')$_2$), it may be a polyclonal or monoclonal antibody, a chimeric antibody, a humanized antibody, a human antibody, etc.

A native antibody typically has a tetrameric structure. A tetramer typically comprises two identical pairs of polypeptide chains, each pair having one light chain (in certain embodiments, about 25 kDa) and one heavy chain (in certain embodiments, about 50-70 kDa). In a native antibody, a heavy chain comprises a variable region, $V_H$, and three constant regions, $C_{H1}$, $C_{H2}$, and $C_{H3}$. The $V_H$ domain is at the amino-terminus of the heavy chain, and the $C_{H3}$ domain is at the carboxy-terminus. In a native antibody, a light chain comprises a variable region, $V_L$, and a constant region, $C_L$. The variable region of the light chain is at the amino-terminus of the light chain. In a native antibody, the variable regions of each light/heavy chain pair typically form the antigen binding site. The constant regions are typically responsible for effector function.

In a native antibody, the variable regions typically exhibit the same general structure in which relatively conserved framework regions (FRs) are joined by three hypervariable regions, also called complementarity determining regions (CDRs). The CDRs from the two chains of each pair typically are aligned by the framework regions, which may enable binding to a specific epitope. From N-terminus to C-terminus, both light and heavy chain variable regions typically comprise the domains FR1, CDR1, FR2, CDR2, FR3, CDR3 and FR4. The CDRs on the heavy chain are referred to as H1, H2, and H3, while the CDRs on the light chain are referred to as L1, L2, and L3. Typically, CDR3 is the greatest source of molecular diversity within the antigen-binding site. H3, for example, in certain instances, can be as short as two amino acid residues or greater than 26. The assignment of amino acids to each domain is typically in accordance with the definitions of Kabat et al. (1991) Sequences of Proteins of Immunological Interest (National Institutes of Health, Publication No. 91-3242, vols. 1-3, Bethesda, Md.); Chothia, C., and Lesk, A. M. (1987) J. Mol. Biol. 196:901-917; or Chothia, C. et al. Nature 342:878-883 (1989). In the present application, the term "CDR" refers to a CDR from either the light or heavy chain, unless otherwise specified.

As used herein, the term "heavy chain" refers to a polypeptide comprising sufficient heavy chain variable region sequence to confer antigen specificity either alone or in combination with a light chain.

As used herein, the term "light chain" refers to a polypeptide comprising sufficient light chain variable region sequence to confer antigen specificity either alone or in combination with a heavy chain.

As used herein, when an antibody or other entity "specifically recognizes" or "specifically binds" an antigen or epitope, it preferentially recognizes the antigen in a complex mixture of proteins and/or macromolecules, and binds the antigen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant ($K_a$) of at least $10^7$ $M^{-1}$ (e.g., $>10^7$ $M^{-1}$, $>10^8$ $M^{-1}$, $>10^9$ $M^{-1}$, $>10^{10}$ $M^{-1}$, $>10^{11}M^{-1}$, $>10^{12}$ $M^{-1}$, $>10^{13}$ $M^{-1}$, etc.). In certain such embodiments, an antibody is capable of binding different antigens so long as the different antigens comprise that particular epitope. In certain instances, for example, homologous proteins from different species may comprise the same epitope.

As used herein, the term "monoclonal antibody" refers to an antibody which is a member of a substantially homogeneous population of antibodies that specifically bind to the same epitope. In certain embodiments, a monoclonal antibody is secreted by a hybridoma. In certain such embodiments, a hybridoma is produced according to certain methods known to those skilled in the art. See, e.g., Kohler and Milstein (1975) Nature 256: 495-499; herein incorporated by reference in its entirety. In certain embodiments, a monoclonal antibody is produced using recombinant DNA methods (see, e.g., U.S. Pat. No. 4,816,567). In certain embodiments, a monoclonal antibody refers to an antibody fragment isolated from a phage display library. See, e.g., Clackson et al. (1991) Nature 352: 624-628; and Marks et al. (1991) J. Mol. Biol. 222: 581-597; herein incorporated by reference in their entireties. The modifying word "monoclonal" indicates properties of antibodies obtained from a substantially-homogeneous population of antibodies, and does not limit a method of producing antibodies to a specific method. For various other monoclonal antibody production techniques, see, e.g., Harlow and Lane (1988) Antibodies: A Laboratory Manual (Cold Spring Harbor Laboratory, Cold Spring Harbor, N.Y.); herein incorporated by reference in its entirety.

As used herein, the term "antibody fragment" refers to a portion of a full-length antibody, including at least a portion antigen binding region or a variable region. Antibody fragments include, but are not limited to, Fab, Fab', F(ab')$_2$, Fv, scFv, Fd, diabodies, and other antibody fragments that retain at least a portion of the variable region of an intact antibody. See, e.g., Hudson et al. (2003) Nat. Med. 9:129-134; herein incorporated by reference in its entirety. In certain embodiments, antibody fragments are produced by enzymatic or chemical cleavage of intact antibodies (e.g., papain digestion and pepsin digestion of antibody) produced by recombinant DNA techniques, or chemical polypeptide synthesis.

For example, a "Fab" fragment comprises one light chain and the $C_{H1}$ and variable region of one heavy chain. The heavy chain of a Fab molecule cannot form a disulfide bond with another heavy chain molecule. A "Fab'" fragment comprises one light chain and one heavy chain that comprises additional constant region, extending between the $C_{H1}$ and $C_{H2}$ domains. An interchain disulfide bond can be formed between two heavy chains of a Fab' fragment to form a "F(ab)$_2$" molecule.

An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946,778 and 5,260,203; herein incorporated by reference in their entireties. In certain instances, a single variable region (e.g., a heavy chain variable region or a light chain variable region) may have the ability to recognize and bind antigen.

Other antibody fragments will be understood by skilled artisans.

As used herein, the term "chimeric antibody" refers to an antibody made up of components from at least two different sources. In certain embodiments, a chimeric antibody comprises a portion of an antibody derived from a first species fused to another molecule, e.g., a portion of an antibody derived from a second species. In certain such embodiments, a chimeric antibody comprises a portion of an antibody derived from a non-human animal fused to a portion of an antibody derived from a human. In certain such embodiments, a chimeric antibody comprises all or a portion of a variable region of an antibody derived from a non-human animal fused to a constant region of an antibody derived from a human.

A "humanized" antibody refers to a non-human antibody that has been modified so that it more closely matches (in amino acid sequence) a human antibody. A humanized antibody is thus a type of chimeric antibody. In certain embodiments, amino acid residues outside of the antigen binding residues of the variable region of the non-human antibody are modified. In certain embodiments, a humanized antibody is constructed by replacing all or a portion of a complementarity determining region (CDR) of a human antibody with all or a portion of a CDR from another antibody, such as a non-human antibody, having the desired antigen binding specificity. In certain embodiments, a humanized antibody comprises variable regions in which all or substantially all of the CDRs correspond to CDRs of a non-human antibody and all or substantially all of the framework regions (FRs) correspond to FRs of a human antibody. In certain such embodiments, a humanized antibody further comprises a constant region (Fc) of a human antibody.

The term "human antibody" refers to a monoclonal antibody that contains human antibody sequences and does not contain antibody sequences from a non-human animal. In certain embodiments, a human antibody may contain synthetic sequences not found in native antibodies. The term is not limited by the manner in which the antibodies are made. For example, in various embodiments, a human antibody may be made in a transgenic mouse, by phage display, by human B-lymphocytes, or by recombinant methods.

As used herein, the term "natural antibody" refers to an antibody in which the heavy and light chains of the antibody have been made and paired by the immune system of a multicellular organism. For example, the antibodies produced by the antibody-producing cells isolated from a first animal immunized with an antigen are natural antibodies. Natural antibodies contain naturally-paired heavy and light chains. The term "natural human antibody" refers to an antibody in which the heavy and light chains of the antibody have been made and paired by the immune system of a human subject.

Native human light chains are typically classified as kappa and lambda light chains. Native human heavy chains are typically classified as mu, delta, gamma, alpha, or epsilon, and define the antibody's isotype as IgM, IgD, IgG, IgA, and IgE, respectively. IgG has subclasses, including, but not limited to, IgG1, IgG2, IgG3, and IgG4. IgM has subclasses including, but not limited to, IgM1 and IgM2. IgA has subclasses including, but not limited to, IgA1 and IgA2. Within native human light and heavy chains, the variable and constant regions are typically joined by a "J" region of about 12 or more amino acids, with the heavy chain also including a "D" region of about 10 more amino acids. See, e.g., Fundamental Immunology (1989) Ch. 7 (Paul, W., ed., 2nd ed. Raven Press, N.Y.); herein incorporated by reference in its entirety.

The term "neutralizing antibody" or "antibody that neutralizes" refers to an antibody that reduces at least one activity of a polypeptide comprising the epitope to which the antibody specifically binds. In certain embodiments, a neutralizing antibody reduces an activity in vitro and/or in vivo.

The term "antigen-binding site" refers to a portion of an antibody capable of specifically binding an antigen. In certain embodiments, an antigen-binding site is provided by one or more antibody variable regions.

The term "epitope" refers to any polypeptide determinant capable of specifically binding to an immunoglobulin or a T-cell or B-cell receptor. In certain embodiments, an epitope is a region of an antigen that is specifically bound by an antibody. In certain embodiments, an epitope may include chemically active surface groupings of molecules such as amino acids, sugar side chains, phosphoryl, or sulfonyl groups. In certain embodiments, an epitope may have specific three dimensional structural characteristics (e.g., a "conformational" epitope) and/or specific charge characteristics.

An epitope is defined as "the same" as another epitope if a particular antibody specifically binds to both epitopes. In certain embodiments, polypeptides having different primary amino acid sequences may comprise epitopes that are the same. In certain embodiments, epitopes that are the same may have different primary amino acid sequences. Different antibodies are said to bind to the same epitope if they compete for specific binding to that epitope.

As used herein, the term "mimotope" refers to a macromolecule (e.g., a peptide) which mimics the structure of an epitope. In some embodiments, a mimotope elicits an antibody response identical or similar to that elicited by the corresponding epitope. In some embodiments, an antibody that recognizes an epitope also recognizes a mimotope which mimics that epitope.

As used herein, the term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers a short polymer of amino acids linked together by peptide bonds. In contrast to other amino acid polymers (e.g., proteins, polypeptides, etc.), peptides are of about 30 amino acids or fewer in length. A peptide may comprise natural amino acids, non-natural amino acids, amino acid analogs, and/or modified amino acids. A peptide may be a subsequence of naturally occurring protein or a non-natural (synthetic) sequence.

As used herein, the term "mutant peptide" refers to a variant of a peptide having a distinct amino acid sequence from the most common variant occurring in nature, referred to as the "wild-type" sequence. A mutant peptide may be a subsequence of a mutant protein or polypeptide (e.g., a subsequence of a naturally-occurring protein that is not the most common sequence in nature), or may be a peptide that is not a subsequence of a naturally occurring protein or polypeptide. For example, a "mutant deamidated insulin peptide" may be a subsequence of a mutant version of native insulin or may be distinct sequence not found in naturally-occurring insulin proteins.

As used herein, the term "synthetic peptide" refers to a peptide having a distinct amino acid sequence from those found in natural peptides and/or proteins. A synthetic peptide is not a subsequence of a naturally occurring protein, either the wild-type (i.e., most abundant) or mutant versions thereof. For example, a "synthetic insulin peptide" is not a subsequence of a naturally occurring insulin. A "synthetic peptide," as used herein, may be produced or synthesized by any suitable method (e.g., recombinant expression, chemical synthesis, enzymatic synthesis, etc.). The terms "peptide mimetic" or "peptidomimetic" refer to a peptide-like molecule that emulates a sequence derived from a protein or peptide (e.g., deamidated insulin). A peptide mimetic or peptidomimetic may contain amino acids and/or non-amino acid components. Examples of peptidomimitecs include chemically modified peptides, peptoids (side chains are appended to the nitrogen atom of the peptide backbone, rather than to the α-carbons), β-peptides (amino group bonded to the β carbon rather than the α carbon), etc.

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:
1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (histidine (H), lysine (K), and arginine (R)); polar negative (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

"Non-conservative substitutions" involve the exchange of a member of one class for a member from another class.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

As used herein, the term "effective amount" refers to the amount of a composition sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., a deamidated insulin peptide and one or more other therapeutics for treating diabetes, etc.) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "pharmaceutical composition" refers to the combination of an active agent with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. (1975), incorporated herein by reference in its entirety.

DETAILED DESCRIPTION

Provided herein are epitopes and mimotopes thereof useful in the diagnosis and treatment of type 1 diabetes (T1D), as well as antibodies recognizing such epitopes, and diagnostics, therapeutics, kits, and methods of use thereof.

Figure 8:
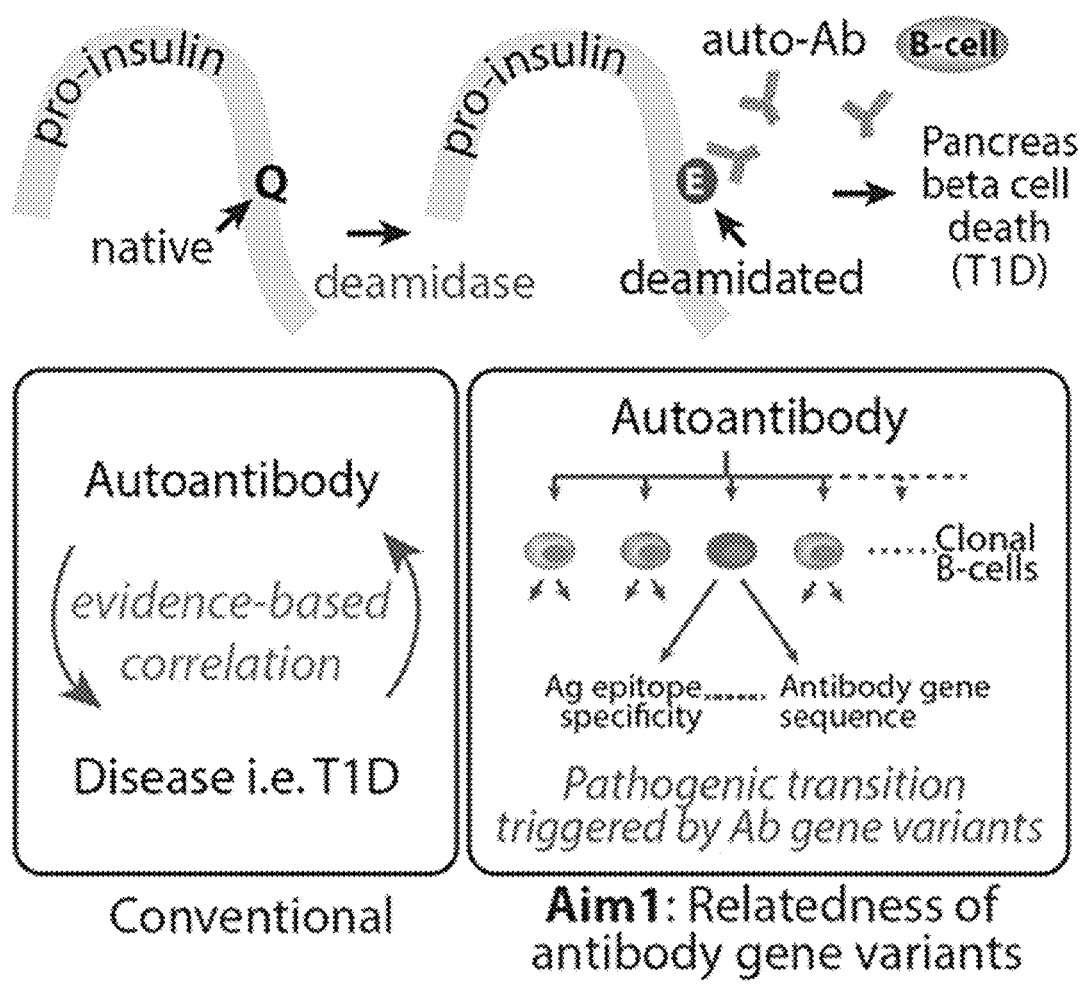
FIG. 8 shows a schematic depicting neo-antigenic responses to deamidated (Q→E) pro-insulin triggering autoimmune diabetes.

Experiments were conducted during development of embodiments herein to identify the molecular basis for anti-beta-cell immunity through a mechanism involving neoantigenic posttranslational modification (PTM) (FIG. 8). A biochemical approach was used to characterize T1D immune responses to a deamidated proinsulin epitope. Experiments demonstrated the catalysis of proinsulin deamidation on multiple glutamine (Gln/Q) residues by tissue transglutaminase (tTG/TG2, the major deamidase), and autoantibodies towards deamidated (but not native proinsulin) were detected in both T1D patients and non-obese diabetic (NOD) mice. In order to further delineate autoantibody specificity, a cell cloning strategy was used to successfully isolate individual lines of hybridomas that each produces an isoform of monoclonal antibody with specificity for deamidated proinsulin. Reactive epitopes for each monoclonal autoantibody were subsequently mapped out, and it was demonstrated that only a single deamidated residue of proinsulin accounts for all autoantibody reactivity.

Experiments conducted during development of embodiments herein demonstrating that pro-insulin can be deamidated on multiple glutamines (making it recognizable as 'non-self'), and autoantibodies specific for deamidated pro-insulin can be detected in the sera of T1D patients. From non-obese diabetic (NOD) mice were cloned 16 hybridoma lines, each expressing a single antibody isoform with naturally formed specificity for deamidated pro-insulin. Remarkably, these diabetes-related monoclonal autoantibodies show specificities toward a series of overlapping epitopes that are invariably anchored to a single deamidated glutamine (residue 22 in the C-peptide segment of pro-insulin (InsC22)). This convergence of antibody specificities indicates a "priming" function of this deamidated InsC22 residue in promoting autoimmunity. These finding indicate that in type I diabetes, the post-translationally deamidated InsC22 residue of pro-insulin, conspired with at-risk MEW isotypes in antigen cross-presentation, elicits neo-antigenic reactivity and therefore confers autoimmunity against islet cells.

In order to detect antibody reactivity specific towards deamidated insulin molecule, coding cDNA was constructed to produce a pair of testing protein antigens. The first one was derived from a wild-type (native/unmodified) mouse proinsulin sequence as control and the other derived from a mimotope of deamidated proinsulin sequence with a series of selected glutamine residues of the wild-type sequence being replaced by glutamic acid residues. Mouse sera were tested for antibody reactivity targeting deamidated antigens. Within the animal cohort, there was a strong correlation between positive antibody reactivity against deamidated proinsulin and onset of diabetes.

Experiments conducted during development of embodiments herein demonstrate that deamidation of proinsulin, particularly within the C-peptide, and more particularly at InsC22 of mouse C-peptide and/or the corresponding position in the human sequence, is causative of and/or dioagnostic of early-stage T1D, pre-T1D, and or high risk of developing T1D. As such, provided herein are methods (e.g., diagnostic tests) to identify a subject as type 1 diabetic, pre-diabetic, and/or at risk (e.g., high risk (e.g., likelihood >30%, <40%, >50%, >60%, >70%, >80%, >90%, >95%, >99%)) of developing T1D. In some embodiments, peptides and/or antibodies useful in performing such diagnostic methods are also provided. In some embodiments, such diagnostics allow for prevention of the development of T1D, delay of onset thereof, and/or early management of T1D and/or symptoms thereof. In some embodiments, because deamidation of proinsulin, particularly within the C-peptide, and more particularly at InsC22 of mouse C-peptide and/or the corresponding position in the human sequence, is causative of T1D, provided herein are therapeutic compositions (e.g., peptides and/or antibodies) and methods of use thereof for the prevention of development of T1D, treatment of T1D at an early stage, treatment of T1D, reduction of T1D symptoms, and/or management of T1D.

In some embodiments, insulin-based peptides and polypeptides (e.g., deamidated insulin, pro-insulin and/or fragments thereof) and compositions related thereto (e.g. peptide mimetics) are provided. In some embodiments, insulin-based peptides and polypeptides (e.g., deamidated insulin, pro-insulin and/or fragments thereof) and compositions related thereto (e.g. peptide mimetics) are provided for the diagnosis, risk stratification, and/or treatment of type 1 diabetes.

In some embodiments, provided herein are peptide sequences that are potentially prone to deamidation (e.g., by tTG) and that are a causative factor in the development and progression of T1D. In some embodiments, peptides comprise all or a portion of SEQ ID NO: 3 (or deamidated versions thereof (e.g., Q→E substitutions at 1, 2, 3, 4, or 5 of positions 7, 10, 23, 31, and/or 32 of SEQ ID NO: 2)). The invention also provides for peptide sequences, that are prone to deamidation by tTG and that are a causative factor of T1D. The invention also provides epitopes and mimotopes formed by deamidation of one or more of the Q residues of all or a portion of proinsulin (SEQ ID NO: 1) and/or C-peptide (SEQ ID NO: 2).

In some embodiments, provided herein deamidated pro-insulin-based peptide sequences (e.g., C-peptide-based) that are a causative factor in the development and progression of T1D. In some embodiments, peptides comprise all or a portion of one of SEQ ID NOS: 101-111.

In some embodiments, a peptide or polypeptide comprises a fragment of pro-insulin (e.g., a fragment of SEQ ID NO: 1) or a synthetic variant thereof. In some embodiments, a peptide or polypeptide comprises all or a fragment of the pro-insulin C-peptide (e.g., all or a fragment of SEQ ID NO: 2) or a synthetic variant thereof. In some embodiments, a peptide or polypeptide is provided comprising at least 50% (e.g., 50%, 55%, 60%, 65%, 70%, 75%, 80%, 85%, 90%, 95%, 100%, or ranges therebetween) sequence identity to one of SEQ ID NOS: 1 and/or 2, or a fragment thereof. In some embodiments, peptide and polypeptides comprise at least one substitution (e.g., 1, 2, 3, 4, 5, 6, 7, 8, 9, 10, 11, 12, 13, 14, 15, 16, 17, 18, 19, 20, or ranges therebetween) relative to a natural and/or wild-type sequence (e.g., SEQ ID NOS: 1-2, etc.). In some embodiments, a peptide or polypeptide is provided comprising at least 50% (e.g., 50%, 55%, 60%, 65%, 70%, 75%, 80%, 85%, 90%, 95%, 100%, or ranges therebetween) sequence similarity (e.g., conservative similarity, semi-conservative similarity, etc.) to one of SEQ ID NOS: 1-2 or a fragment thereof.

In some embodiments, a peptide or polypeptide is provided comprising at least 50% (e.g., 50%, 55%, 60%, 65%, 70%, 75%, 80%, 85%, 90%, 95%, 100%, or ranges therebetween) sequence identity to one of SEQ ID NOS: 101-111, or a fragment thereof. In some embodiments, peptide and polypeptides comprise at least one substitution (e.g., 1, 2, 3, 4, 5, 6, 7, 8, 9, 10, 11, 12, 13, 14, 15, 16, 17, 18, 19, 20, or ranges therebetween) relative to one of SEQ ID NOS: 101-111. In some embodiments, a peptide or polypeptide is provided comprising at least 50% (e.g., 50%, 55%, 60%, 65%, 70%, 75%, 80%, 85%, 90%, 95%, 100%, or ranges therebetween) sequence similarity (e.g., conservative similarity, semi-conservative similarity, etc.) to one of SEQ ID NOS: 101-111 or a fragment thereof.

In some embodiments, a peptide or polypeptide comprises one of the aforementioned peptide or polypeptide sequences (e.g., having a degree of sequence identity or similarity to all or a fragment of one of SEQ ID NOS: 1-2) with one or more (e.g., 1, 2, 3, 4, 5, 6, 7, 8, 9 10, 11, 12, 13, 14, 15, or more, or ranges therebetween) deamidated residues. In some embodiments, one or more glutamine and/or asparagine residues are deamidated. In some embodiments, one or more glutamine residues are deamidated to glutamic acid or isoglutamic acid. In some embodiments, one or more asparagine residues are deamidated to aspartic acid or isoaspartic acid.

In some embodiments, a peptide or polypeptide comprises one of the aforementioned peptide or polypeptide sequences (e.g., having a degree of sequence identity or similarity to all or a fragment of one of SEQ ID NOS: 1-2) with one or more (e.g., 1, 2, 3, 4, 5, 6, 7, 8, 9 10, 11, 12, 13, 14, 15, or more, or ranges therebetween) amide-containing residues (e.g., glutamine, asparagine) are replaced (e.g., substitution) for a residue (e.g., structurally-similar residue) lacking the amide group (e.g., aspartic acid, isoaspartic acid, glutamic acid, isoglutamic acid, etc.). In some embodiments, one or more glutamine and/or asparagine residues are deamidated. In some embodiments, one or more glutamine residues are deamidated to glutamic acid or isoglutamic acid. In some embodiments, one or more asparagine residues are deamidated to aspartic acid or isoaspartic acid.

In some embodiments, a peptide is provided comprising all or a portion of SEQ ID NO: 3 (or substantial (e.g., >70%, >75%, <80%, >85%, >90%, >95%) sequence identity and/or similarity with SEQ ID NO: 3), but having a Q→E substitution at InsC22. In some embodiments, the peptide further comprises additional deamidation substitutions (e.g., Q→E, N→D, etc.) at other positions.

In some embodiments, peptides, polypeptides, and mimetics for diagnosis, risk stratification, and treatment of T1D are provided. In some embodiments, in addition to deamidation and/or substitution to deamidated residues, the peptides/polypeptides comprise additional non-natural substitutions and modifications. In some embodiments, peptides and polypeptides described herein are further modified (e.g., substitution, deletion, or addition of standard amino acids; chemical modification; etc.). Modifications that are understood in the field include N-terminal modification, C-terminal modification (which protects the peptide from proteolytic degradation), alkylation of amide groups, hydrocarbon "stapling" (e.g., to stabilize conformations). In some embodiments, the peptides described herein may be modified by conservative residue substitutions, for example, of the charged residues (e.g., K to R, R to K, D to E and E to D) or the non-polar aliphatic (A to V, L, I, or M; V to A, L, I, or M; L to A, V, I, or M; I to M to A, V, L, or M; M to A, V, L, or I), etc. In some embodiments, such conservative substitutions provide subtle changes while preserving the local environment of the residue. Modifications of the terminal carboxy group include, without limitation, the amide, lower alkyl amide, constrained alkyls (e.g. branched, cyclic, fused, adamantyl) alkyl, dialkyl amide, and lower alkyl ester modifications. Lower alkyl is C1-C4 alkyl. Furthermore, one or more side groups, or terminal groups, may be protected by protective groups known to the ordinarily-skilled peptide chemist. The α-carbon of an amino acid may be mono- or dimethylated. In some embodiments, one or more intra-peptide disulfide bonds are introduced (e.g., between two cysteines within a peptide/polypeptide. In some embodiments, the presence of an intra-peptide disulfide bond stabilizes the peptide.

Embodiments described herein may comprise insulin-based peptidomimetics corresponding to the insulin-based peptides described herein with various modifications that are understood in the field. In some embodiments, residues in the peptide sequences described herein may be substituted with amino acids having similar characteristics (e.g., hydrophobic to hydrophobic, neutral to neutral, etc.) or having other desired characteristics (e.g., more acidic, more hydrophobic, less bulky, more bulky, etc.). In some embodiments, non-natural amino acids (or naturally-occurring amino acids other than the standard 20 amino acids) are substituted in order to achieve desired properties.

In some embodiments, residues having a side chain that is positively charged under physiological conditions, or residues where a positively-charged side chain is desired, are substituted with a residue including, but not limited to: lysine, homolysine, 6-hydroxylysine, homoarginine, 2,4-diaminobutyric acid, 3-homoarginine, D-arginine, arginal (—COOH in arginine is replaced by —CHO), 2-amino-3-guanidinopropionic acid, nitroarginine (N(G)-nitroarginine), nitrosoarginine (N(G)-nitrosoarginine), methylarginine (N-methylarginine), ε-N-methyllysine, allo-hydroxylysine, 2,3-diaminopropionic acid, 2,2'-diaminopimelic acid, ornithine, sym-dimethylarginine, asym-dimethylarginine, 2,6-diaminohexinic acid, p-aminobenzoic acid and 3-aminotyrosine and, histidine, 1-methylhistidine, and 3-methylhistidine. A neutral residue is a residue having a side chain that is uncharged under physiological conditions. A polar residue preferably has at least one polar group in the side chain. In some embodiments, polar groups are selected from hydroxyl, sulfhydryl, amine, amide and ester groups or other groups which permit the formation of hydrogen bridges.

In some embodiments, residues having a side chain that is neutral/polar under physiological conditions, or residues where a neutral side chain is desired, are substituted with a residue including, but not limited to: asparagine, cysteine, glutamine, serine, threonine, tyrosine, citrulline, N-methylserine, homoserine, allo-threonine and 3,5-dinitro-tyrosine, and β-homoserine.

Residues having a non-polar, hydrophobic side chain are residues that are uncharged under physiological conditions, preferably with a hydropathy index above 0, particularly above 3. In some embodiments, non-polar, hydrophobic side chains are selected from alkyl, alkylene, alkoxy, alkenoxy, alkylsulfanyl and alkenylsulfanyl residues having from 1 to 10, preferably from 2 to 6, carbon atoms, or aryl residues having from 5 to 12 carbon atoms. In some embodiments, residues having a non-polar, hydrophobic side chain are, or residues where a non-polar, hydrophobic side chain is desired, are substituted with a residue including, but not limited to: leucine, isoleucine, valine, methionine, alanine, phenylalanine, N-methylleucine, tert-butylglycine, octylglycine, cyclohexylalanine, β-alanine, 1-aminocyclohexylcarboxylic acid, N-methylisoleucine, norleucine, norvaline, and N-methylvaline.

In some embodiments, peptide and polypeptides are isolated and/or purified (or substantially isolated and/or substantially purified). Accordingly, in such embodiments, peptides and/or polypeptides are provided in substantially isolated form. In some embodiments, peptides and/or polypeptides are isolated from other peptides and/or polypeptides as a result of solid phase peptide synthesis, for example. Alternatively, peptides and/or polypeptides can be substantially isolated from other proteins after cell lysis from recombinant production. Standard methods of protein purification (e.g., HPLC) can be employed to substantially purify peptides and/or polypeptides. In some embodiments, the present invention provides a preparation of peptides and/or polypeptides in a number of formulations, depending on the desired use. For example, where the peptide is substantially isolated (or even nearly completely isolated from other proteins), it can be formulated in a suitable medium solution for storage (e.g., under refrigerated conditions or under frozen conditions). Such preparations may contain protective agents, such as buffers, preservatives, cryprotectants (e.g., sugars such as trehalose), etc. The form of such preparations can be solutions, gels, etc. In some embodiments, insulin-based peptides and/or polypeptides are prepared in lyophilized form. Moreover, such preparations can include other desired agents, such as small molecules or other peptides, polypeptides or proteins. Indeed, such a preparation comprising a mixture of different embodiments of the peptides and/or polypeptides described here may be provided.

In some embodiments, provided herein are peptidomimetic versions of the peptide sequences described herein or variants thereof. In some embodiments, a peptidomimetic is characterized by an entity that retains the polarity (or non-polarity, hydrophobicity, etc.), three-dimensional size, and functionality (bioactivity) of its peptide equivalent but wherein all or a portion of the peptide bonds have been replaced (e.g., by more stable linkages). In some embodiments, 'stable' refers to being more resistant to chemical degradation or enzymatic degradation by hydrolytic enzymes. In some embodiments, the bond which replaces the amide bond (e.g., amide bond surrogate) conserves some properties of the amide bond (e.g., conformation, steric bulk, electrostatic character, capacity for hydrogen bonding, etc.). Chapter 14 of "Drug Design and Development", Krogsgaard, Larsen, Liljefors and Madsen (Eds) 1996, Horwood Acad. Publishers provides a general discussion of techniques for the design and synthesis of peptidomimetics and is herein incorporated by reference in its entirety. Suitable amide bond surrogates include, but are not limited to: N-alkylation (Schmidt, R. et al., Int. J. Peptide Protein Res., 1995, 46, 47; herein incorporated by reference in its entirety), retro-inverse amide (Chorev, M. and Goodman, M., Acc. Chem. Res, 1993, 26, 266; herein incorporated by reference in its entirety), thioamide (Sherman D. B. and Spatola, A. F. J. Am. Chem. Soc., 1990, 112, 433; herein incorporated by reference in its entirety), thioester, phosphonate, ketomethylene (Hoffman, R. V. and Kim, H. O. J. Org. Chem., 1995, 60, 5107; herein incorporated by reference in its entirety), hydroxymethylene, fluorovinyl (Allmendinger, T. et al., Tetrahydron Lett., 1990, 31, 7297; herein incorporated by reference in its entirety), vinyl, methyleneamino (Sasaki, Y and Abe, J. Chem. Pharm. Bull. 1997 45, 13; herein incorporated by reference in its entirety), methylenethio (Spatola, A. F., Methods Neurosci, 1993, 13, 19; herein incorporated by reference in its entirety), alkane (Lavielle, S. et. al., Int. J. Peptide Protein Res., 1993, 42, 270; herein incorporated by reference in its entirety) and sulfonamido (Luisi, G. et al. Tetrahedron Lett. 1993, 34, 2391; herein incorporated by reference in its entirety).

As well as replacement of amide bonds, peptidomimetics may involve the replacement of larger structural moieties with di- or tripeptidomimetic structures and in this case, mimetic moieties involving the peptide bond, such as azole-derived mimetics may be used as dipeptide replacements. Suitable peptidomimetics include reduced peptides where the amide bond has been reduced to a methylene amine by treatment with a reducing agent (e.g. borane or a hydride reagent such as lithium aluminum-hydride); such a reduction has the added advantage of increasing the overall cationicity of the molecule.

Other peptidomimetics include peptoids formed, for example, by the stepwise synthesis of amide-functionalized polyglycines. Some peptidomimetic backbones will be readily available from their peptide precursors, such as peptides which have been permethylated, suitable methods are described by Ostresh, J. M. et al. in Proc. Natl. Acad. Sci. USA (1994) 91, 11138-11142; herein incorporated by reference in its entirety.

In some embodiments, the insulin-based peptides/polypeptides/mimetics that are disclosed herein may be further derivatized by chemical alterations, such as deamidation, glycosylation, acylation, sulfation, phosphorylation, acetylation, and cyclization. Such chemical alterations can be imparted through chemical or biochemical methodologies, as well as through in vivo processes, or any combination thereof.

In certain embodiments, the insulin-based peptides/polypeptides/mimetics described herein are derivatized by modification of the terminal amino group. Such modifications include, without limitation, the desamino, N-lower alkyl, N-di-lower alkyl, constrained alkyls (e.g. branched, cyclic, fused, adamantyl) and N-acyl modifications where the acyl moiety is C6-C20 alkyl.

In certain embodiments, the insulin-based peptides/polypeptides/mimetics described herein are derivatized by modification of the terminal carboxyl group. Such modifications include, without limitation, amide, lower alkyl amide, constrained alkyls (e.g. branched, cyclic, fused, adamantyl) alkyl, dialkyl amide, and lower alkyl ester modifications, where lower alkyl is C1-C4 alkyl. Furthermore, one or more side groups, or terminal groups, may be protected by protective groups known to the ordinarily-skilled peptide chemist. The α-carbon of an amino acid may be mono- or dimethylated.

In various embodiments, the insulin-based peptides/polypeptides/mimetics disclosed herein are derivatized by conjugation to one or more polymers or small molecule substituents. In certain of these embodiments, the insulin-based peptides/polypeptides/mimetics described herein are derivatized by coupling to polyethylene glycol (PEG). Coupling may be performed using known processes. See, Int. J. Hematology, 68:1 (1998); Bioconjugate Chem., 6:150 (1995); and Crit. Rev. Therap. Drug Carrier Sys., 9:249 (1992) all of which are incorporated herein by reference in their entirety. Those skilled in the art, therefore, will be able to utilize such well-known techniques for linking one or more polyethylene glycol polymers to the peptides and polypeptides described herein. Suitable polyethylene glycol polymers typically are commercially available or may be made by techniques well known to those skilled in the art. The polyethylene glycol polymers preferably have molecular weights between 500 and 20,000 and may be branched or straight chain polymers. The attachment of a polyethylene glycol (PEG) to a peptide or polypeptide described herein can be accomplished by coupling to amino, carboxyl or thiol groups. These groups will typically be the N- and C-termini and on the side chains of such naturally occurring amino acids as lysine, aspartic acid, glutamic acid and cysteine. Since the peptides and polypeptides of the present disclosure can be prepared by solid phase peptide chemistry techniques, a variety of moieties containing diamino and dicarboxylic groups with orthogonal protecting groups can be introduced for conjugation to PEG.

The present disclosure also provides for conjugation of the peptides and polypeptides described herein to one or more polymers other than polyethylene glycol.

In some embodiments, the peptides and polypeptides described herein are derivatized by conjugation or linkage to, or attachment of, polyamino acids (e.g., poly-his, poly-arg, poly-lys, etc.) and/or fatty acid chains of various lengths to the N- or C-terminus or amino acid residue side chains. In certain embodiments, the peptides and polypeptides described herein are derivatized by the addition of polyamide chains, particularly polyamide chains of precise lengths, as described in U.S. Pat. No. 6,552,167, which is incorporated by reference in its entirety. In yet other embodiments, the peptides and polypeptides are modified by the addition of alkylPEG moieties as described in U.S. Pat. Nos. 5,359,030 and 5,681,811, which are incorporated by reference in their entireties.

In select embodiments, the peptides and polypeptides disclosed herein are derivatized by conjugation to polymers that include albumin and gelatin. See, Gombotz and Pettit, Bioconjugate Chem., 6:332-351, 1995, which is incorporated herein by reference in its entirety. In further embodiments, the peptides and polypeptides disclosed herein are conjugated or fused to immunoglobulins or immunoglobulin fragments, such as antibody Fc regions. In various embodiments, the peptides and polypeptides described herein are derivatized by attaching small molecule substituents, including short chain alkyls and constrained alkyls (e.g., branched, cyclic, fused, adamantyl groups), and aromatic groups.

In certain embodiments, the peptides and polypeptides described herein comprise an alkylglycine amino acid analog comprising a C5-C9 straight or branched alkyl side chain, or a cycloalkyl group. In one embodiment, the peptide or polypeptide comprises an alkylglycine comprising a C6-C8 straight or branched alkyl side chain. In another embodiment, the polypeptide comprises an octylglycine comprising a C8 straight alkyl side chain (octyl-glycine).

In some embodiments, the insulin-based peptides/polypeptides/mimetics described herein are provided as fusions with other peptides or polypeptides. Such fusions may be expressed from a recombinant DNA which encodes the insulin-based peptides/polypeptides and the additional peptide/polypeptide or may be formed by chemical synthesis. The additional peptide/polypeptide may be fused to the N-terminus and/or the C-terminus of the insulin-based peptide/polypeptide/mimetic. In one embodiment, the fusion protein comprises a first peptide/polypeptide at the N-terminus and another (different) peptide/polypeptide at the C-terminus of the insulin-based peptide/polypeptide/mimetic. Optionally, the elements in the fusion are separated by a connector sequence, e.g., preferably one having at least 2 amino acid residues, such as one having 13 and up to 40 or 50 amino acid residues. The presence of a connector sequence in a fusion protein of the invention does not substantially alter the function of either element (e.g., the insulin-based peptide/polypeptide/mimetic) in the fusion relative to the function of each individual element, likely due to the connector sequence providing flexibility (autonomy) for each element in the fusion. In certain embodiment, the connector sequence is a sequence recognized by an enzyme or is photocleavable. For example, the connector sequence may include a protease recognition site.

The peptides and polypeptides described herein may be prepared as salts with various inorganic and organic acids and bases. Such salts include salts prepared with organic and inorganic acids, for example, with HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g. sodium and potassium salts, alkali earth salts, e.g. calcium and magnesium salts, and zinc salts. The salts may be formed by conventional means, such as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

The peptides and polypeptides described herein can be formulated as pharmaceutically acceptable salts and/or complexes thereof. Pharmaceutically acceptable salts include acid addition salts such as those containing sulfate, hydrochloride, phosphate, sulfamate, acetate, citrate, lactate, tartrate, succinate, oxalate, methanesulfonate, ethanesulfonate, benzenesulfonate, p-toluenesulfonate, cyclohexylsulfamate and quinate. Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

In certain embodiments, cyclodextrins may be added to an insulin-based peptide/polypeptide/mimetic as aqueous solubility enhancers. Cyclodextrins include methyl, dimethyl, hydroxypropyl, hydroxyethyl, glucosyl, maltosyl and maltotriosyl derivatives of alpha-, beta-, and gamma-cyclodextrin. An exemplary cyclodextrin solubility enhancer is hydroxypropyl-beta-cyclodextrin (HPBCD), which may be added to any of the above-described compositions to further improve the aqueous solubility characteristics of the peptides or polypeptides. In one embodiment, the composition comprises 0.1% to 20% HPBCD, 1% to 15% HPBCD, or from 2.5% to 10% HPBCD. The amount of solubility enhancer employed will depend on the amount of peptide or polypeptide of the present disclosure in the composition. In certain embodiments, the peptides may be formulated in non-aqueous polar aprotic solvents such as DMSO, dimethylformamide (DMF) or N-methylpyrrolidone (NMP).

In some embodiments, an antibody, or an antibody fragment thereof, that recognizes an epitope on a deamidated portion (e.g., C-peptide) of insulin and/or proinsulin is provided. In some embodiments, antibodies and/or antibody fragments that recognize/bind-to deamidated insulin, deamidated pro-insulin, deamidated C-peptide, and/or fragments thereof, and compositions related to such antibodies and/or antibody fragments are provided for the diagnosis, risk stratification, and/or treatment of type 1 diabetes.

In an exemplary embodiment, an antibody, or an antibody fragment thereof, is provided that is specific for a peptide or polypeptide comprising all or a portion of a pro-insulin C-peptide (SEQ ID NO: 3) in which one or more glutamine residues have been substituted for deamidated residues (e.g., glutamic acid).

In some embodiments, an antibody or antibody fragment comprises a heavy chain variable region having an amino acid sequence that is about 70%, 75%, 80%, 85%, 90%, 95%, 97%, 98%, 99% or 100% identical (or any ranges therein) to an amino acid sequence encoded by one of SEQ ID NOS: 39-54. In some embodiments, an antibody or antibody fragment comprises a heavy chain variable region having >50%, >60%, >70%, >75%, >80%, >85%, >90%, >95%, >97%, >98%, >99% or 100% sequence similarity (or any ranges therein) to an amino acid sequence encoded by one of SEQ ID NOS: 39-54 (See Table 1). In another embodiment, an antibody or antibody fragment of the invention comprises a light chain variable region having an amino acid sequence that is about 70%, 75%, 80%, 85%, 90%, 95%, 97%, 98%, 99% or 100% identical (or any ranges therein) to an amino acid sequence encoded by one of SEQ ID NOS: 55-70 (See Table 1). In some embodiments, an antibody or antibody fragment comprises a light chain variable region having >50%, >60%, >70%, >75%, >80%, >85%, >90%, >95%, >97%, >98%, >99% or 100% sequence similarity (or any ranges therein)) to an amino acid sequence encoded by one of SEQ ID NOS: 55-70.

TABLE 1

Exemplary $V_H/V_L$ DNA sequences

| Clone I.D. | Specificity | SEQ ID NO: | $V_H$ DNA Sequence | SEQ ID NO: | $V_L$ DNA Sequence |
|---|---|---|---|---|---|
| 29P3F11/ 11D10 | Dm-Ins2 | 39 | ATTGAGGTCAATCTGCAGGAGTCTGGGAG GCTAGTCTCAGTTTGGTGCCCTTGCCTCCCA CTTCAATGGCAGTTCTTTCCATTTCTCCAAC GAAGAGGTGGAGGTGCAACTGCAGGAGTC AGGAGGTGGCCTGGTGCAGCCTGGAGGAT CCCTGAAATTCTCCTGTGCAGCCTCAGGAAT CGATTTTAGAAGATGCTGGATGAGTTGGGT TCGGCGGGCTCCAGGGAAAGGACTCGAAT GGATTGGAGAAATTATTCCAGATAGCAGTA CATTAAACTATGCACCATCTCTAAAGGATAA ATTCATCATCTCCAGAGACAACGCCAAAAA TACGCTGTACCTGCAAATGAGCAAAGTGAG ATCTGAGGACACAGCCCTTTATTACTGTGTA AGACCTCTGTAATGGTTAC | 55 | CTTTGATATTGTGATGACGCAGGCTTTATT GAGGAAGTGACAGATGATTCCAGATTTTA GATCTGTGTATTGTGGAAGACGCAGGCTC CTGCTTCCTTAGCTGTATCTCTGGGGCAGA GGGCCACCATCTCATACAGGGCCAGCAAA AGTGTCAGTACATCTGGCTATAGTTATATG CACTGGAACCAACAGAAACCAGGACAGCC ACCCAGACTCCTCATCTATCTTGTATCCAAC CTAGAATCTGGGGTCCCTGCCAGGTTCAGT GGCAGTGGGTCTGGGACAGACTTCACCCT CAACATCCATCCTGTGGAGGAGGAGGATG CTGCAACCTATTACTGTCAGCACATTAGGG AGCTTACACGTTCGGAGGTGGACCAA |
| 27P4G3/ 6E6 | Dm-Ins2 | 40 | GAGGTCCAGCTGCAGGAGTCTGGGACTGA ACTGGTGAAGCCTGGGCTTCAGTGAAGCT GTCCTGCAAGGCTTCTGGCTACACCTTCACC AGCTACTGGATGCACTGGGTGAAGCAGAG GCCTGGACAAGGCCTTGAGTGGATTGGAA ATATTAATCCTAGCAATGGTGGTACTAACTA CAATGAGAAGTTCAAGAGCAAGGCCACACT GACTGTAGACAAATCCTCCAGCACAGCCTA | 56 | GATATTGTGATGACGCAGGCTCCATCCTCC CTGAGTGTGTCAGCAGGAGATAAGGTCAC TATGAGCTGCAAGTCCAGTCAGAGTCTGTT AAACAGTAGAAACCAAAAGAACTACTTGG CCTGGTACCAGCAGAAACCATGGCAGCCT CCTAAACTGCTGATCTACGGGCATCCACT AGGGAATCTGGGGTCCCTGATCGCTTCAC AGGCAGTGGATCTGGAACAGATTTCACTCT |

TABLE 1-continued

Exemplary V$_H$/V$_L$ DNA sequences

| Clone I.D. | Specificity | SEQ ID NO: | V$_H$ DNA Sequence | SEQ ID NO: | V$_L$ DNA Sequence |
|---|---|---|---|---|---|
| | | | CATGCAGCTCAGCAGCCTGACATCTGAGGA CTCTGCGGTCTATTATTGTGCAAGATGTTAC TACGGTAGTAACTATGCTATGGACTACTGG GGCCAAGGGACCACCGTCACCGTCTCCTCA | | CACCATCAGCAGTGTGCAGGCTGAAGACC TGGCAGTTTATTACTGTCAGAATGATTATA GTTATCCATTTACGTTCGGCACGGGGACAA AATTGGAAATAAAACGGGCTGATGCTGCA CCAACTGTATCC |
| 2P1B2/ 5B8 | Dm-Ins2 | 41 | GAGGTCAAGCTGCAGGAGTCAGGGACTGA ACTGGTGAAGCCTGGGGCTTCAGTGAAGCT GTCCTGCAAGGCTTCTGGCTACACCTTCACC AGCTACTGGATGCACTGGGTGAAGCAGAG GCCTGGACAAGGCCTTGAGTGGATTGGAA ATATTAATCCTAGCAATGGTGGTACTAACTA CAATGAGAAGTTCAAGAGCAAGGCCACACT GACTGTAGACAAATCCTCCAGCACAGCCTA CATGCAGCTCAGCAGCCTGACATCTGAGGA CTCTGCGGTCTATTATTGTGCAAGATGTAGT AACTCTATATTCTATGCTATGGACTACTGGG GCCAAGGGACCACCGTCACCGTCTCCTCA | 57 | GATATTGTGATGACGCAGGCTCCATCCTCC CTGAGTGTGTCAGCAGGAGATAAGGTCAC TATGAGCTGCAAGTCCAGTCAGAGTCTGTT AAACAGTAGAAACCAAAAGAACTACTTGG CCTGGTACCAGCAGAAACCATGGCAGCCT CCTAAACTGCTGATCTACGGGGCATCCACT AGGGAATCTGGGTCCCTGATCGCTTCAC AGGCAGTGGATCTGGAACAGATTTCACTCT CACCATCAGCAGTGTGCAGGCTGAAGACC TGGCAGTTTATTACTGTCAGAATGATTATA GTTATCCATTCACGTTCGGCACGGGGACAA AATTGGAAATAAAACGGGCTGATGCTGCA CCAACTGTATCC |
| 11P1G3/ 8G9 | Dim-Ins2 | 42 | GAGGTGAAACTGCAGCAGTCTGGGACTGA ACTGGTGAAGCCTGGGGCTTCAGTGAAGCT GTCCTGCAAGGCTTCTGGCTACACCTTCACC AGCTACTGGATGCACTGGGTGAAGCAGAG GCCTGGACAAGGCCTTGAGTGGATTGGAA ATATTAATCCTAGCAATGGTGGTACTAACTA CAATGAGAAGTTCAAGAGCAAGGCCACACT GACTGTAGACAAATCCTCCAGCACAGCCTA CATGCAGCTCAGCAGCCTGACATCTGAGGA CTCTGCGGTCTATTATTGTGCAAGATCCTAC TATGGTAACTACTATGCTATGGACTACTGG GGCCAAGGGACCACCGTCACCGTCTCCTCA | 58 | GGAGATAGGTCACTATGAGCTGCAAGTCC AGTCAGAGTCTGTTAAACAGTAGAAACCA AAAGAACTACTTGGCCTGGTACCAGCAGA AACCATGGCAGCCTCCTAAACTGCTGATCT ACGGGGCATCCACTAGGGAATCTGGGGTC CCTGATCGCTTCACAGGCAGTGGATCTGG AACAGATTTCACTCTCACCATCAGCAGTGT GCAGGCTGAAGACCTGGCAGTTTATTACT GTCAGAATGATTATAGTTATCCATTCACGT TCGGCACGGGGACAAAATTGGAAATAAA CGGGCTGATGCTGCACCAACTGTATCCA |
| 10P2 H2 | Dim-Ins2 | 43 | CTGCAGGAGTCAGGGACTGAACTGGTGAA GCCTGGGGCTTCAGTGAAGCTGTCCTGCAA GGCTTCTGGCTACACCTTCACCAGCTACTGG ATGCACTGGGTGAAGCAGAGGCCTGGACA AGGCCTTGAGTGGATTGGAAATATTAATCC TAGCAATGGTGGTACTAACTACAATGAGAA GTTCAAGAGCAAGGCCACACTGACTGTAGA CAAATCCTCCAGCACAGCCTACATGCAGCT CAGCAGCCTGACATCTGAGGACTCTGCGGT CTATTATTGTGCAAGATCTTACTACGGTAGT AGCTATGCTATGACT | 59 | TGATATTGTGATGACGCAGGCTCCATCCTC CCTGAGTGTGTCAGCAGGAGATAAGGTCA CTATGAGCTGCAAGTCCAGTCAGAGTCTGT TAAACAGTAGAAACCAAAAGAACTACTTG GCCTGGTACCAGCAGAAACCATGGCAGCC TCCTAAACTGCTGATCTACGGGGCATCCAC TAGGGAATCTGGGGTCCCTGATCGCTTCAC AGGCAGTGGATCTGGAACAGATTTCACTCT CACCATCAGCAGTGTGCAGGCTGAAGACC TGGCAGTTTATTACTGTCAGAATGATTATA GTTATCCATCACGTTCGGCACGG |
| 9P3A1/ 6G9 | Dim-Ins1/2 | 44 | GAGGTCAAACTGCAGCAGTCTGGACCTGGC CTAGTGCAGCCCTCACAGAGCCTGTCCATC ACCTGCACAGTCTCTGGTTTCTCATTAACTA GCTATGGTGTACACTGGGTTCGCCAGTCTC CAGGAAAGGGTCTGGAGTGGCTGGGAGTG ATATGGAGTGGTGGAAGCACAGACTATAAT GCAGCTTTCATATCCAGACTGAGCATCAGC AAGGACAATTCCAAGAGCCAAGTTTTCTTT AAAATGAACAGTCTGCAAGCTGATGACACA GCCATATATTACGCCCTATGGTAACTAGTTC TATGCTATGGACTACTGGGGCCAAGGGACC ACCGTCACCGTCTCCTC | 60 | GATATTGTGATGACGCAGGCTCCATCCTCC CTGAGTGTGTCAGCAGGAGATAAGGTCAC TATGAGCTGCAAGTCCAGTCAGAGTCTGTT AAACAGTAGAAACCAAAAGAACTACTTGG CCTGGTACCAGCAGAAACCATGGCAGCCT CCTAAACTGCTGATCTACGGGGCATCCACT AGGGAATCTGGGGTCCCTGATCGCTTCAC AGGCAGTGGATCTGGAACAGATTTCACTCT CACCATCAGCAGTGTGCAGGCTGAAGACC TGGCAGTTTATTACTGTCAGAATGATTATA GTTATCCTCACGTTCGGTGCTGGGACCA AGCTGGAGCTGAAACGGGCTGATGCTGCA CCAACTGTATCC |
| 27P5D8/ 10F8 | Dim-Ins1/2 | 45 | GAGGTCCAGCTGCAGGAGTCTGGACCTGG CCTAGTGCAGCCCTCACAGAGCCTGTCCAT CACCTGCACAGTCTCTGGTTTCTCATTAACT AGCTATGGTGTACACTGGGTTCGCCAGTCT CCAGGAAAGGGTCTGGAGTGGCTGGGAGT GATATGGAGTGGTGGAAGCACAGACTATA ATGCAGCTTTCATATCCAGACTGAGCATCA GCAAGGACAATTCCAAGAGCCAAGTTTTCT TTAAAATGAACAGTCTGCAAGCTGATGACA CAGCCATATATTACTGTGCCAGAGACGGGT ATGGTCCTGACTACTGGGGCCAAGGGACCA CCGTCACCGTCTCCTC | 61 | GATATTGTGATGACGCAGGCTCCACTCTCC CTGCCTGTCAGTCTTGGAGATCAAGCTTCA ATCTCTTGCAGATCTAGTCAGAGCCTTGTA CACAGCAATGGAAACACCTATTTATATTGG TACCTGCAGAAGCCAGGCCAGTCTCCAAA GCTCCTGATCTACAGGGTTCCAACCGATT TTCTGGGGTCCCAGACAGGTTCAGTGGCA GTGGATCAGGGACAGATTTCACACTCAAG ATCAGCAGAGTGGAGGCTGAGGATCTGG GAGTTTATTTCTGCTTCAAGGTACACATG TTCCGTATGCGTTCGGATCGGGACCAAG CTGGAAATAAAACGGGCTGATGCTGCACC AACTGTATCC |

TABLE 1-continued

Exemplary V_H/V_L DNA sequences

| Clone I.D. | Specificity | SEQ ID NO: | V_H DNA Sequence | SEQ ID NO: | V_L DNA Sequence |
|---|---|---|---|---|---|
| 27P4G2/ 5G7 | Dim-Ins1/2 | 46 | GAGGTCCAGCTGCAGGAGTCTGGACCTGG CCTAGTGCAGCCCTCACAGAGCCTGTCCAT CACCTGCACAGTCTCTGGTTTCTCATTAACT AGCTATGGTGTACACTGGGTTCGCCAGTCT CCAGGAAAGGGTCTGGAGTGGCTGGGAGT GATATGGAGTGGTGGAAGCACAGACTATA ATGCAGCTTTCATATCCAGACTGAGCATCA GCAAGGACAATTCCAAGAGCCAAGTTTTCT TTAAAATGAACAGTCTGCAAGCTGATGACA CAGCCATATATTACTGTGCCAGAGACGGGT ATGGTCCTGACTACTGGGGCCAAGGGACCA CCGTCACCGTCTCCTCA | 62 | CTTGGAGATCAGCTTCCATCTCTTGCAGAT CTAGTCAGAGCCTTGTACACAGCAATGGA AACACCTATTTATATTGGTACCTGCAGAAG CCAGGCCAGTCTCCAAAGCTCCTGATCTAC AGGGTTTCCAACCGATTTTCTGGGGTCCCA GACAGGTTCAGTGGCAGTGGATCAGGGAC AGATTTCACACTCAAGATCAGCAGAGTGG AGGCTGAGGATCTGGGAGTTTATTTCTGCT TTCAAGGTACACATGTTCCGTATACGTTCG GATCGGGACCAAGCTGGAAATAAAACG GGCTGATGCTGCACAAACTGTATCCA |
| 27P3F11/ 5F7 | Dim-Ins1/2 | 47 | GAGGTCCAGCTGCAGGAGTCAGGACCTGG CCTAGTGCAGCCCTCACAGAGCCTGTCCAT CACCTGCACAGTCTCTGGTTTCTCATTAACT AGCTATGGTGTACACTGGGTTCGCCAGTCT CCAGGAAAGGGTCTGGAGTGGCTGGGAGT GATATGGAGTGGTGGAAGCACAGACTATA ATGCAGCTTTCATATCCAGACTGAGCATCA GCAAGGACAATTCCAAGAGCCAAGTTTTCT TTAAAATGAACAGTCTGCAAGCTGATGACA CAGCCATATATTACTGTGCCAGAGACGGGT ATGGTCCTGACTACTGGGGCCAAGGGACCA CCGTCACCGTCTCCTCA | 63 | GATATTGTGATGACGCAGGCTCCACTCTCC CTGCCTGTCAGTCTTGGAGATCAAGCTTCC ATCTCTTGCAGATCTAGTCAGAGCCTTGTA CACAGCAATGGAAACACCTATTTATATTGG TACCTGCAGAAGCCAGGCCAGTCTCCAAA GCTCCTGATCTACAGGGTTTCCAACCGATT TTCTGGGGTCCCAGACAGGTTCAGTGGCA GTGGATCAGGGACAGATTTCACACTCAAG ATCAGCAGAGTGGAGGCTGAGGATCTGG GAGTTTATTTCTGCTTTCAAGGTACACATG TTCCTCGGACGTTCGGTGGAGGCACCAAG CTGGAAATCAAACGGGCTGATGCTGCACC AACTGTATCC |
| 27P4 A12 | Dim-Ins1/2 | 48 | AGGTGAAGGCGCAGGAGTCAGGACCTGGC CTAGTGCAGCCCTCACAGAGCCTGTCCATC ACCTGCACAGTCTCTGGTTTCTCATTAACTA GCTATGGTGTACACTGGGTTCGCCAGTCTC CAGGAAAGGGTCTGGAGTGGCTGGGAGTG ATATGGAGTGGTGGAAGCACAGACTATAAT GCAGCTTTCATATCCAGACTGAGCATCAGC AAGGACAATTCCAAGAGCCAAGTTTTCTTT AAAATGAACAGTCTGCAAGCTGATGACACA GCCATATATTACTGTGCCAGAGATGGTAAT GC | 64 | TTGATATTGTGGAGACGCAGGCTCCACTCT CCCTGCCTGTCAGTCTTGGAGATCAAGCTT CCATCTCTTGCAGATCTAGTCAGAGCCTTG TACACAGCAATGGAAACACCTATTTATATT GGTACCTGCAGAAGCCAGGCCAGTCTCCA AAGCTCCTGATCTACAGGGTTTCCAACCGA TTTTCTGGGGTCCCAGACAGGTTCAGTGGC AGTGGATCAGGGACAGATTTCACACTCAA GATCAGCAGAGTGGAGGCTGAGGATCTG GGAGTTTATTTCTGCTTTCAAGGTACACAT GTTCCTCAGCTCACGTTCGGTGCTGGACCA AGCTAG |
| 27P1 D6 | Dim-Ins1/2 | 49 | AGGTGAAGGCGCAGGAGTCAGGACCTGGC CTAGTGCAGCCCTCACAGAGCCTGTCCATC ACCTGCACAGTCTCTGGTTTCTCATTAACTA GCTATGGTGTACACTGGGTTCGCCAGTCTC CAGGAAAGGGTCTGGAGTGGCTGGGAGTG ATATGGAGTGGTGGAAGCACAGACTATAAT GCAGCTTTCATATCCAGACTGAGCATCAGC AAGGACAATTCCAAGAGCCAAGTTTTCTTT AAAATGAACAGTCTGCAAGCTGATGACACA GCCATATATTACTGTGCCAGAGACGGGTAT GTCT | 65 | TTGATATTGTGGAGACGCAGGCTCCACTCT CCCTGCCTGTCAGTCTTGGAGATCAAGCTT CCATCTCTTGCAGATCTAGTCAGAGCCTTG TACACAGCAATGGAAACACCTATTTATATT GGTACCTGCAGAAGCCAGGCCAGTCTCCA AAGCTCCTGATCTACAGGGTTTCCAACCGA TTTTCTGGGGTCCCAGACAGGTTCAGTGGC AGTGGATCAGGGACAGATTTCACACTCAA GATCAGCAGAGTGGAGGCTGAGGATCTG GGAGTTTATTTCTGCTTTCAAGGTACACAT GTTCCGTATACGTTCGGATCGGGACCAAG C |
| 9P5C6 | Dm-Ins2 | 50 | GCAGGAGTCAGGGGCTGAGCTTGTGAAGC CTGGGGCTTCAGTGAAGCTGTCCTGCAAGG CTTCTGGCTACACCTTCACCAGCTACTGGAT GCAGTGGGTAAAACAGAGGCCTGGACAGG GCCTTGAGTGGATCGGAGAGATTGATCCTT CTGATAGCTATACTAACTACAATCAAAAGTT CAAGGGCAAGGCCACATTGACTGTAGACAC ATCCTCCAGCACAGCCTACATGCAGCTCAG CAGCCTGACATCTGAGGACTCTGCGGTCTA TTACTGTGCAAGCCTA | 66 | TGATATTGTGGAAGACGCAGGCTCCACTCT CCCTGCCTGTCAGTCTTGGAGATCAAGCTT CCATCTCTTGCAGATCTAGTCAGAGCCTTG TACACAGCAATGGAAACACCTATTTATATT GGTACCTGCAGAAGCCAGGCCAGTCTCCA AAGCTCCTGATCTACAGGGTTTCCAACCGA TTTTCTGGGGTCCCAGACAGGTTCAGTGGC AGTGGATCAGGGACAGATTTCACACTCAA GATCAGCAGAGTGGAGGCTGAGGATCTG GGAGTTTATTTCTGCTTTCAAGGTACACAT GTTCCGTATACGTTCGGATCG |
| 27P1 C2 | Dim-Ins1 | 51 | TTGAGGTGAAGGCGCAGCAGTCAGGGGCT GAGCTGGTGAGGCCTGGGGCTTCAGTGAC GCTGTCCTGCAAGGCTTCGGGCTACACATT TACTGACTATGAAATGCACTGGGTGAAGCA GACACCTGTGCATGGCCTGGAATGGATTGG AGCTATTGATCCTGAAACTGGTGGTACTGC CTACAATCAGAAGTTCAAGGGCAAGGCCAT ACTGACTGCAGACAAATCCTCCAGCACAGC | 67 | TGATATTTGAGACGCAGGCTCCACTCTCC CTGCCTGTCAGTCTTGGAGATCAAGCTTCC ATCTCTTGCAGATCTAGTCAGAGCCTTGTA CACAGCAATGGAAACACCTATTTATATTGG TACCTGCAGAAGCCAGGCCAGTCTCCAAA GCTCCTGATCTACAGGGTTTCCAACCGATT TTCTGGGGTCCCAGACAGGTTCAGTGGCA GTGGATCAGGGACAGATTTCACACTCAAG |

TABLE 1-continued

Exemplary V_H/V_L DNA sequences

| Clone I.D. | Specificity | SEQ ID NO: | V_H DNA Sequence | SEQ ID NO: | V_L DNA Sequence |
|---|---|---|---|---|---|
| | | | CTACATGGAGCTCCGCAGCCTGACATCTGA GGACTCTGCCGTCTATTACTGTACCTAACTG AAG | | ATCAGCAGAGTGGAGGCTGAGGATCTGG GAGTTTATTTCTGCTTTCAAGGTACACATG TTCCTCATACGTCGGATCGGGAC |
| 27P4G5/ 6F6 | Dm-Ins2 | 52 | GAGGTCAAACTGCAGGAGTCAGGAGGTGG CCTGGTGCAGCCTGGAGGATCCCTGAAACT CTCCTGTGCAGCCTCAGGATTCGATTTTAGT AAAGACTGGATGAGTTGGGTCCGGCAGGC TACAGGGAAAGGGCTAGAATGAATTGGAG AAATTAATCCAGGTAGCAGTACGATAAACT ATACTCCATCTCTAAAGGATAAATTCATCAT CTCCAGAGACAACGCCAAAAATACGCTGTA CCTGCAAATGAGCAAAGTGAGATCTGAGG ACACAGCCCTTTATTACTGTGCAAGACCTCA CCACGGTGGTACTTCGATGTCTGGGCCAA GGGACCACCGTCACCGTCTCCTCA | 68 | GATATTGTGATGACGCAGGCTCCACTCTCC CTGCCTGTCAGTCTTGGAGATCAAGCTTCC ATCTCTTGCAGATCTAGTCAGAGCCTTGTA CACAGCAATGGAAACACCTATTTATATTGG TACCTGCAGAAGCCAGGCCAGTCTCCAAA GCTCCTGATCTACAGGGTTTCCAACCGATT TTCTGGGGTCCCAGACAGGTTCAGTGGCA GTGGATCAGGGACAGATTTCACACTCAAG ATCAGCAGAGTGGAGGCTGAGGATCTGG GAGTTTATTTCTGCTTTCAAGGTACACATG TTCCGTATACGTTCGGATCGGGGACCAAG CTGGAAATAAAACGGGCTGATGCTGCACC AACTGTATCC |
| 27P4B12/ 6E9 | Dm-Ins1/2 | 53 | GAGGTCAAACTGCAGGAGTCTGGACCTGG CCTAGTGCAGCCCTCACAGAGCCTGTCCAT CACCTGCACAGTCTCTGGTTTCTCATTAACT AGCTATGGTGTACACTGGGTTCGCCAGTCT CCAGGAAAGGGTCTGGAGTGGCTGGGAGT GATATGGAGTGGTGGAAGCACAGACTATA ATGCAGCTTTCATATCCAGACTGAGCATCA GCAAGGACAATTCCAAGAGCCAAGTTTTCT TTAAAATGAACAGTCTGCAAGCTGATGACA CAGCCATATATTACTGTGCCAGAGACGGGT ATGGTCCTGACTACTGGGGCCAAGGGACCA CCGTCACCGTCTCCTC | 69 | GATATTGTGATGACGCAGGCTCCACTGTCT TTGTCGGTTACCATTGGACAACCAGCCTCT ATCTCTTGCAAGTCAAGTCAGAGCCTCTTA TATAGTGATGGAAAGACATATTTGAATTG GTTACAACAGAGGCCAGGCCAGTCTCCAA AGCGCCTAATGTATCAGGTGTCCAAACTGA GACCCTGGCATCCCTGACAGGTTCAGTGG CAGTGGATCAGAGACAGATTTTACACTTAA AATCAGCAGAGTGGAGGCTGAGGATTTGG GAGTTTATTACTGCTTGCAAGGTACATATT ATCCGTATACGTTCGGATCGGGGACCAAG CTGGAAATAAAACGGGCTGATGCTGCACC AACTGTATCC |
| 27P1 B1 | Dm-Ins2 | 54 | TGTAGGTGAAGGCGCAGGAGTCAGGGGCT GAGCTTGTGAAGCCTGGGGCTTCAGTGAA GCTGTCCTGCAAGGCTTCTGGCTACACCTTC ACCAGCTACTGGATGCACTGGGTGAAGCA GAGGCCTGGACGAGGCCTTGAGTGGATTG GAAGGATTGATCCTAATAGTGGTGGTACTA AGTACAATGAGAAGTTCAAGAGCAAGGCC ACACTGACTGTAGACAAACCCTCCAGCACA GCCTACATGCAGCTCAGCAGCCTGACATCT GAGGACTCTGCGGTCTATTATGTGCAAGTT GTG | 70 | TGATATTGTGGAAGACGCAGGCTCCACTG TCTTTGTCGGTTACCATTGGACAACCAGCC TCTATCTCTTGCAAGTCAAGTCAGAGCCTC TTATATAGTGATGGAAAGACATATTTGAAT TGGTTACAACAGAGGCCAGGCCAGTCTCC AAAAGCGCCTAATGTATCAGGTGTCAAACT GGACCCTGGCATCCCTGACAGGTTCAGTG GCAGTGGATCAGAGACAGATTTTACACTTA AAATCAGCAGAGTGGAGGCTGAGGATTTG GGAGTTTATTACTGCTTGCAAGGTACATAT TATCCTCAGACGTTCGGTGAGC |

In some embodiments, an antibody or antibody fragment exhibits all or a portion of the epitope binding affinity of one of 29P3F11/11D10, 27P4G3/6E6, 2P1B2/5B8, 11P1G3/8G9, 10P2H2, 9P3A1/6G9, 27P5D8/10F8, 27P4G2/5G7 27P3F11/5F7, 27P4A12, 27P1D6, 9P5C6, 27P1C2, 27P4G5/6F6, 27P4B12/6E9, and 27P1B1 (Tables 1-3). In some embodiments, an antibody or antibody fragment binds the same epitope as one of 29P3F11/11D10, 27P4G3/6E6, 2P1B2/5B8, 11P1G3/8G9, 10P2H2, 9P3A1/6G9, 27P5D8/10F8, 27P4G2/5G7 27P3F11/5F7, 27P4A12, 27P1D6, 9P5C6, 27P1C2, 27P4G5/6F6, 27P4B12/6E9, and 27P1B1. In some embodiments, an antibody or antibody fragment exhibits the neutralizing activity of one of 29P3F11/11D10, 27P4G3/6E6, 2P1B2/5B8, 11P1G3/8G9, 10P2H2, 9P3A1/6G9, 27P5D8/10F8, 27P4G2/5G7 27P3F11/5F7, 27P4A12, 27P1D6, 9P5C6, 27P1C2, 27P4G5/6F6, 27P4B12/6E9, and 27P1B1. In some embodiments, an antibody is not a natural antibody. In some embodiments, an antibody is not a natural human antibody.

TABLE 2

Exemplary antibody heavy chain CDRs

| Clone I.D. | Specificity | SEQ ID NO: | CDR1H | SEQ ID NO: | CDR2H | SEQ ID NO: | CDR3H |
|---|---|---|---|---|---|---|---|
| 29P3F11/ 11D10 | Dm-Ins2 | 3 | GIDFRRCW | 7 | IIPDSSTL | | N.A. |
| 27P4G3/ 6E6 | Dm-Ins2 | 4 | GYTFTSYW | 8 | INPSNGGT | 13 | ARCYYGSNYAMDY |
| 2P1B2/ 5B8 | Dm-Ins2 | 4 | GYTFTSYW | 8 | INPSNGGT | 14 | ARCSNSIFYAMDY |

TABLE 2-continued

Exemplary antibody heavy chain CDRs

| Clone I.D. | Specificity | SEQ ID NO: | CDR1H | SEQ ID NO: | CDR2H | SEQ ID NO: | CDR3H |
|---|---|---|---|---|---|---|---|
| 11P1G3/ 8G9 | Dm-Ins2 | 4 | GYTFTSYW | 8 | INPSNGGT | 15 | ARSYYGNYYAMDY |
| 10P2H2 | Dm-Ins2 | 4 | GYTFTSYW | 8 | INPSNGGT | 16 | ARSYYGSSYAM |
| 9P3A1/ 6G9 | Dm-Ins1/2 | 5 | GFSLTSYG | 9 | IWSGGST |  | N.A. |
| 27PP5D8/ 10F8 | Dm-Ins1/2 | 5 | GFSLTSYG | 9 | IWSGGST | 17 | ARDGYGPDY |
| 27P4G2/ 5G7 | Dm-Ins1/2 | 5 | GFSLTSYG | 9 | IWSGGST | 17 | ARDGYGPDY |
| 27P3F11/ 5F7 | Dm-Ins1/2 | 5 | GFSLTSYG | 9 | IWSGGST | 17 | ARDGYGPDY |
| 27P4A12 | Dm-Ins1/2 | 5 | GFSLTSYG | 9 | IWSGGST | 18 | ARDGNAMDY |
| 27P1D5 | Dm-Ins1/2 | 5 | GFSLTSYG | 9 | IWSGGST | 17 | ARDGYGPDY |
| 9P5C6 | Dm-Ins2 | 4 | GYTFTSYW | 10 | IDPSDSYT | 19 | ARPYY |
| 27P1C2 | Dm-Ins1 | 6 | GYTFTDYE | 11 | IDPETGGT | 20 | TLTGKGY |
| 27P4G5/ 6F6 | Dm-Ins2 |  | N.A. |  | N.A. |  | N.A. |
| 27P4B12/ 6E9 | Dm-Ins1/2 | 5 | GFSLTSYG | 9 | IWSGGST | 17 | ARDGYGPDY |
| 27P1B1 | Dm-Ins2 | 4 | GYTFTSYW | 12 | IDPNSGGT | 21 | ASLFAY |

TABLE 3

Exemplary antibody light chain CDRs

| Clone I.D. | Specificity | SEQ ID NO: | CDR1L | SEQ ID NO: | CDR2L | SEQ ID NO: | CDR3L |
|---|---|---|---|---|---|---|---|
| 29P3F11/ 11D10 | Dm-Ins2 | 22 | KSVSTSGYSY | 27 | LVS |  | N.A. |
| 27P4G3/ 6E6 | Dm-Ins2 | 23 | QSLLNSRNQKNY | 28 | GAS | 31 | QNDYSYPFT |
| 2P1B2/ 5B8 | Dm-Ins2 | 23 | QSLLNSRNQKNY | 28 | GAS | 31 | QNDYSYPFT |
| 11P1G3/ 8G9 | Dm-Ins2 | 23 | QSLLNSRNQKNY | 28 | GAS | 31 | QNDYSYPFT |
| 10P2H2 | Dm-Ins2 | 23 | QSLLNSRNQKNY | 28 | GAS | 31 | QNDYSYPFT |
| 9P3A1/ 6G9 | Dm-Ins1/2 | 23 | QSLLNSRNQKNY | 28 | GAS | 32 | QNDYSYPLT |
| 27PP5D8/ 10F8 | Dm-Ins1/2 | 24 | QSLVHSNGNTY | 29 | RVS | 33 | FQGTHVPYA |
| 27P4G2/ 5G7 | Dm-Ins1/2 | 24 | QSLVHSNGNTY | 29 | RVS | 34 | FQGTHVPYT |
| 27P3F11/ 5F7 | Dm-Ins1/2 | 24 | QSLVHSNGNTY | 29 | RVS | 35 | FQGTHVPRT |
| 27P4A12 | Dm-Ins1/2 | 24 | QSLVHSNGNTY | 29 | RVS | 36 | FQGTHVPQLT |
| 27P1D5 | Dm-Ins1/2 | 24 | QSLVHSNGNTY | 29 | RVS | 34 | FQGTHVPYT |

TABLE 3-continued

Exemplary antibody light chain CDRs

| Clone I.D. | Specificity | SEQ ID NO: | CDR1L | SEQ ID NO: | CDR2L | SEQ ID NO: | CDR3L |
|---|---|---|---|---|---|---|---|
| 9P5C6 | Dm-Ins2 | 24 | QSLVHSNGNTY | 29 | RVS | 34 | FQGTHVPYT |
| 27P1C2 | Dm-Ins1 | 24 | QSLVHSNGNTY | 29 | RVS | 36 | FQGTHVPQLT |
| 27P4G5/ 6F6 | Dm-Ins2 | 24 | QSLVHSNGNTY | 29 | RVS | 34 | FQGTHVPYT |
| 27P4B12/ 6E9 | Dm-Ins1/2 | 25 | QSLLYSDGKTY | 30 | QVS | 37 | LQGTYYPYT |
| 27P1B1 | Dm-Ins2 | 26 | QSLLYSNGKTY | 30 | QVS | 38 | LQGTYYPQT |

The CDRs of the antibody heavy chains are referred to as CDRH1 (or CDR1H), CDRH2 (or CDR2H) and CDRH3 (or CDR3H), respectively. Similarly, the CDRs of the antibody light chains are referred to as CDRL1 (or CDR1L), CDRL2 (or CDR1L) and CDRL3 (or CDR1L), respectively. In some embodiments, antibodies or antibody fragments are provided with heavy chain CDR1 corresponding to one of SEQ ID NOs: 3-6. In some embodiments, antibodies or antibody fragments are provided with heavy chain CDR2 corresponding to one of SEQ ID NOs: 7-12. In some embodiments, antibodies or antibody fragments are provided with heavy chain CDR3 corresponding to one of SEQ ID NOs: 13-21. In some embodiments, antibodies or antibody fragments are provided with light chain CDRs corresponding to one of SEQ ID NOs: 3 and 7; 4, 8 and 13; 4, 8 and 14; 4, 8 and 15; 4, 8, and 16; 5 and 9; 5, 9, and 17; 5, 9, and 18; 4, 10, and 19; 6, 11, and 20; or 4, 12, and 21. In some embodiments, antibodies or antibody fragments are provided with light chain CDR1 corresponding to one of SEQ ID NOs: 22-26. In some embodiments, antibodies or antibody fragments are provided with light chain CDR2 corresponding to one of SEQ ID NOs: 27-30. In some embodiments, antibodies or antibody fragments are provided with light chain CDR3 corresponding to one of SEQ ID NOs: 31-38. In some embodiments, CDRs are provided having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.) with one of SEQ ID NOs: 22 and 27; 23, 28, and 31; 23, 28, and 32; 24, 29, and 33; 24, 29, and 34; 24, 29, and 35; 24, 29, and 36; 23, 30, and 37; or 26, 30, and 38. In some embodiments, CDRs are provided having at least 50% sequence similarity (e.g., 50%, 60%, 70%, 75%, 80%, 85%, 90%, 95%, 98%, 99%, 100%, and any ranges with such endpoints (e.g., 50-100%, 80-100%, 85-99%, 90-99%, etc.) with one of SEQ ID NOs: 22-38. In some embodiments, CDRs (or a combination thereof) are provided that recognize the same deamidated insulin, proinsulin, and/or C-peptide epitopes as 29P3F11/ 11D10, 27P4G3/6E6, 2P1B2/5B8, 11P1G3/8G9, 10P2H2, 9P3A1/6G9, 27P5D8/10F8, 27P4G2/5G7 27P3F11/5F7, 27P4A12, 27P1D6, 9P5C6, 27P1C2, 27P4G5/6F6, 27P4B12/6E9, and 27P1B1.

In certain embodiments, an antibody or antigen binding fragment comprises all of the CDRs of one of 29P3F11/ 11D10, 27P4G3/6E6, 2P1B2/5B8, 11P1G3/8G9, 10P2H2, 9P3A1/6G9, 27P5D8/10F8, 27P4G2/5G7 27P3F11/5F7, 27P4A12, 27P1D6, 9P5C6, 27P1C2, 27P4G5/6F6, 27P4B12/6E9, and 27P1B1, and binds the same deamidated insulin, proinsulin, and/or C-peptide epitopes. In some embodiments, an antibody or antigen binding fragment comprises CDRs with at least 70% sequence identity (e.g., >70%, >75%, >80%, >85%, >90%, >95%, >97%, >98%, >99% or 100%, and ranges therein) and/or at least 50% sequence similarity (e.g., >50%, >60%, >70%, >75%, >80%, >85%, >90%, >95%, >97%, >98%, >99% or 100%, and ranges therein) with the CDRs of antibody 29P3F11/ 11D10, 27P4G3/6E6, 2P1B2/5B8, 11P1G3/8G9, 10P2H2, 9P3A1/6G9, 27P5D8/10F8, 27P4G2/5G7 27P3F11/5F7, 27P4A12, 27P1D6, 9P5C6, 27P1C2, 27P4G5/6F6, 27P4B12/6E9, and 27P1B1, and binds the same deamidated insulin, proinsulin, and/or C-peptide epitopes.

The invention further comprises an antibody, or fragment thereof, that binds to the same epitope as an antibody described herein, or an antibody that competes with an antibody or antigen binding fragment described herein.

Antibodies within the scope described herein may also include hybrid antibody molecules that comprise one or more CDRs from an antibody described herein and one or more CDRs from another antibody to the same epitope. In one embodiment, such hybrid antibodies comprise three CDRs from an antibody described herein and three CDRs from another antibody to the same epitope. Exemplary hybrid antibodies comprise: (i) the three light chain CDRs from an antibody described herein and the three heavy chain CDRs from another antibody to the same epitope, or (ii) the three heavy chain CDRs from an antibody described herein and the three light chain CDRs from another antibody to the same epitope.

Variant antibodies are also included within the scope herein. Thus, variants of the sequences recited in the application are also included within the scope herein. Such variants include natural variants generated by somatic mutation in vivo during the immune response or in vitro upon culture of immortalized B cell clones. Alternatively, variants may arise due to the degeneracy of the genetic code, or may be produced due to errors in transcription or translation.

Further variants of the antibody sequences having improved affinity and/or potency may be obtained using methods known in the art and are included within the scope herein. For example, amino acid substitutions may be used to obtain antibodies with further improved affinity. Alternatively, codon optimization of the nucleotide sequence may be used to improve the efficiency of translation in expression systems for the production of the antibody. Further, polynucleotides comprising a sequence optimized for antibody specificity or neutralizing activity by the application of a directed evolution method to any of the nucleic acid sequences here are also within the scope included herein.

In some embodiments, variant antibody sequences may share 70% or more (e.g., 75%, 80%, 85%, 90%, 95%, 97%, 98%, 99% or more, or ranges therein) amino acid sequence identity with the sequences recited herein. In some embodiments, variant antibody sequences may share 50% or more (e.g., 55%, 60%, 65%, 75%, 80%, 85%, 90%, 95%, 97%, 98%, 99% or more, or ranges therein) amino acid sequence similarity with the sequences recited herein.

In one embodiment, nucleic acid sequences described herein include nucleic acid sequences having at least 70%, at least 75%, at least 80%, at least 85%, at least 90%, at least 95%, at least 98%, or at least 99% identity to a nucleic acid (e.g., SEQ ID NOs: 39-70 encoding a heavy or light chain of an antibody described herein.

Further included within the scope of the invention are vectors, for example, expression vectors, comprising a nucleic acid sequence described herein. Cells transformed with such vectors are also included. Examples of such cells include but are not limited to, eukaryotic cells, e.g. yeast cells, animal cells or plant cells. In one embodiment the cells are mammalian, e.g. human, CHO, HEK293T, PER.C6, NS0, myeloma or hybridoma cells.

In some embodiments, antibodies, antibody fragments, CDRs (e.g., CDR1H, CDR2H, CDR3H, CDR1L, CDR2L, CDR3L), $V_H$ chains, $V_L$ chains, etc. are provided that recognize, bind, neutralize, etc. deamidated human proinsulin epitopes (e.g., deamidated human C-peptide), human C-peptide or fragments thereof deamidated at the analogous position to InsC22, etc. In some embodiments, provided herein are antibodies, antibody fragments, CDRs (e.g., CDR1H, CDR2H, CDR3H, CDR1L, CDR2L, CDR3L), $V_H$ chains, $V_L$ chains, etc. that recognize human sequences in an analogous manner to the mouse antibodies, antibody fragments, CDRs (e.g., CDR1H, CDR2H, CDR3H, CDR1L, CDR2L, CDR3L), $V_H$ chains, $V_L$ chains, etc. described above. For example, provided herein are antibodies, antibody fragments, CDRs (e.g., CDR1H, CDR2H, CDR3H, CDR1L, CDR2L, CDR3L), $V_H$ chains, $V_L$ chains, etc. that recognize and/or are generated from epitopes comprising deamidated human C-peptide sequences, such as one of SEQ ID NOS: 101-111. In some embodiments, provided herein are antibodies, antibody fragments, CDRs (e.g., CDR1H, CDR2H, CDR3H, CDR1L, CDR2L, CDR3L), $V_H$ chains, $V_L$ chains, etc. that recognize and/or are generated from epitopes having at least 60% (e.g., 60%, 65%, 70%, 75%, 80%, 85%, 90%, 95%, 100%, or ranges therebetween) sequence identity with deamidated human C-peptide sequences, such as one of SEQ ID NOS: 101-111. In some embodiments, provided herein are antibodies, antibody fragments, CDRs (e.g., CDR1H, CDR2H, CDR3H, CDR1L, CDR2L, CDR3L), $V_H$ chains, $V_L$ chains, etc. that recognize and/or are generated from epitopes having at least 60% (e.g., 60%, 65%, 70%, 75%, 80%, 85%, 90%, 95%, 100%, or ranges therebetween) sequence similarity (e.g., conservative or semi-conservative similarity) with deamidated human C-peptide sequences, such as one of SEQ ID NOS: 101-111.

Embodiments within the scope of this disclosure include methods of diagnosis, risk stratification, and treatment of T1D using a therapeutically-, and/or diagnostically-effective amount of a monoclonal antibody having specificity for a deamidated insulin/proinsulin/C-peptide epitope. In some embodiments, an antibody recognizes (e.g., has affinity and/or specificity for) epitopes having at least 90%, at least 92%, at least 95%, at least 97%, at least 98%, or at least 99% homology to epitope(s) recognized by (e.g., has affinity and/or specificity for) the antibodies described herein.

Antibodies and fragments described herein may be coupled and/or conjugated to other agents to facilitate diagnosis, risk stratification, and treatment of T1D. For example, antibodies and antibody fragments may be coupled to a drug for delivery to a treatment site or coupled to a detectable label to facilitate imaging of a site comprising cells of interest. Methods for coupling antibodies to drugs and detectable labels are well known in the art, as are methods for imaging using detectable labels. Labeled antibodies may be employed in a wide variety of assays, employing a wide variety of labels. Detection of the formation of an antibody-antigen complex between an antibody of the invention and an epitope of interest can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include $^{125}$I, $^{131}$I, $^{35}$S, or $^{3}$H. Such labeled reagents may be used in a variety of well-known assays, such as radioimmunoassays, enzyme immunoassays, e.g., ELISA, fluorescent immunoassays, and the like.

An antibody may be conjugated to another therapeutic moiety. Such antibody conjugates can be used for modifying a given biological response; the drug moiety is not to be construed as limited to classical chemical therapeutic agents. For example, the drug moiety may be a protein or polypeptide possessing a desired biological activity. Techniques for conjugating such therapeutic moiety to antibodies are well known. See, for example, Arnon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-256; ed. Hellstrom et al. (1987) "Antibodies for Drug Delivery," in Controlled Drug Delivery, ed. Robinson et al. (2d ed; Marcel Dekker, Inc.), pp. 623-653; Thorpe (1985) "Antibody Carriers of Cytotoxic Agents in Cancer Therapy: A Review," in Monoclonal Antibodies '84: Biological and Clinical Applications, ed. Pinchera et al. pp. 475-506 (Editrice Kurds, Milano, Italy, 1985); "Analysis, Results, and Future Prospective of the Therapeutic Use of Radiolabeled Antibody in Cancer Therapy," in Monoclonal Antibodies for Cancer Detection and Therapy, ed. Baldwin et al. (Academic Press, New York, 1985), pp. 303-316; and Thorpe et al. (1982) Immunol. Rev. 62:119-158; herein incorporated by reference in their entireties.

Alternatively, an antibody, or antibody fragment thereof, can be conjugated to a second antibody, or antibody fragment thereof, to form an antibody heteroconjugate as described in U.S. Pat. No. 4,676,980; herein incorporated by reference in its entirety. In addition, linkers may be used between the labels and the antibodies of the invention (e.g. U.S. Pat. No. 4,831,175; herein incorporated by reference in its entirety). In some embodiments, antibodies or antibody fragments with three (e.g., trivalent) or more (tetravalent, multivalent, etc.) functional antigen binding sites are provided (See, e.g., WO 2001077342; herein incorporated by reference in its entirety).

Antibodies of the invention may also be attached to a solid support. Additionally, antibodies of the invention, or functional antibody fragments thereof, can be chemically modified by covalent conjugation to a polymer to, for example, increase their circulating half-life. In some embodiments the polymers may be selected from polyoxyethylated polyols and polyethylene glycol (PEG).

Water-soluble polyoxyethylated polyols armay also be employed. They include polyoxyethylated sorbitol, polyoxyethylated glucose, polyoxyethylated glycerol (POG), and the like. Another drug delivery system that can be used for increasing circulatory half-life is the liposome.

Antibodies may be provided in purified form. Typically, the antibody will be present in a composition that is substantially free of other polypeptides e.g. where less than 90% (by weight), usually less than 60% and more usually less than 50% of the composition is made up of other polypeptides.

Antibodies of the invention can be of any isotype (e.g. IgA, IgG, IgM (e.g., an alpha, gamma or mu heavy chain). Within the IgG isotype, antibodies may be IgG1, IgG2, IgG3 or IgG4 subclass. Antibodies may have a kappa or a lambda light chain.

In some embodiments, provided herein are isolated antibodies and antibody fragments against the deamidated insulin biomarkers (e.g., comprising C-peptide, comprising deamidated InsC22 or the human variant thereof) for the diagnosis, characterization, and/or risk stratification of T1D. Such antibodies and antibody fragments may be used, for example, in diagnostic and therapeutic methods. The antibody, or antibody fragment, may be any monoclonal or polyclonal antibody that specifically recognize deamidated insulin biomarkers. In some embodiments, provided herein are monoclonal antibodies, or fragments thereof. In some embodiments, the monoclonal antibodies, or fragments thereof, are chimeric or humanized antibodies. In other embodiments, the monoclonal antibodies, or fragments thereof, are human antibodies.

The antibodies of the present invention find use in experimental, diagnostic and therapeutic methods. In certain embodiments, the antibodies of the present invention are used to detect the presence, absence, or level of deamidated insulin markers in a sample from a patient. In certain embodiments, the antibodies of the present invention are used to quantify deamidated insulin markers in a sample.

Polyclonal antibodies can be prepared by any known method. Polyclonal antibodies can be raised by immunizing an animal (e.g. a rabbit, rat, mouse, donkey, etc.) by multiple subcutaneous or intraperitoneal injections of the relevant antigen (a purified peptide fragment, full-length recombinant protein, fusion protein, etc.,) optionally conjugated to keyhole limpet hemocyanin (KLH), serum albumin, etc. diluted in sterile saline and combined with an adjuvant (e.g. Complete or Incomplete Freund's Adjuvant) to form a stable emulsion. The polyclonal antibody is then recovered from blood, ascites and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay such as radioimmunoassay (MA) or enzyme-linked immunosorbent assay (ELISA) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated, such as from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In one embodiment, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity, affinity, etc. of a monoclonal antibody.

In some embodiments, the monoclonal antibody against deamidated insulin markers is a humanized antibody. Humanized antibodies are antibodies that contain minimal sequences from non-human (e.g., murine) antibodies within the variable regions. Such antibodies are used therapeutically to reduce antigenicity and HAMA (human anti-mouse antibody) responses when administered to a human subject. In practice, humanized antibodies are typically human antibodies with minimum to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDR of a human antibody with that of a non-human antibody (e.g. mouse, rat, rabbit, hamster, etc.) having the desired specificity, affinity, and capability (Jones et al., 1986, Nature, 321:522-525; Riechmann et al., 1988, Nature, 332:323-327; Verhoeyen et al., 1988, Science, 239:

1534-1536). The humanized antibody can be further modified by the substitution of additional residue either in the Fv framework region and/or within the replaced non-human residues to refine and optimize antibody specificity, affinity, and/or capability.

Human antibodies can be directly prepared using various techniques known in the art. Immortalized human B lymphocytes immunized in vitro or isolated from an immunized individual that produce an antibody directed against a target antigen can be generated (See, for example, Cole et al., Monoclonal Antibodies and Cancer Therapy, Alan R. Liss, p. 77 (1985); Boemer et al., 1991, J. Immunol., 147 (1):86-95; and U.S. Pat. No. 5,750,373). Also, the human antibody can be selected from a phage library, where that phage library expresses human antibodies (Vaughan et al., 1996, Nature Biotechnology, 14:309-314; Sheets et al., 1998, PNAS, 95:6157-6162; Hoogenboom and Winter, 1991, J. Mol. Biol., 227:381; Marks et al., 1991, J. Mol. Biol., 222:581). Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016; herein incorporated by reference in their entireties.

This invention also encompasses bispecific antibodies. Bispecific antibodies are antibodies that are capable of specifically recognizing and binding at least two different epitopes. Bispecific antibodies can be intact antibodies or antibody fragments. Techniques for making bispecific antibodies are common in the art (Millstein et al., 1983, Nature 305:537-539; Brennan et al., 1985, Science 229:81; Suresh et al, 1986, Methods in Enzymol. 121:120; Traunecker et al., 1991, EMBO J. 10:3655-3659; Shalaby et al., 1992, J. Exp. Med. 175:217-225; Kostelny et al., 1992, J. Immunol. 148:1547-1553; Gruber et al., 1994, J. Immunol. 152:5368; and U.S. Pat. No. 5,731,168).

In certain embodiments of the invention, it may be desirable to use an antibody fragment, rather than an intact antibody, to increase tumor penetration, for example. Various techniques are known for the production of antibody fragments. Traditionally, these fragments are derived via proteolytic digestion of intact antibodies (for example Morimoto et al., 1993, Journal of Biochemical and Biophysical Methods 24:107-117 and Brennan et al., 1985, Science, 229:81). However, these fragments are now typically produced directly by recombinant host cells as described above. Thus Fab, Fv, and scFv antibody fragments can all be expressed in and secreted from E. coli or other host cells, thus allowing the production of large amounts of these fragments. Alternatively, such antibody fragments can be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

It may further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

The present invention further embraces variants and equivalents which are substantially homologous to the chimeric, humanized and human antibodies, or antibody fragments thereof, set forth herein. These can contain, for example, conservative substitution mutations, for example, the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid.

In some embodiments, a field test or rapid diagnostic assay is provided. Such assays provide quick and/or inexpensive screening. A rapid diagnostic assay is a rapid assay meaning that the time to conduct the test from drawing of a bodily fluid to completing the test is rapid (e.g. less than 24 hours (e.g., <12 hours, <6 hours, <2 hours, <1 hour, <30 minutes, <10 minutes, <2 minutes, <1 minute)). In some embodiments, assays are provided that have diagnostic sensitivity and the specificity, but can be performed outside of a clinic or laboratory and/or without additional equipment or reagents. In some embodiments, test are performed without sample processing (e.g., on whole samples (e.g., whole blood)). In some embodiments, a test maybe performed at remote locations and in suboptimal conditions (e.g., high temperature, lack of cleanliness, by an untrained individual (e.g., self-administered), etc.) and still provide reliable diagnostic results. In some embodiments, a self-administered test is provided.

In some embodiments, an assay is contained within a single device or unit. In such embodiments, the assay is performed by exposing the device or unit to sample (e.g., blood) and observing the results (e.g., as is done with a home pregnancy test). In some embodiments, a user (e.g., the subject of the assay) draws a small amount of blood and applies it to the device, and the device provides an output indicating whether the subject is positive or negative for T1D, or risk of T1D. In some embodiments, minimal processing steps are required to perform the test (e.g., shaking, rinsing, diluting, etc.). In some embodiments, an assay device is for home use. In some embodiments, an assay device and the reagents therein are stable and usable without refrigeration. In some embodiments, a device and the reagents therein are stable (e.g., remain usable) for greater than 6 months (e.g., >6 months, >1 year, >2 years, >5 years, etc.).

In some embodiments, assays are provided that are performed by a clinician and/or a testing facility. In some embodiments, a computer-based analysis program is used to translate the raw data generated by the detection assay (e.g., the presence, absence, or amount of deamidated insulin markers) into data of predictive value for a clinician. In some embodiments, data analysis produces a T1D score, risk score, etc.

In some embodiments, a clinician accesses the data and/or analysis thereof using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

Embodiments here utilize any method capable of receiving, processing, and transmitting the information to and from laboratories conducting the assays, information provides, medical personal, and subjects. For example, in some embodiments of the present invention, a sample (e.g., a biopsy or a blood or serum sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a blood sample, etc.) and directly send it to a profiling center. Where the sample also comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (e.g., expression data), specific for the diagnostic or prognostic information desired for the subject.

In some embodiments, a report is generated (e.g., by a clinician, by a testing center, by a computer or other automated analysis system, etc.). A report may contain test results, diagnoses, and/or treatment recommendations.

In some embodiments, a sample (e.g., blood sample) from a subject (e.g., human) is tested to detect and/or determine the level of deamidated insulin biomarkers. In some embodiments, data analysis comprises comparing the level of deamidated insulin biomarkers biomarkers to a threshold value or range.

In some embodiments, the deamidated insulin-based peptides described herein, and the antibodies and antibody fragments capable of recognizing and binding to deamidated insulin in a subject are provided for the treatment or prevention of T1D. Embodiments herein are not limited by the methods or techniques of treating or preventing T1D. For example, in some embodiments, deamidation of insulin is inhibited, generation of autoantibodies to deamidated insulin is prevented, immune response from autoantibodies is prevented, etc.

A further embodiment is an isolated HLA-DQ restricted T-cell capable of recognizing a deamidated insulin-derived epitope according to the invention and more specifically an isolated or recombinant HLA-DQ restricted T-cell receptor capable of recognizing such an epitope.

In some embodiments, chimeric T cell receptors are utilized to prevent the immunologic response to the deamidated T cells.

Further, embodiments herein comprise a methods to inhibit the binding of a T cell receptor to an HLA-bound deamidated insulin epitope, to an HLA-bound deamidated insulin-derived epitope, or to an HLA-bound auto-antigen derived epitope comprising providing a blocking substance, preferably by blocking the binding of said epitopes to the HLA molecules. Also comprised herein are analogues of the epitopes herein which are an antagonists for the activity of T cells recognizing said epitope. Additionally provided is a pharmaceutical composition comprising a peptide or an epitope herein, which may preferably be used for the induction of tolerance or for the treatment of T1D.

In some embodiments, provided herein are compositions and methods to decrease sensitivity to insulin-derived auto-antigens by inhibiting the deamidation of said auto-antigens, preferably by inhibiting the function of tTG and most preferably at the site of presence of the auto-antigen.

In addition to therapeutic and prophylactic applications, embodiments herein are useful in, for example, risk stratification in pre-onset Type 1 diabetes, Type 1 diabetes diagnostic test, Type 2 diabetes islet health assessment, treatment of T1D, etc. Certain embodiments herein provide advantages over existing technologies, including, but not limited to: tests for detecting antibody-mediated autoimmune responses in Type 1 diabetes using native forms of protein antigens (including insulin) as testing substrates; the use of post-translationally modified proinsulin antigen, namely deamidated proinsulin as testing substrates; the use of deamidated versus native insulin, proinsulin, or peptide fragments thereof allows for detection of sources directly related to disease pathogenesis; etc.

In some embodiments, provided herein are diagnostic assays for the diagnosis or characterization of: risk of developing T1D, a pre-T1D state, early stage T1D (e.g., pre-symptomatic), T1D, etc. In some embodiments, experiments conducted during development of embodiments herein indicate the presence of deamidated insulin (e.g., proinsulin, C-peptide, position 22 (or human analog), etc.) and autoantibodies thereto, in subjects at risk of developing T1B, with pre-T1D, with a pre-T1D state, with an early stage T1D (e.g., pre-symptomatic), with T1D etc. In some embodiments, diagnostic assays are provided to detect deamidated insulin (e.g., proinsulin, C-peptide, position 22 (or human analog), etc.) and/or the autoantibodies thereto in a sample (e.g., blood sample), in order to characterize a T1D state and/or risk in the subject. In some embodiments, in which deamidated insulin (e.g., proinsulin, C-peptide, position 22 (or human analog), etc.) is to be detected in a sample from the subject, antibodies (e.g., monoclonal antibodies, antibody fragments, etc.) that recognize the deamidated insulin sequences are used as a diagnostic reagent. In some embodiments, in which autoantibodies that recognize/bind deamidated insulin (e.g., proinsulin, C-peptide, position 22 (or human analog), etc.) are to be detected in a sample from the subject, the deamidated insulin-based peptides described herein (e.g., human versions) that are recognized by the autoantibodies are used as a diagnostic reagent.

In certain embodiments, antibody (diagnostic-reagent antibody, autoantibody from subject, etc.) binding to deamidated sequence (e.g., deamidated insulin from subject, diagnostic-reagent peptide, etc.) is detected by techniques known in the art (e.g., radioimmunoassay, ELISA (enzyme linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In certain embodiments, antibody binding to a deamidated biomarker is detected by detecting a label on a primary antibody. In another embodiment, the primary antibody is detected by detecting binding of a secondary antibody or reagent to the primary antibody. In a further embodiment, the secondary antibody is labeled.

In certain embodiments, diagnostic deamidated peptide binding to an autoantibody in a sample from a subject is detected by detecting a label on a the peptide. In another embodiment, the bound peptide is detected by detecting binding of a diagnostic antibody or other labeled reagent to the deamidated peptide. In some embodiments, the diagnostic antibody is labeled.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. In other embodiments, the immunoassay described in U.S. Pat. Nos. 5,599,677 and 5,672,480 (each of which is herein incorporated by reference) is utilized.

Diagnostic kits may include any and all components necessary or sufficient for assays including, but not limited to, detection reagents (e.g., deamidated peptides, antibodies, etc.), buffers, control reagents (e.g., tissue samples, positive and negative control sample, etc.), solid supports, labels, written and/or pictorial instructions and product information, labeling and/or detection reagents, package environmental controls (e.g., ice, desiccants, etc.), and the like. In some embodiments, kits provide a subset of the required components, wherein it is expected that the user will supply the remaining components. In some embodiments, the kits comprise two or more separate containers wherein each container houses a subset of the components to be delivered.

EXPERIMENTAL

Example 1

Neo-Antigenicity of Deamidated Pro-Insulin in T1D Patients and in Animal Model

Following a proteomic survey that showed extensive post-translational deamidation of glutamine residues of insulin and pro-insulin, experiments were conducted to investigate whether deamidated insulin is pro-antigenic in diabetes. Native (as negative control) and deamidated insulin as testing antigens to probe for serum antibody reactivity specifically against deamidated insulin. Glutamine deamidation reaction produces several molecular species including glutamic acid that comprises ~25% of the end products. Pro-insulin was produced with selected glutamine residues replaced by glutamic acid to represent deamidated forms of pro-insulin. Using a diabetic mouse model, serum antibody reactivity for deamidated pro-insulin was observed; also observed was a strong correlation between anti-deamidation reactivity and diabetic onset.

Figure 2:
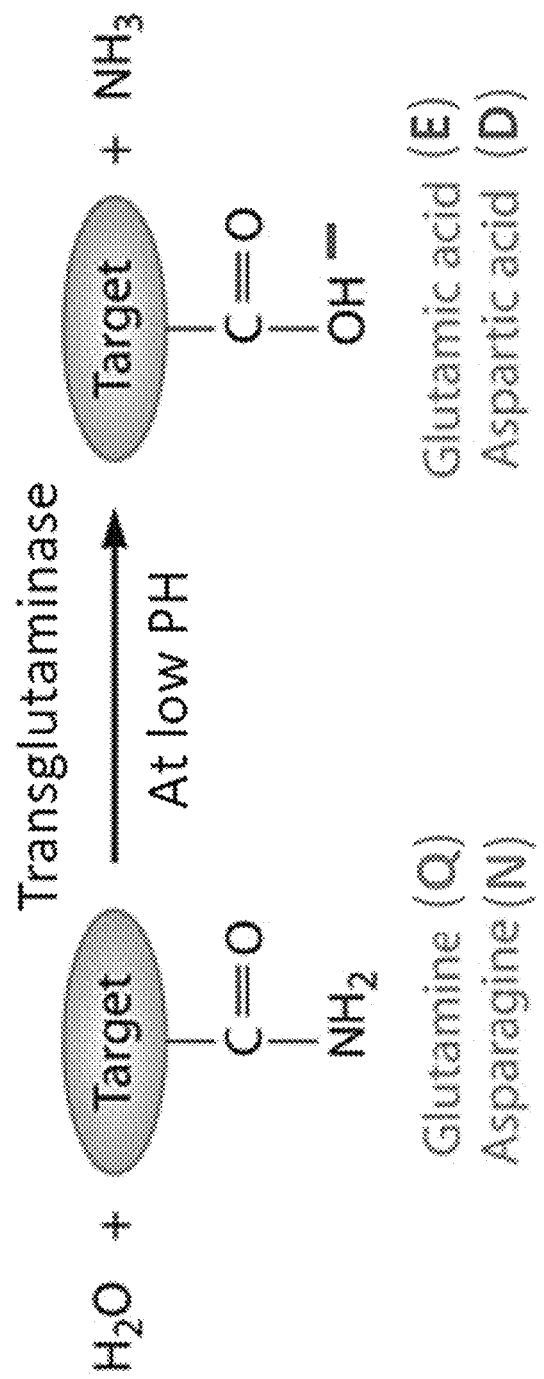
FIG. 2 shows a schematic depicting transglutaminase catalyzes a deamidation reaction that converts glutamine to glutamic acid and asparagine to aspartic acid with the gain of negative charge.
Figure 3:
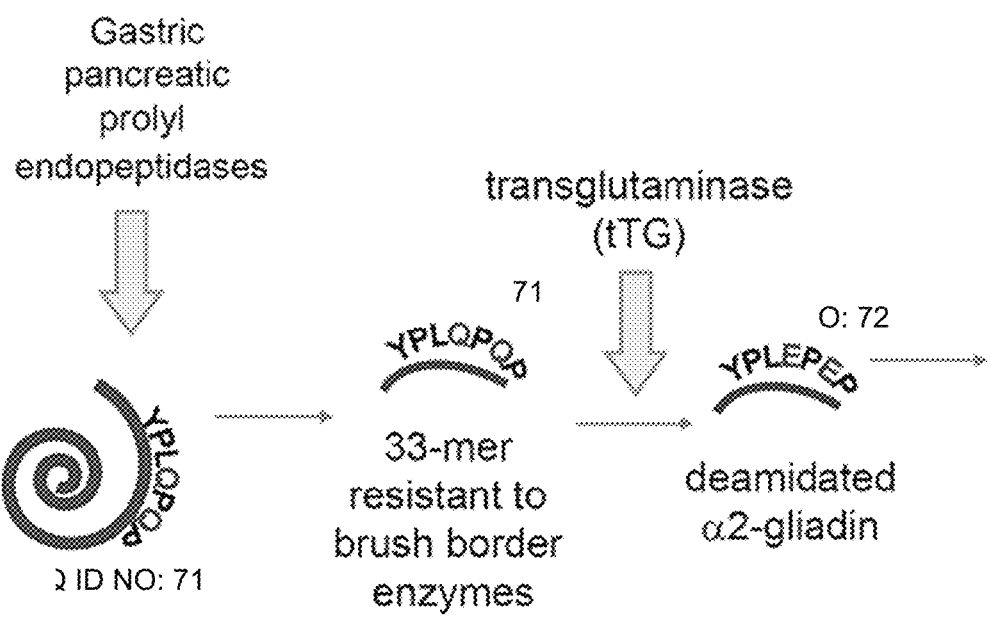
FIG. 3 shows a schematic depicting the molecular basis for celiac disease: A 33 amino acid gluten peptide is deamidated and becomes a suited ligand for HLA-DQ2/8.
Figure 3:
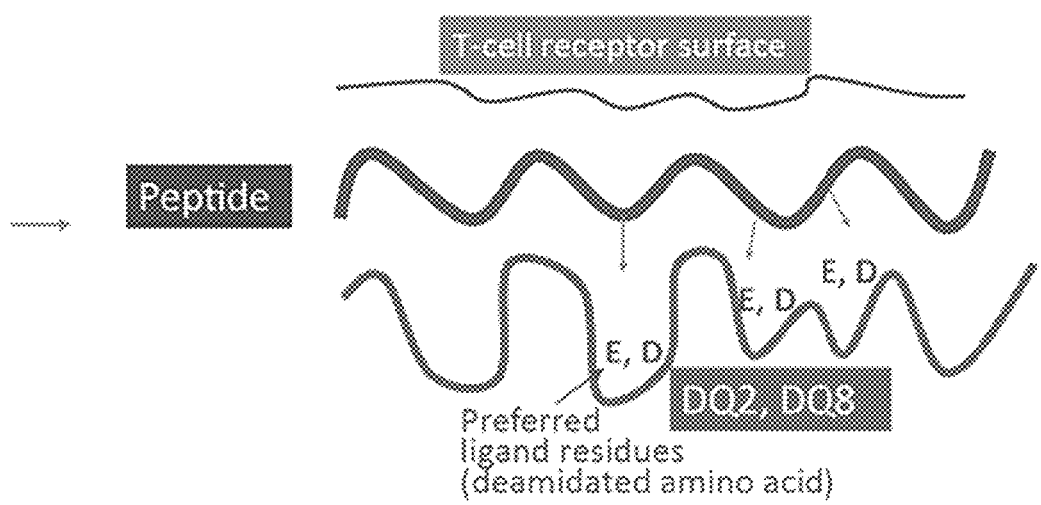
Figure 4:
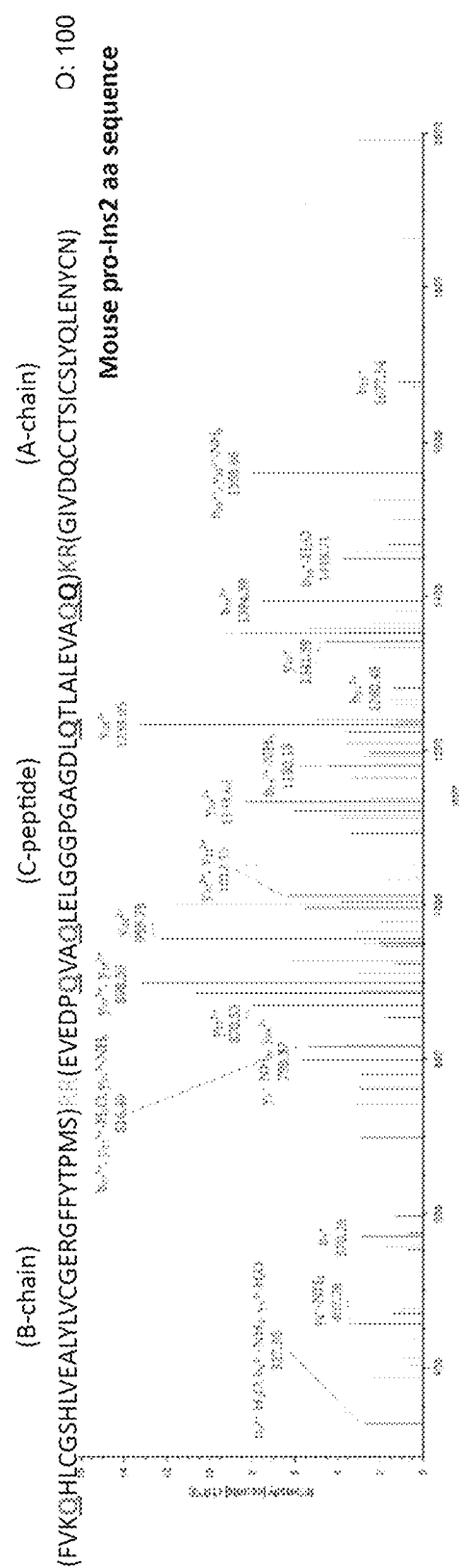
FIG. 4 shows post-translational modifications on mouse Ins2 protein identified by tandem mass spectrometry (MS-MS). Insulin was purified from mouse pancreatic islet extract. Following proteolytic digenstion with trypsinm the samples were analyzed by LC-MS/MS. MS2 ion graph for C-peptide containing deamidated glutamine 65 (Q65) is shown. Additional deamidation on Q residues are highlighted.
Figure 5:
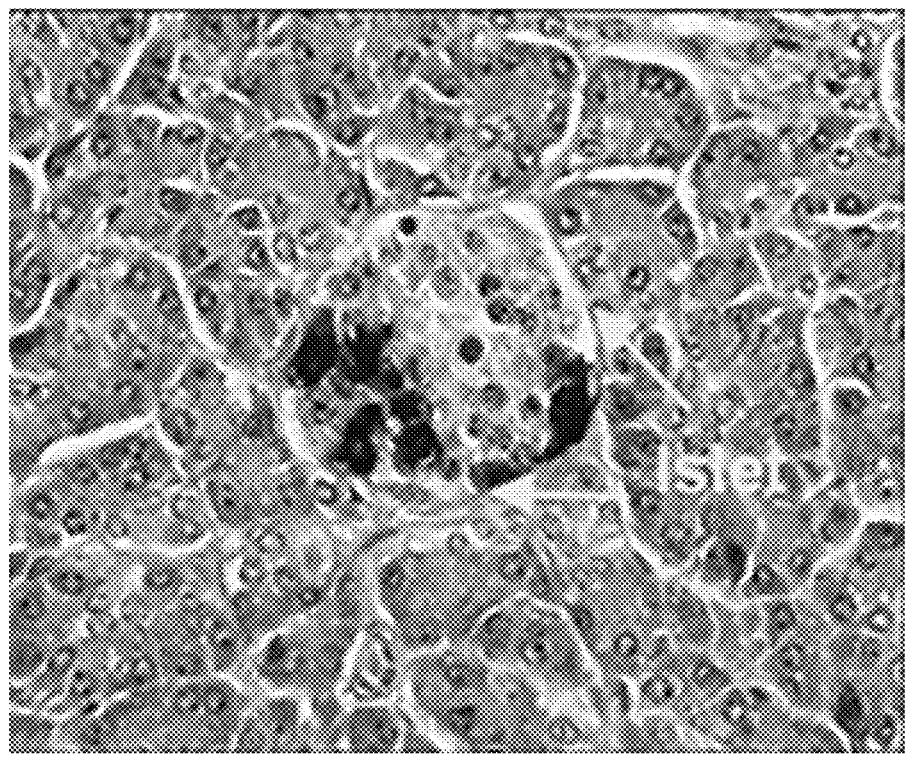
FIG. 5 shows an immunohistochemistry study of tissue transglutaminase (tTG, DAB staining) protein expression in human pancreas.
Figure 6:
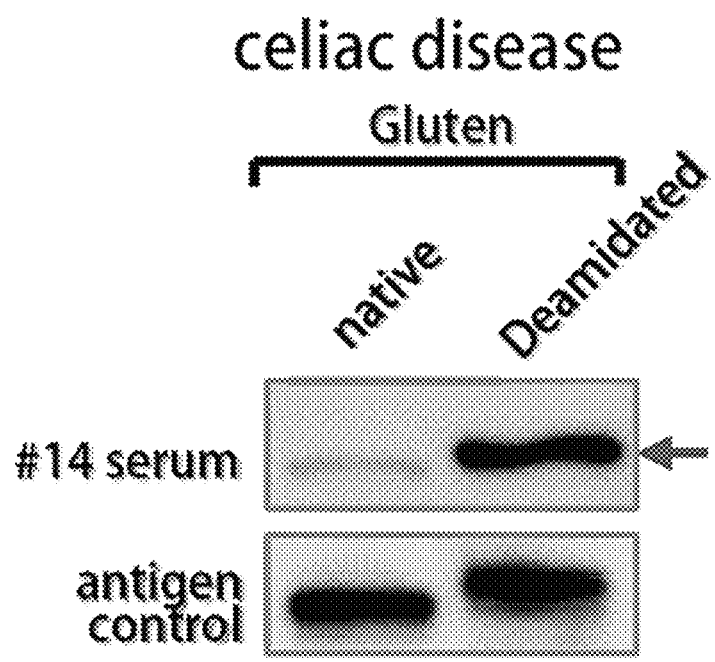
FIG. 6 shows immune reactivity of human plasma of a T1D patient to deamidated antigen over native antigen, using native vs. deamidated gluten and celiac disease as a control.
Figure 6:
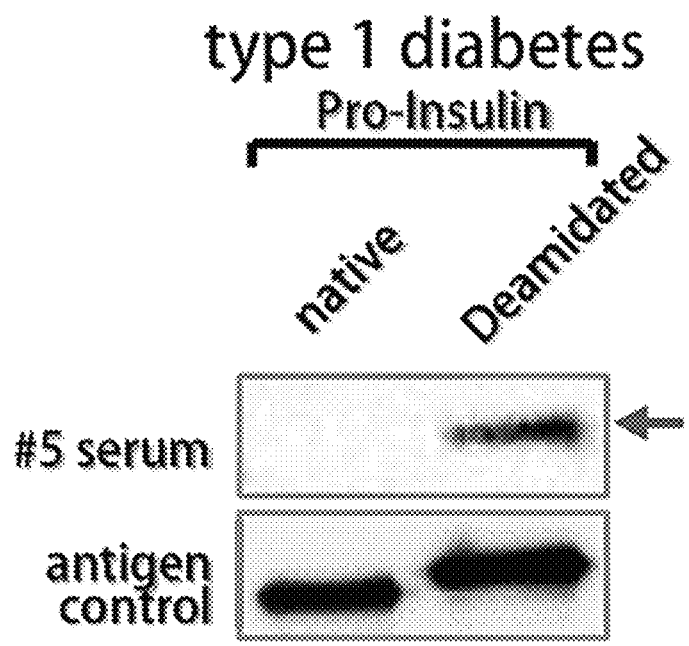
Figure 7:
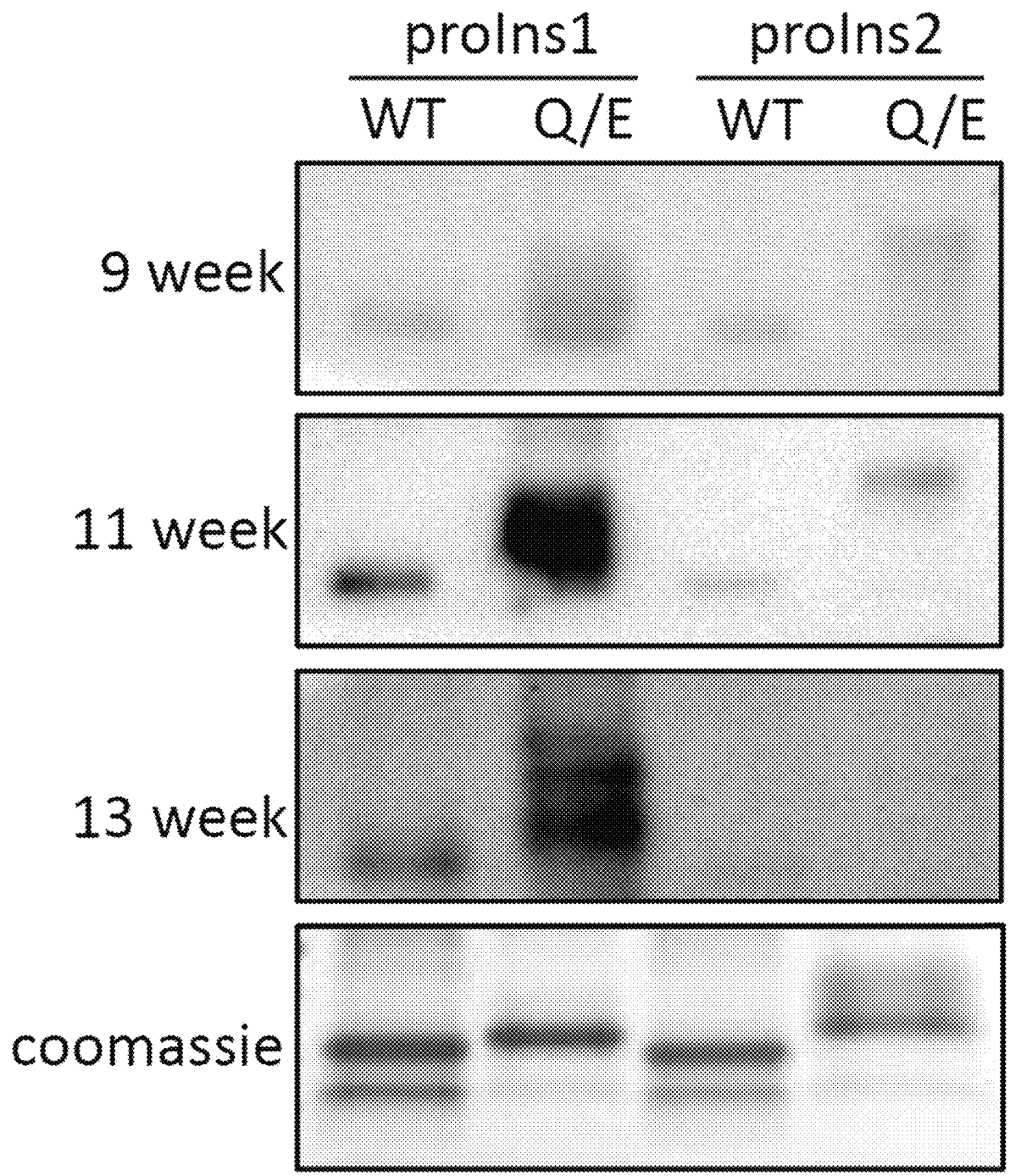
FIG. 7 depicts the results of a longitudinal study of an individual NOD mouse for serological activity towards proinsulin antigens, either of WT of deamidated (Q/E) forms. Strong immune reactivity was observed for proinsulin1, particularly for the deamidated antigen.
Figure 14:
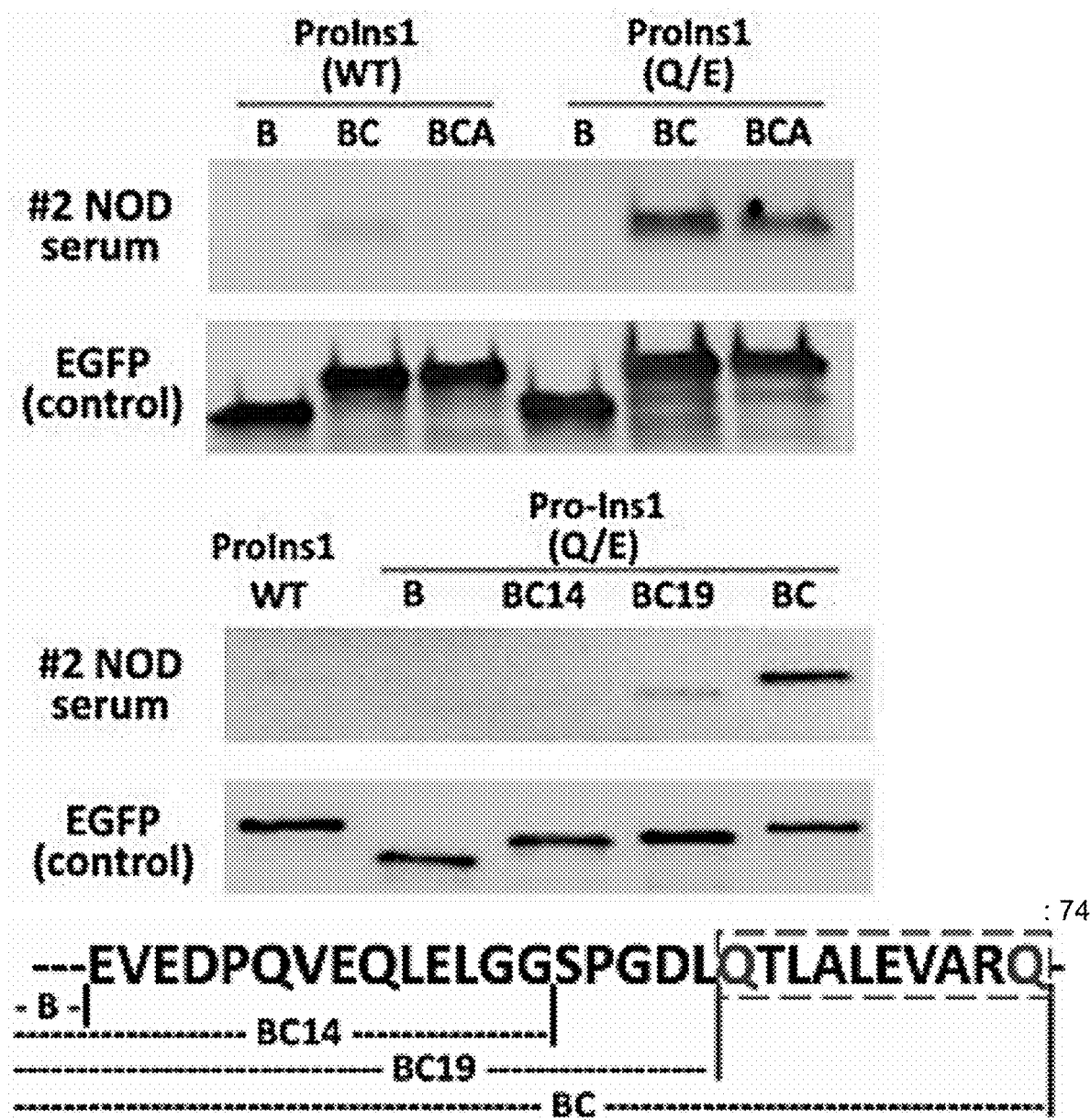
FIG. 14 shows epitope mapped to the C-peptide segment.
Figure 15:
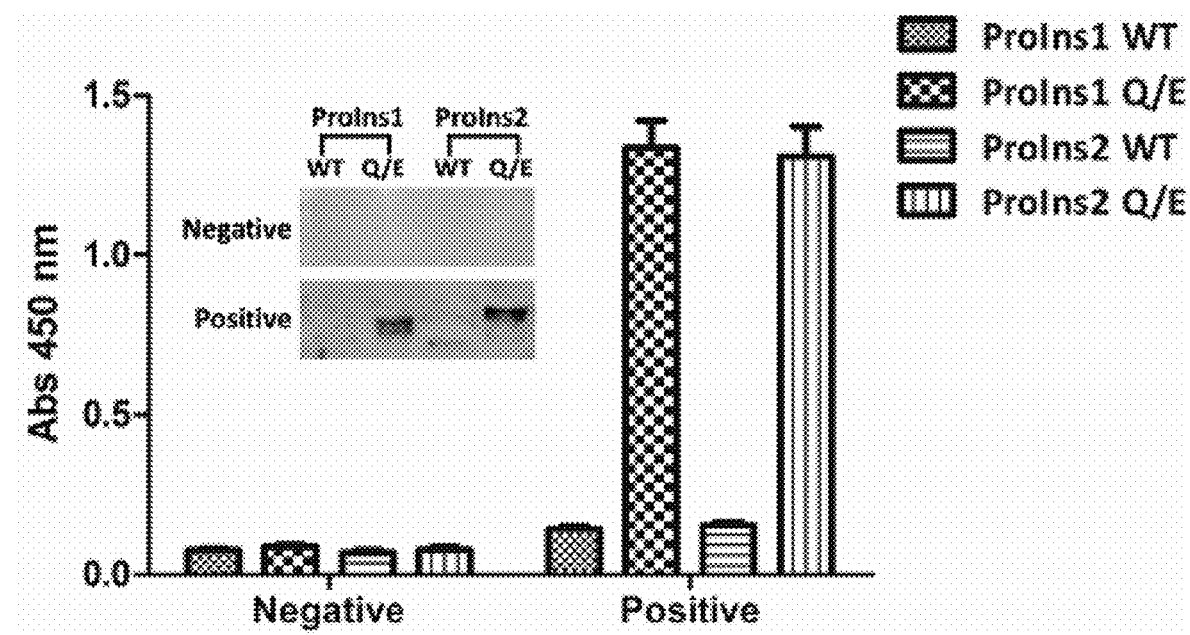
FIG. 15 shows a graph of results from custom ELISA for detecting autoantibodies to native (W) and deamidated (Q/E) proinsulin (Proins)-1&2. Deamidation-specific negative and positive sera from NOD mice confirmed by blotting (inset).
Figure 16:
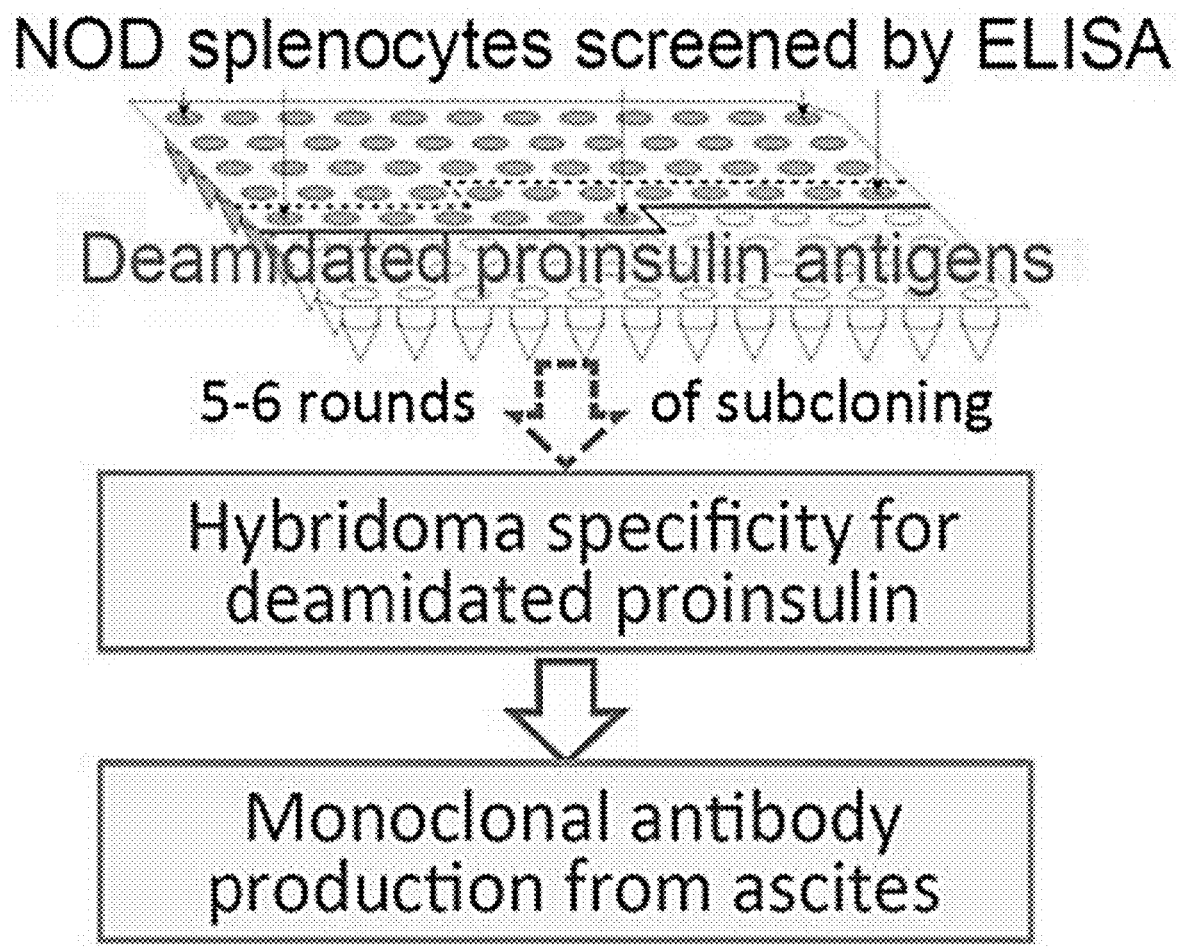
FIG. 16 shows a schematic representation of hybridoma screening.
Figure 17:
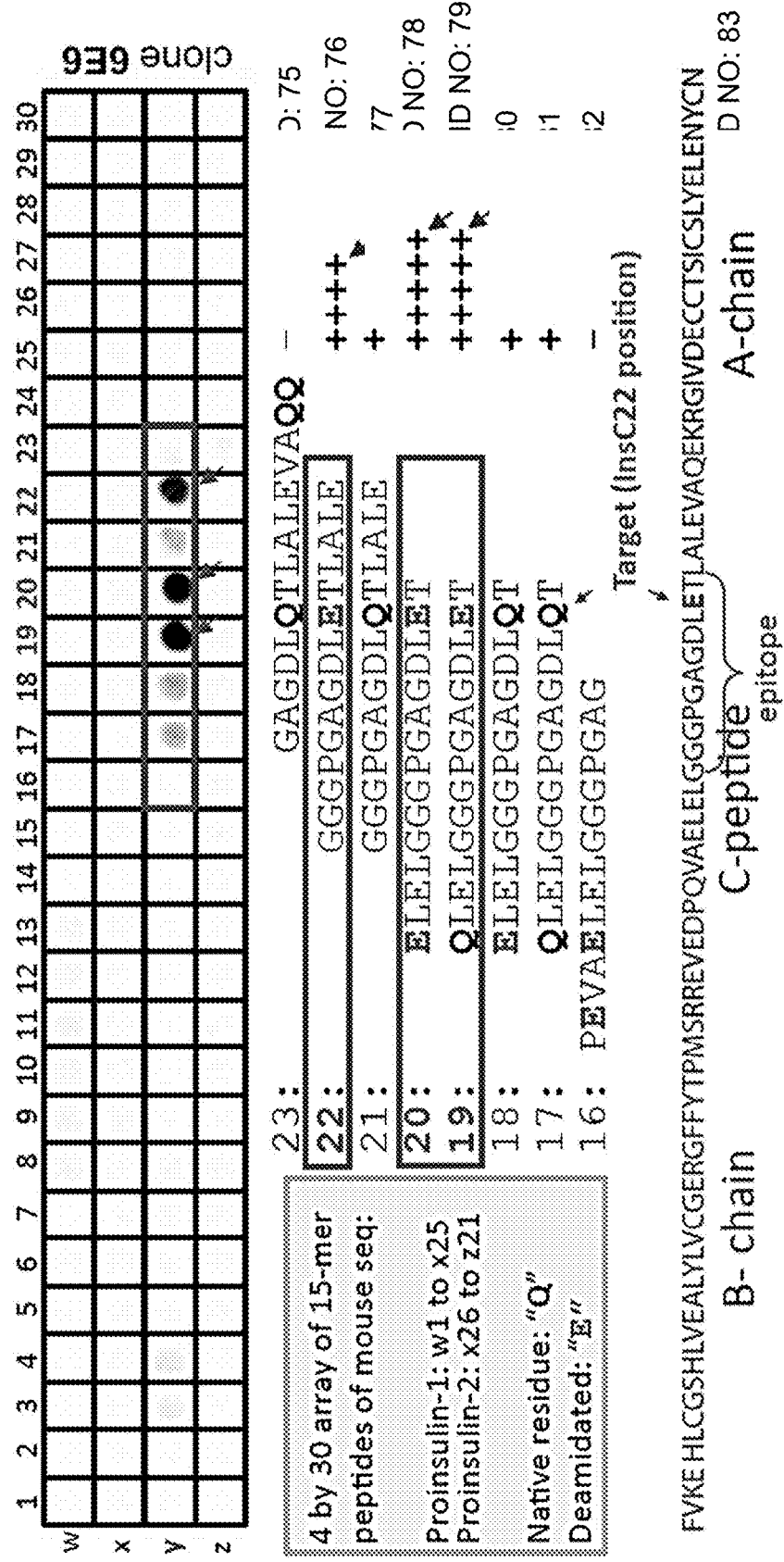
FIG. 17 shows identification of autoantibody epitope INSC22 by peptide array. A representative monoclonal antibody of clone 6E6 shows reactivity to deamidated (E at C-peptide residue 22: InsC22) proinsulin-2 peptides y19, y20 and y22. Peptides in their native sequences with Q residue at InsC22 are weak antigens (e.g., y17, y18, y21). Epitope location in mouse proinsulin-2 sequence is shown (bottom).
Figure 18:
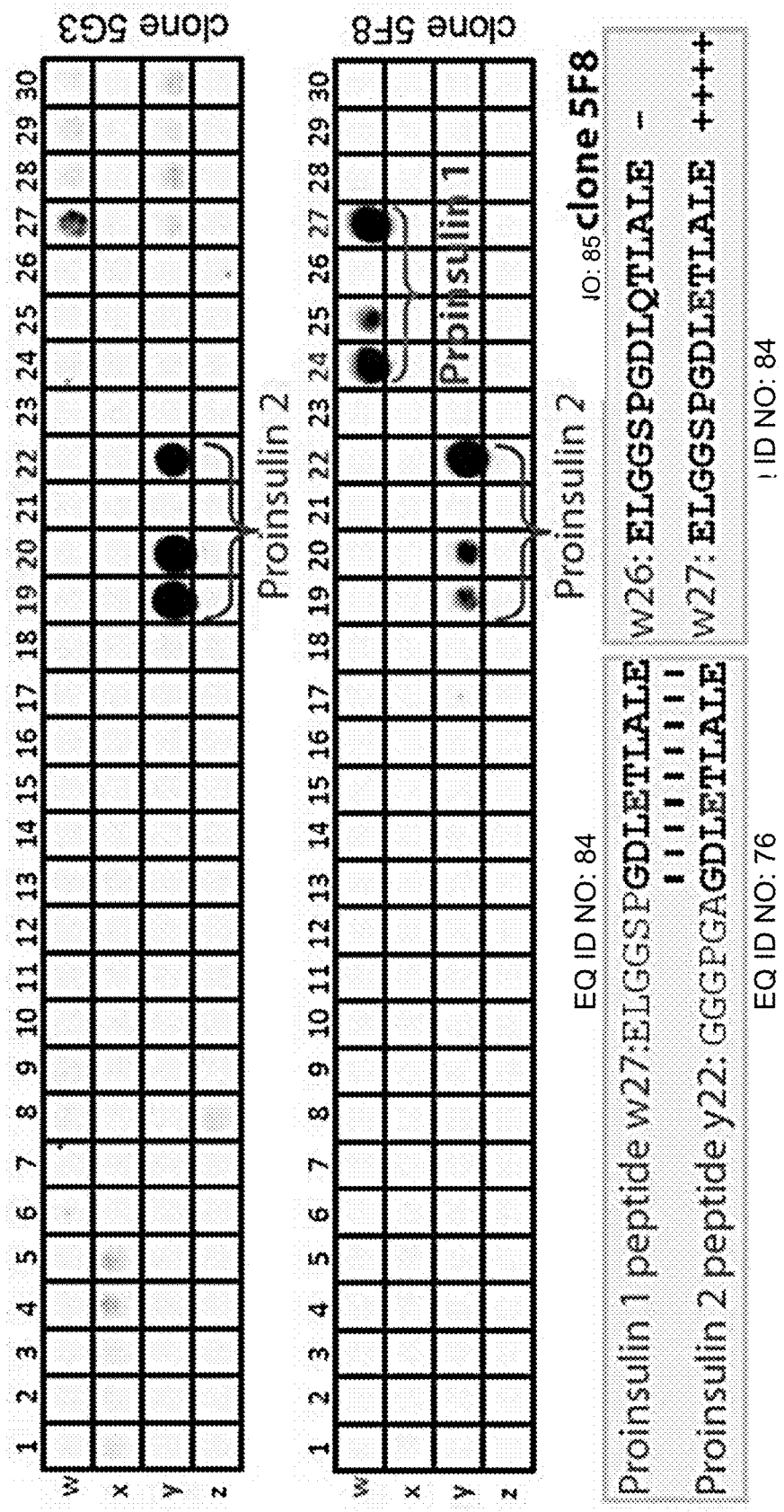
FIG. 18 shows representative examples from clones 5G3 and 5F8 demonstrating that all 16 hybridomas obtained and tested show autoantibody specificity for the same InsC22 of proinsulin.
Figure 19:
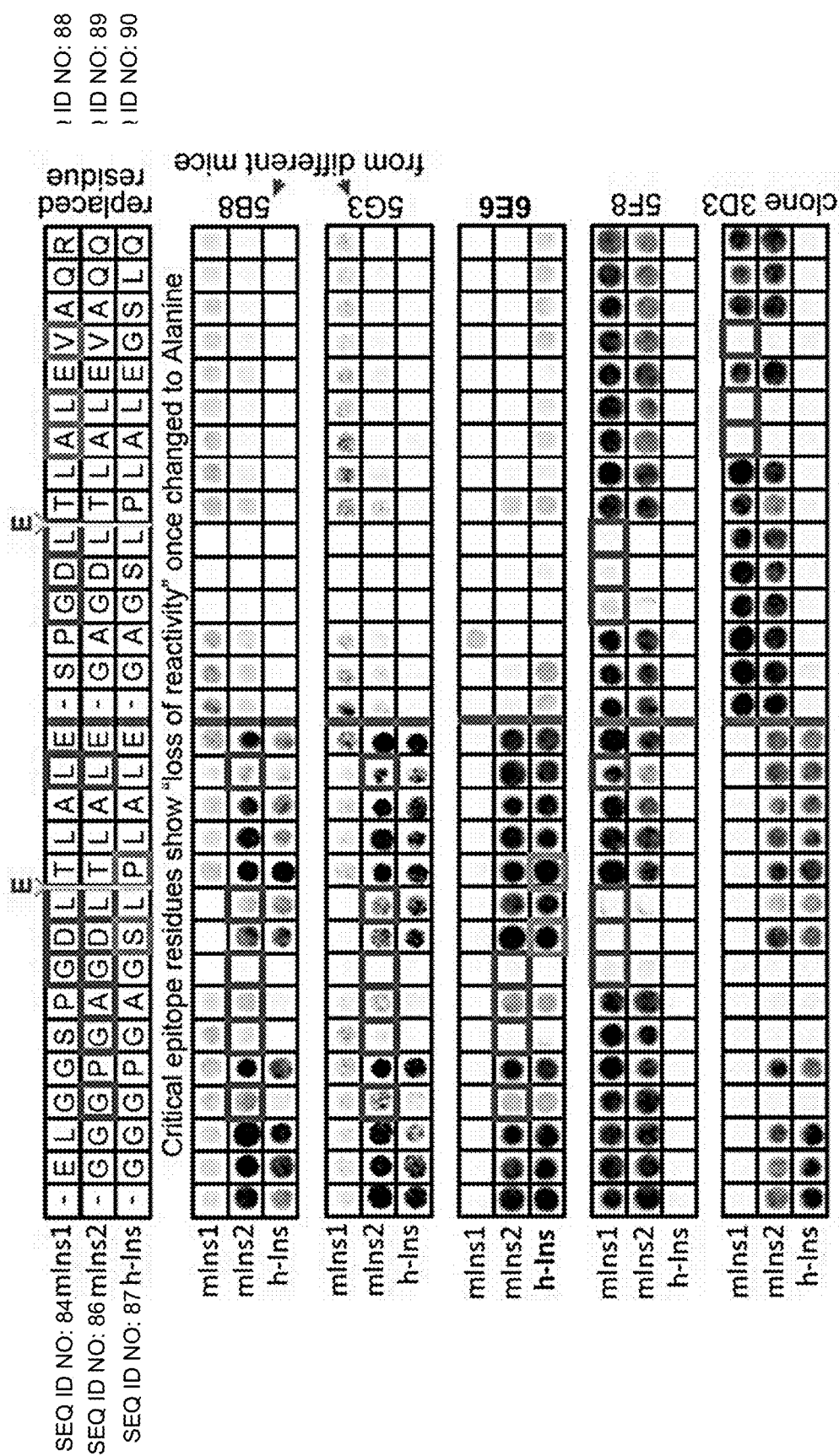
FIG. 19 shows shared autoantiobody specificity among clones 6E6, 5G3, and 5B8. Alanine scanning for autoantibody epitope specificity using a peptide array that only includes the sequence anchored to the deamidated InsC22 residue of mouse (mIns) and human (h-Ins) proinsulin sequences.
Figures 20, 21:
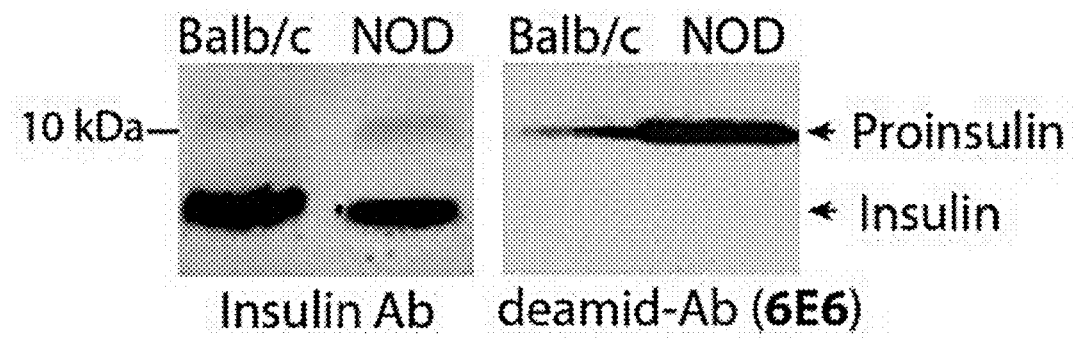
FIG. 20 shows deamidated proinsulin exists abundantly in pre-onset NOD islets.
FIG. 21 shows viral mimicry of the human deamidated (E) proinsulin epitope.
Figures 23, 24:
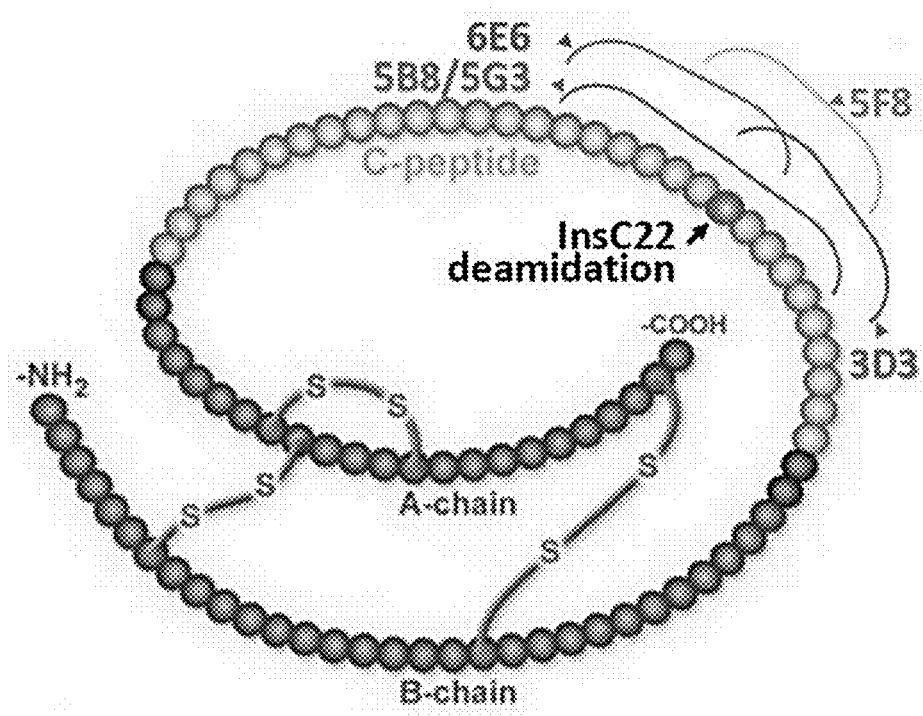
FIG. 23 shows a table depicting $V_L$ gene variants with similar CDR3L sequences.
FIG. 24 shows a schematic depicting the overlapping epitopes of exemplary antibodies, all anchored at InsC22.

To determine the class of modifications that contribute to neo-antigenecity in T1D patients, an approach of relating T1D to other auto-immune diseases, such as celiac disease, was followed. Celiac disease and T1D frequently exist concomitantly and they share common HLA iso-types—such as HLA-DQ2 and DQ8—in high-risk populations. In celiac, modification of wheat gluten (antigenicity through a 33 amino acid alpha-gliadin of gluten) through deamidation potentiates antigen presentation by HLA-DQ2/8 that has high affinities to deamidated peptide epitopes (FIGS. 2 and 3). By mass spectrometry, it was determined that deamidation is the most common modification of insulin (including pro-insulin) molecules (FIG. 4). IT was contemplated that deamidated insulin is a priming source of autoantigen in T1D among patients with the matching HLA-DQ2/8 genetic background. Immune-staining was performed for the major deamidation enzyme, transglutaminase (TG2, or tTG or TGase) in the pancreas. Strong TG2 expression was observed only in the delta cells in human islets (FIG. 5). Furthermore, in test tube, recombinant proinsulin protein was shown to be a substrate for TG2. Recombinant antigens of gluten/gliadin were then produced, as well as human proinsulin, in their native and deamidated forms. Experiments were conducted to measure serum antibody reactivity towards these antigens. 15 adult T1D patients were tested and 4 positive subjects were identified for deamidated gluten/gliadin and 1 positive for deamidated proinsulin (FIG. 6). No serum reactivity towards native insulin was found. Because the study subject have had no insulin production from their pancreas for a significant time, antibody responses were expected to be low and no longer relevant to disease progression. Therefore, the serum reactivity test was performed in a mouse model for T1D. Non-Obese Diabetic (NOD) mice that express an I-Ag7 class MHC were used as the functional equivalent of human HLA-DQ8. Strong antibody responses were identified, specifically against deamidated forms of pro-insulin in NOD mice (FIG. 14). Next experiments in a group of 17 NOD mice detected specific antibody reactivity towards deamidated proIns1 antigen in 3 animals (See, e.g., FIG. 7). Experiments demonstrated that humoral immunity correlates with diabetic onset (FIG. 15). These findings provide experimental evidence of neo-antigenicity in T1D towards a form of modified protein.

Example 2

Deamidation of Proinsulin and Antibodies in TD1 Patients and in NOD Mice

Figure 9:
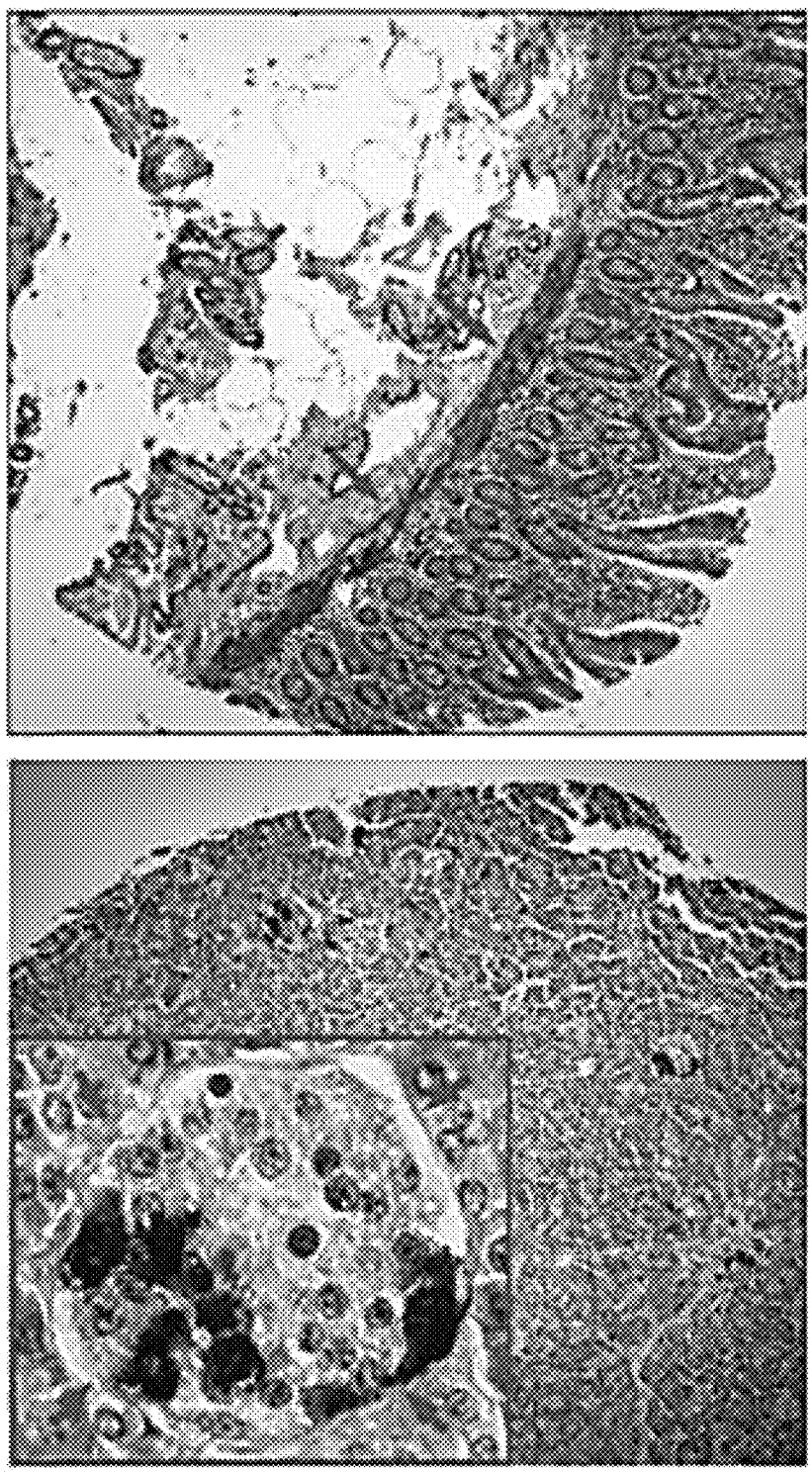
FIG. 9 shows images of immunohistochemistry of small intestine (upper) and pancrease (lower) demonstrating tTG expression in islets.

The deamidase tTG/TG2 is mainly expressed in the lamina propria of the small intestine (FIG. 9, upper), consistent with its pathogenic role in celiac disease. tTG expression was examined in human islets. Immunochemistry (IHC) of normal pancreas sections revealed that tTG was expressed in islet delta cells (FIG. 9, lower: inset showing high resolution of an islet—delta cell), but not in any exocrine cells.

Figure 10:
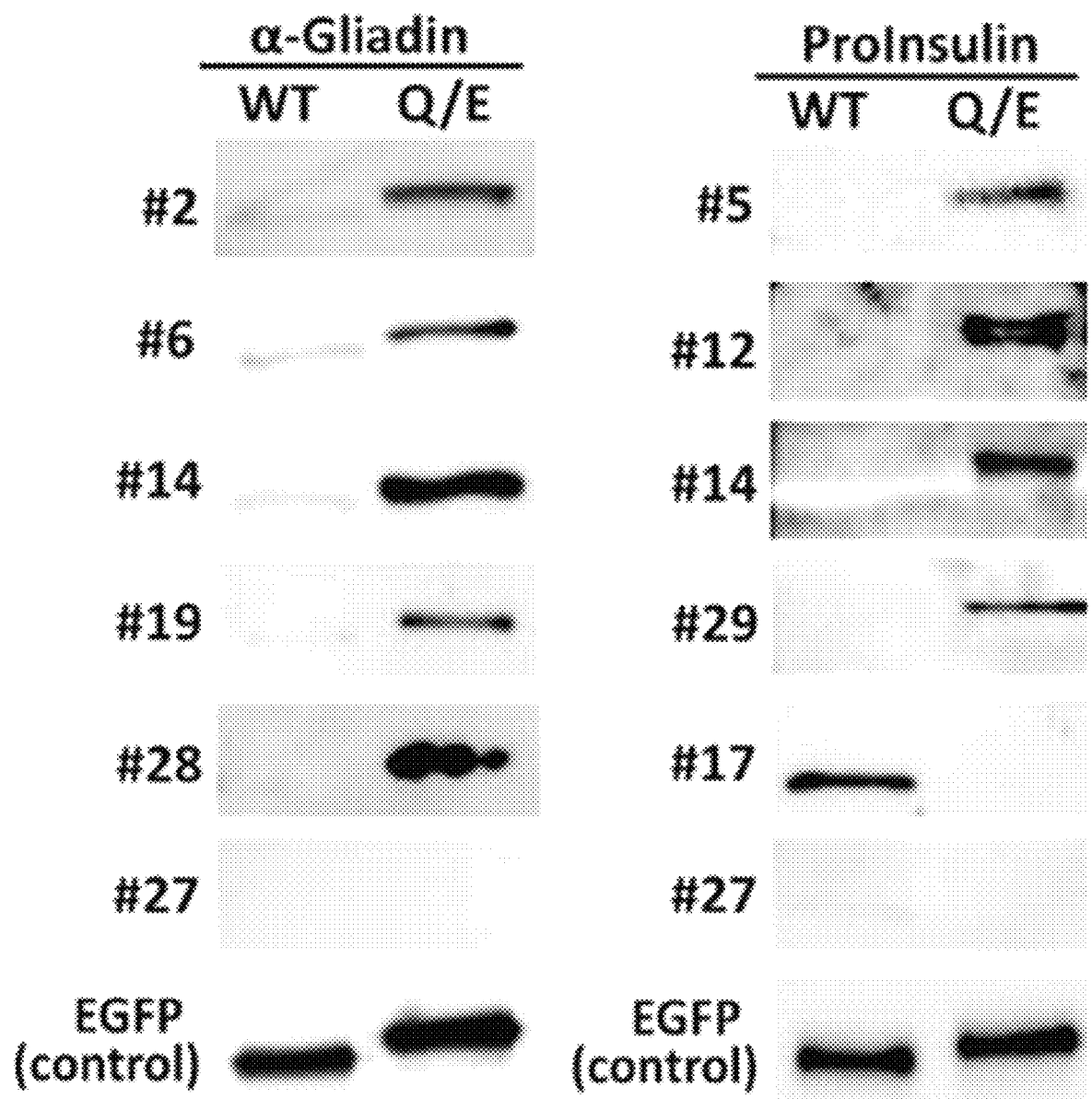
FIG. 10 shows detection of autoantibodies against deamidated proinsulin detected in T1D patients (#17 and #27 are controls).
Figure 11:
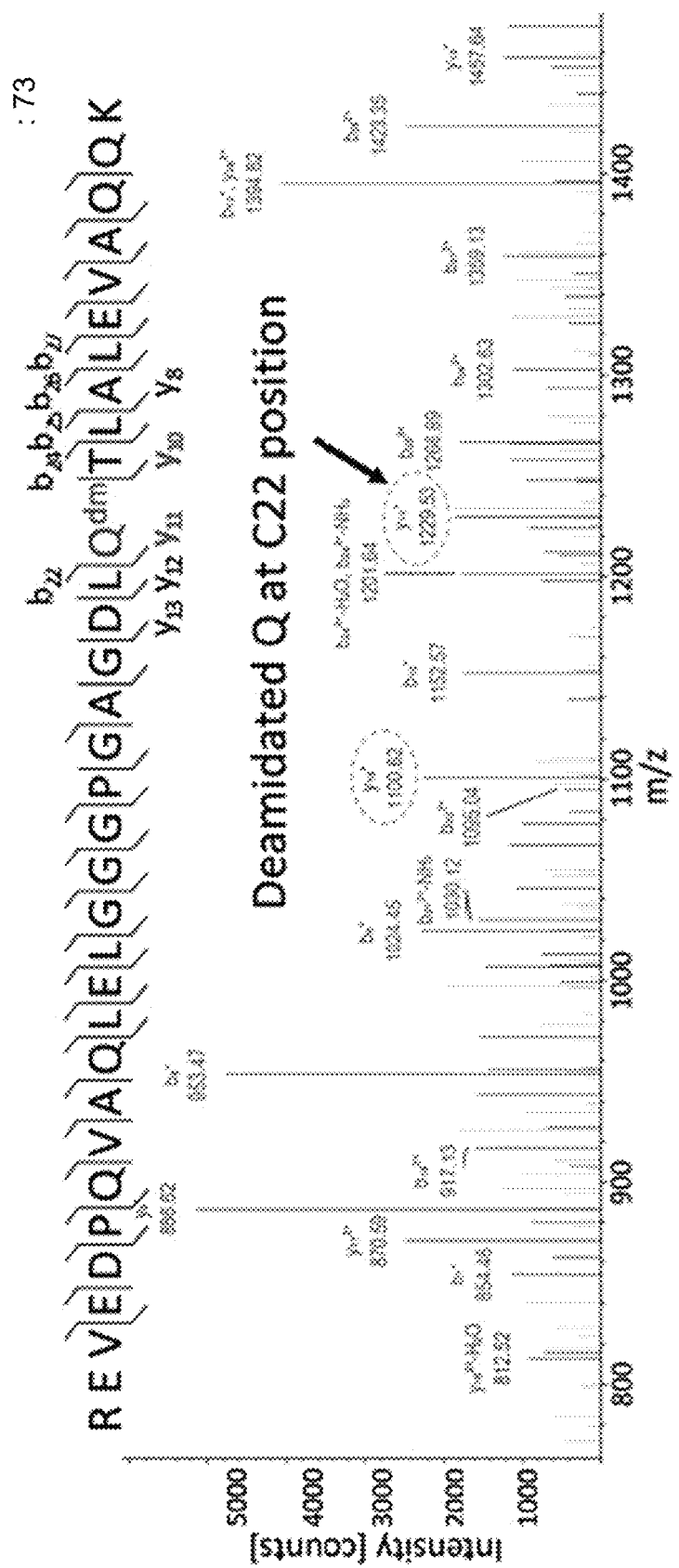
FIG. 11 show naturally-deamidated proinsulin detected by mass spectrometry from mouse islets. A representative MS2 spectrum shows deamidated proinsulin peptide from the C-peptide segment. Insulin and proinsulin were enriched from BalB/c islets. The Gln (Q) residue at InsC22 position is deamidated. The spectrum contains b- and y-series ions that match the deamidated peptide fragmentation pattern (top).
Figure 12:
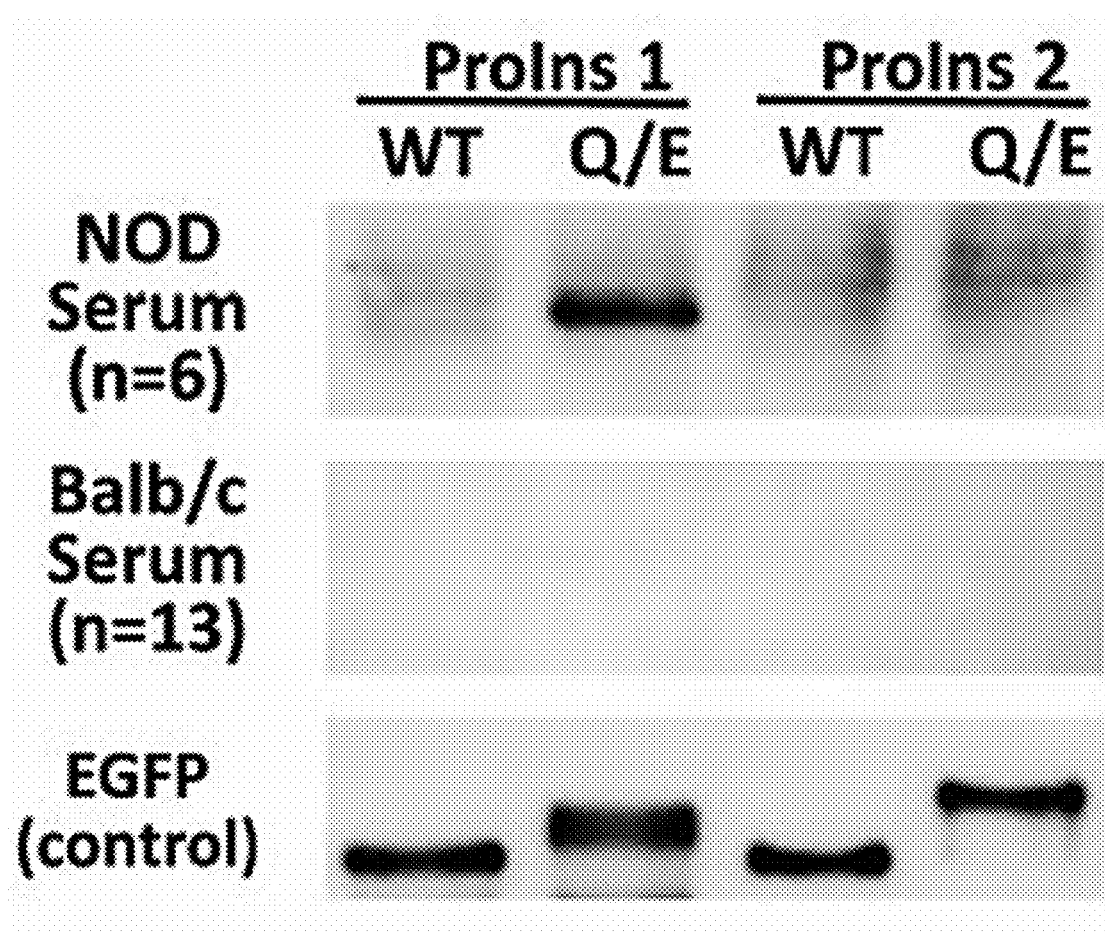
FIG. 12 shows autoantiobodies to deaminated (Q/E) pro-insulin-1 detected in NOD sera. Balb/c: control. EGFP-tagged WT and Q/E recombinant antigens.
Figure 13:
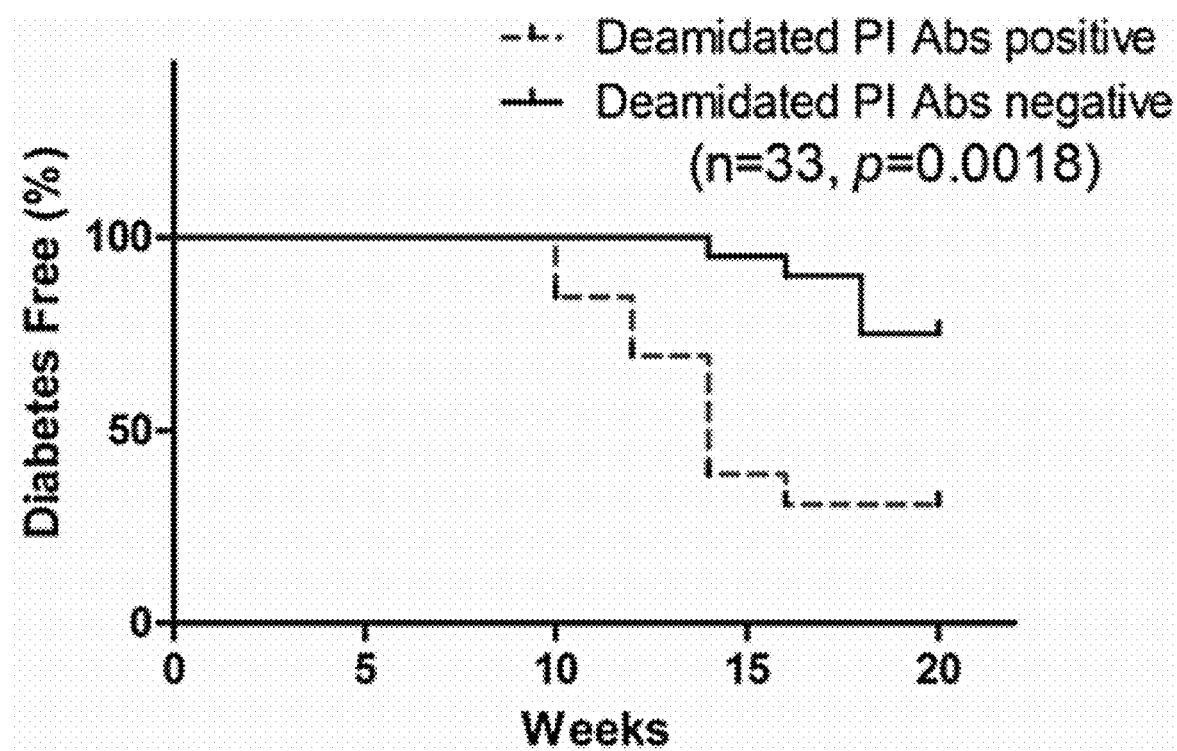
FIG. 13 shows Kaplan Meier disease-free curves for an NOD cohort with or without autoantibodies (Abs) for deamidated proinsulin.

Intracellular tTG lacks enzymatic activity. It was contemplated that secreted tTG encounters and modifies proinsulin released from damaged beta cells. Based on a computational model, it has been suggested that the InsB30-C13 peptide can be deamidated at two Qs. This deamidated peptide promotes cellular immunity, evidenced by IFN-γ production by T cells when stimulated with the modified peptide. To examine whether humoral immunity towards deamidated proinsulin also occurs in T1D, sera was collected from adult T1D patients, some of whom carried a concurrent diagnosis of celiac disease (CD). Proinsulin was produced as recombinant antigens, either in the native form or with six of the seven Qs substituted with their deamidated form of glutamic acid (E). As a positive control, an α-gliadin polypeptide (residues 57-89), the implicated antigen in CD, was also produced, in its native and deamidated forms. Out of the 30 T1D patient sera, 8 showed distinctive reactivity towards deamidated α-gliadin (See, e.g., FIG. 10). Certain subjects showed distinctive reactivity towards deamidated, but not native, proinsulin (FIG. 10, right). These results indicate antibody specificity for deamidated proinsulin is present in a subset of T1D patients. To determine if proinsulin deamidation naturally occurs in islets, islets were isolated from BALB/c mice and mass spectrometry (MS) was performed on islet proteins. Deamidated Qs (deamidated InsC22 residue is shown) on proinsulin could be identified by MS (FIG. 11).

The NOD model is a prototypical mouse model for human T1D. These mice express MEW II I-Ag7 that is similar to human HLA-DQ8 and preferentially binds to deamidated peptides. It was first tested whether sera from pre-diabetic female NOD mice showed reactivity to deamidated proinsulin. Pooled sera from six 10-week old NOD mice showed specific antibody reactivity to deamidated, but not native proinsulin-1 (FIG. 12). In contrast, no such antibody was detected in pooled BALB/c sera, as a normal control. A longitudinal study of individual serum reactivity was conducted in a female NOD cohort. Mice expressing autoantibodies to deamidated proinsulin antigens had a significantly higher incidence (p=0.0018) of diabetic onset (FIG. 13). The region for polyclonal antibody reactivity was mapped to the C-peptide segment (FIG. 14). An ELISA system utilizing the same recombinant native vs. deamidated proinsulin antigen demonstrated robust performance of ELISA (FIG. 15).

Example 3

Hybridomas that Produce T1D Autoantibodies

Unlike most T-cell receptors (TCR)s, biochemical tools for characterizing antibodies and B-cell receptor (BCR) specificity are available. In order to gain definitive insights into the antigen epitopes, including those that address the attributes of deamidated epitopes, individual B-lymphocytes were cloned. Hybridoma isolation was performed from a total of five NOD mice. Splenocytes were immortalized and antibody production was detected using aforementioned custom ELISA that simultaneously monitors four distinct antibodies, to proinsulin-1, 2, either in their native or deamidated forms (FIG. 15). In every 50,000,000 cells screened, each mouse had from 3 to 20 cells positive for either one of the four antibodies. Clones were selected with distinctive specificity for deamidated antigens. A 96-well method (FIG. 16) was used to do 5-6 rounds of clonal isolation (subcloning), and a total of 16 clones were obtained, each originating from a naturally formed disease cell that produces autoantibody towards deamidated proinsulin antigens (FIG. 15). The process was guided by ELISA readings to isolate clonal pure cells that were extremely rare (~1 in 10,000,000).

In order to accurately map the proinsulin epitopes for these monoclonal autoantibodies, arrays of peptides were made, each 15 amino acids in length, all derived from mouse proinsulin-1 and proinsulin-2 sequences in a "walking" pattern (peptides as a series of overlapping sequences as illustrated in FIG. 19, middle panel). The array was probed with individual antibodies. FIG. 19 shows a representative example of one antibody (from clone 6E6) having specificity toward a deamidated residue within the C-peptide segment of proinsulin-1—at the InsC22 position. Remarkably, all 16 clones across the 5 animals exhibited exclusive reactivity toward this deamidated InsC22 residues (two additional examples of are in FIG. 20), albeit with distinctive preferences either for proinsulin-1, proinsulin-2, or for both. Clone 5G3 (FIG. 20) has a similar specificity as 6E6 (FIG. 19), while 5F8 also cross-reacts with proinsulin-1 at the equivalent epitope (FIG. 20). Other clones recognized either the same epitope sequence or those from slightly shifted positions, however all still anchored at the deamidated InsC22 residue. The results are consistent with low-resolution mapping results from serum polyclonal antibodies in FIG. 17. Variable domain VH and VL sequences have been obtained from the 16 clones, including 13 complete sequences and 3 partial sequences for VH; and 15 complete sequences and 1 partial sequence for VL. Then it was determined that each clone is unique from one another in their antibody-encoding DNA sequences.

In order to further define epitope specificity for each clone at the amino acid level, an adapted a mutagenesis method was performed using another peptide array. The new array only included peptides that contain the deamidated InsC22 of mouse proinsulin-1, 2, and human proinsulin (FIG. 19). Each deamidated peptide then derived 14 variants (mutants), each carrying a single amino acid substitution of an individual residue with alanine. Once probed with a monoclonal antibody, mutations that abolish antibody binding are defined as a critical residue of the epitopes. Overall, there are various patterns of epitope attributes associated with individual antibodies (See, e.g., FIG. 19). Of particular interest, these results explain the reasons for proinsulin-1 and proinsulin-2 cross-reactivity (such as 5F8; FIG. 18), or lack of thereof (See, e.g., 6E6 and 5G3: FIGS. 17 and 18, respectively). Some clones, such as 6E6, cross-react with human proinsulin due to shared similarity between mouse proinsulin-2 and human proinsulin (FIG. 19, top panel). Consistent with the NOD cohort observation of autoantibody correlation with diabetic development, these NOD islets in pre-onset conditions have much higher levels of deamidated proinsulin production than BALB/c control (FIG. 20, right panel), as determined by antibody 6E6 that only recognizes the deamidated InsC22 epitope. Proinsulin constitutes a small fraction of the total insulin contents (FIG. 20, left panel: the upper bands compared to the lower bands of mature insulin), so proinsulin deamidation does not affect the production, processing or the function of hormone insulin (lower bands). Instead, it directly triggers autoantibody expression.

Example 4

A Viral Antigen Carries a Deamidation-Mimetic Epitope

Coxsackie viruses have been proposed to incite T1D based on an epidemic of Coxsackie B4 in the Bering Sea islands in 1967 (a viewpoint that has remained a subject of debate). The mapping of the precise epitope site for NOD autoantibodies herein, prompted further use of the human epitope sequence of "GPGAGSLE(/Q)PLALEG" SEQ ID NO: 112 to perform in silico search ("BLAST") for matching viral epitopes. Across the entire spectrum of viral families, Herpesviridae returned matches, and only to the query that used the deamidated but not the native proinsulin epitope. Representative examples are shown in FIG. 21. These viral sequences all have their natural E residue that mimics deamidation.

Example 5

VH and VL Gene Sequencing and Determination of Antibody Gene Bias

Experiments were conducted during development of embodiments herein to determine whether there is antibody gene basis for the natural propensity of autoantibodies to the deamidated epitope. In other words, during somatic V(D)J recombination of the antibody genes, whether or not the imparity in V-D-J cassette selections could be distinguished. Using a combination of strategies, we obtained the complete sequences of 13 heavy (VH) chains and 15 light (VL) chains out of the 16 clones across from 5 animals. Each gene has a distinct nucleotide sequence—no two clones share the same DNA sequence. However, clones with similar antibody specificity share great degrees of amino acid similarity. There is also a strong indication of cassette-directed specificity towards distinct epitopes, such as proinsulin1-alone vs.

proinsulin1&2 (FIG. 22). For example, 3 out of the 4 proinsulin-1-specific clones, each from a different mouse, share the exact VH and VL gene usage, or the gene type (FIG. 22). However variants of the same gene type may encode different acid sequences (See, e.g., 2), commonly due to natural process of gene permutation during plasma cell maturation. When the DNA sequences were subjected to a BLAST search against NCBI Non-redundant Dataset (Nr), a complete match was observed between the Vκ (encoding VL) of hybridoma clone 6E6 and a reported clone (H295: NCBI:gb|EU568281.1) that was isolated from islet-infiltrating B-lymphocyte of an NOD strain (NOD crossed to diabetogenic TCR 8.3)(32). Unlike isolations from precision cloning guided by antigen specificity using ELISA, this reported H295 clone was derived from a population of cells that was only physically present in the islets. This coincidental match of clonal VL gene sequences indicates that B-lymphocytes with BCR specificity to this deamidated proinsulin epitope of InsC22 can infiltrate diabetic islets, and it strongly suggests a mechanism for antigen-specific diabetogenesis, contrary to the viewpoint that autoantibodies (or BCRs for same matter) do not contribute to pathogenesis.

The invention claimed is:

1. A composition comprising a peptide or polypeptide comprising a sequence selected from SEQ ID NOs: 102 and 104-111 linked to a detectable label or attached to a solid surface.

2. The composition of claim 1, wherein the peptide or polypeptide comprises at least one Q to E substitution relative to SEQ ID NO: 2.

3. A method comprising contacting a composition of claim 1 with a sample from a subject and detecting the presence of antibodies in the sample that bind to the peptide or polypeptide.

4. A composition comprising a peptide or polypeptide consisting of SEQ ID NO: 101 linked to a detectable label or attached to a solid surface.

5. A composition comprising a peptide or polypeptide consisting of SEQ ID NO: 103 linked to a detectable label or attached to a solid surface.

* * * * *

SEQUENCE LISTING

```
<160> NUMBER OF SEQ ID NOS: 112

<210> SEQ ID NO 1
<211> LENGTH: 110
<212> TYPE: PRT
<213> ORGANISM: Homo sapiens

<400> SEQUENCE: 1

Met Ala Leu Trp Met Arg Leu Leu Pro Leu Leu Ala Leu Leu Ala Leu
1               5                   10                  15

Trp Gly Pro Asp Pro Ala Ala Phe Val Asn Gln His Leu Cys Gly
            20                  25                  30

Ser His Leu Val Glu Ala Leu Tyr Leu Val Cys Gly Glu Arg Gly Phe
                35                  40                  45

Phe Tyr Thr Pro Lys Thr Arg Arg Glu Ala Glu Asp Leu Gln Val Gly
            50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
                100                 105                 110

<210> SEQ ID NO 2
<211> LENGTH: 31
<212> TYPE: PRT
<213> ORGANISM: Homo sapiens

<400> SEQUENCE: 2

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 3
<211> LENGTH: 8
<212> TYPE: PRT
<213> ORGANISM: Mus musculus

<400> SEQUENCE: 3

Gly Ile Asp Phe Arg Arg Cys Trp
1               5

<210> SEQ ID NO 4
<211> LENGTH: 8
<212> TYPE: PRT
<213> ORGANISM: Mus musculus

<400> SEQUENCE: 4
```

```
Gly Tyr Thr Phe Thr Ser Tyr Trp
1               5
```

<210> SEQ ID NO 5
<211> LENGTH: 8
<212> TYPE: PRT
<213> ORGANISM: Mus musculus

<400> SEQUENCE: 5

```
Gly Phe Ser Leu Thr Ser Tyr Gly
1               5
```

<210> SEQ ID NO 6
<211> LENGTH: 8
<212> TYPE: PRT
<213> ORGANISM: Mus musculus

<400> SEQUENCE: 6

```
Gly Tyr Thr Phe Thr Asp Tyr Glu
1               5
```

<210> SEQ ID NO 7
<211> LENGTH: 8
<212> TYPE: PRT
<213> ORGANISM: Mus musculus

<400> SEQUENCE: 7

```
Ile Ile Pro Asp Ser Ser Thr Leu
1               5
```

<210> SEQ ID NO 8
<211> LENGTH: 8
<212> TYPE: PRT
<213> ORGANISM: Mus musculus

<400> SEQUENCE: 8

```
Ile Asn Pro Ser Asn Gly Gly Thr
1               5
```

<210> SEQ ID NO 9
<211> LENGTH: 7
<212> TYPE: PRT
<213> ORGANISM: Mus musculus

<400> SEQUENCE: 9

```
Ile Trp Ser Gly Gly Ser Thr
1               5
```

<210> SEQ ID NO 10
<211> LENGTH: 8
<212> TYPE: PRT
<213> ORGANISM: Mus musculus

<400> SEQUENCE: 10

```
Ile Asp Pro Ser Asp Ser Tyr Thr
1               5
```

<210> SEQ ID NO 11
<211> LENGTH: 8
<212> TYPE: PRT
<213> ORGANISM: Mus musculus

<400> SEQUENCE: 11

```
Ile Asp Pro Glu Thr Gly Gly Thr
1               5
```

<210> SEQ ID NO 12
<211> LENGTH: 8
<212> TYPE: PRT
<213> ORGANISM: Mus musculus

<400> SEQUENCE: 12

Ile Asp Pro Asn Ser Gly Gly Thr
1               5

<210> SEQ ID NO 13
<211> LENGTH: 13
<212> TYPE: PRT
<213> ORGANISM: Mus musculus

<400> SEQUENCE: 13

Ala Arg Cys Tyr Tyr Gly Ser Asn Tyr Ala Met Asp Tyr
1               5                   10

<210> SEQ ID NO 14
<211> LENGTH: 13
<212> TYPE: PRT
<213> ORGANISM: Mus musculus

<400> SEQUENCE: 14

Ala Arg Cys Ser Asn Ser Ile Phe Tyr Ala Met Asp Tyr
1               5                   10

<210> SEQ ID NO 15
<211> LENGTH: 13
<212> TYPE: PRT
<213> ORGANISM: Mus musculus

<400> SEQUENCE: 15

Ala Arg Ser Tyr Tyr Gly Asn Tyr Tyr Ala Met Asp Tyr
1               5                   10

<210> SEQ ID NO 16
<211> LENGTH: 11
<212> TYPE: PRT
<213> ORGANISM: Mus musculus

<400> SEQUENCE: 16

Ala Arg Ser Tyr Tyr Gly Ser Ser Tyr Ala Met
1               5                   10

<210> SEQ ID NO 17
<211> LENGTH: 9
<212> TYPE: PRT
<213> ORGANISM: Mus musculus

<400> SEQUENCE: 17

Ala Arg Asp Gly Tyr Gly Pro Asp Tyr
1               5

<210> SEQ ID NO 18
<211> LENGTH: 9
<212> TYPE: PRT
<213> ORGANISM: Mus musculus

<400> SEQUENCE: 18

Ala Arg Asp Gly Asn Ala Met Asp Tyr
1               5

```
<210> SEQ ID NO 19
<211> LENGTH: 5
<212> TYPE: PRT
<213> ORGANISM: Mus musculus

<400> SEQUENCE: 19

Ala Arg Pro Tyr Tyr
1               5

<210> SEQ ID NO 20
<211> LENGTH: 7
<212> TYPE: PRT
<213> ORGANISM: Mus musculus

<400> SEQUENCE: 20

Thr Leu Thr Gly Lys Gly Tyr
1               5

<210> SEQ ID NO 21
<211> LENGTH: 6
<212> TYPE: PRT
<213> ORGANISM: Mus musculus

<400> SEQUENCE: 21

Ala Ser Leu Phe Ala Tyr
1               5

<210> SEQ ID NO 22
<211> LENGTH: 10
<212> TYPE: PRT
<213> ORGANISM: Mus musculus

<400> SEQUENCE: 22

Lys Ser Val Ser Thr Ser Gly Tyr Ser Tyr
1               5                   10

<210> SEQ ID NO 23
<211> LENGTH: 12
<212> TYPE: PRT
<213> ORGANISM: Mus musculus

<400> SEQUENCE: 23

Gln Ser Leu Leu Asn Ser Arg Asn Gln Lys Asn Tyr
1               5                   10

<210> SEQ ID NO 24
<211> LENGTH: 11
<212> TYPE: PRT
<213> ORGANISM: Mus musculus

<400> SEQUENCE: 24

Gln Ser Leu Val His Ser Asn Gly Asn Thr Tyr
1               5                   10

<210> SEQ ID NO 25
<211> LENGTH: 11
<212> TYPE: PRT
<213> ORGANISM: Mus musculus

<400> SEQUENCE: 25

Gln Ser Leu Leu Tyr Ser Asp Gly Lys Thr Tyr
1               5                   10

<210> SEQ ID NO 26
<211> LENGTH: 11
```

```
<212> TYPE: PRT
<213> ORGANISM: Mus musculus

<400> SEQUENCE: 26

Gln Ser Leu Leu Tyr Ser Asn Gly Lys Thr Tyr
1               5                   10

<210> SEQ ID NO 27
<211> LENGTH: 3
<212> TYPE: PRT
<213> ORGANISM: Mus musculus

<400> SEQUENCE: 27

Leu Val Ser
1

<210> SEQ ID NO 28
<211> LENGTH: 3
<212> TYPE: PRT
<213> ORGANISM: Mus musculus

<400> SEQUENCE: 28

Gly Ala Ser
1

<210> SEQ ID NO 29
<211> LENGTH: 3
<212> TYPE: PRT
<213> ORGANISM: Mus musculus

<400> SEQUENCE: 29

Arg Val Ser
1

<210> SEQ ID NO 30
<211> LENGTH: 3
<212> TYPE: PRT
<213> ORGANISM: Mus musculus

<400> SEQUENCE: 30

Gln Val Ser
1

<210> SEQ ID NO 31
<211> LENGTH: 9
<212> TYPE: PRT
<213> ORGANISM: Mus musculus

<400> SEQUENCE: 31

Gln Asn Asp Tyr Ser Tyr Pro Phe Thr
1               5

<210> SEQ ID NO 32
<211> LENGTH: 9
<212> TYPE: PRT
<213> ORGANISM: Mus musculus

<400> SEQUENCE: 32

Gln Asn Asp Tyr Ser Tyr Pro Leu Thr
1               5

<210> SEQ ID NO 33
<211> LENGTH: 9
<212> TYPE: PRT
<213> ORGANISM: Mus musculus
```

<400> SEQUENCE: 33

Phe Gln Gly Thr His Val Pro Tyr Ala
1               5

<210> SEQ ID NO 34
<211> LENGTH: 9
<212> TYPE: PRT
<213> ORGANISM: Mus musculus

<400> SEQUENCE: 34

Phe Gln Gly Thr His Val Pro Tyr Thr
1               5

<210> SEQ ID NO 35
<211> LENGTH: 9
<212> TYPE: PRT
<213> ORGANISM: Mus musculus

<400> SEQUENCE: 35

Phe Gln Gly Thr His Val Pro Arg Thr
1               5

<210> SEQ ID NO 36
<211> LENGTH: 10
<212> TYPE: PRT
<213> ORGANISM: Mus musculus

<400> SEQUENCE: 36

Phe Gln Gly Thr His Val Pro Gln Leu Thr
1               5                   10

<210> SEQ ID NO 37
<211> LENGTH: 9
<212> TYPE: PRT
<213> ORGANISM: Mus musculus

<400> SEQUENCE: 37

Leu Gln Gly Thr Tyr Tyr Pro Tyr Thr
1               5

<210> SEQ ID NO 38
<211> LENGTH: 9
<212> TYPE: PRT
<213> ORGANISM: Mus musculus

<400> SEQUENCE: 38

Leu Gln Gly Thr Tyr Tyr Pro Gln Thr
1               5

<210> SEQ ID NO 39
<211> LENGTH: 410
<212> TYPE: DNA
<213> ORGANISM: Mus musculus

<400> SEQUENCE: 39

```
attgaggtca atctgcagga gtctgggagg ctagtctcag tttggtgccc ttgcctccca      60
cttcaatggc agttctttcc atttctccaa cgaagaggtg gaggtgcaac tgcaggagtc     120
aggaggtggc ctggtgcagc ctggaggatc cctgaaattc tcctgtgcag cctcaggaat     180
cgattttaga agatgctgga tgagttgggt tcggcgggct ccagggaaag gactcgaatg     240
gattggagaa attattccag atagcagtac attaaactat gcaccatctc taaggataa     300
```

| attcatcatc tccagagaca acgccaaaaa tacgctgtac ctgcaaatga gcaaagtgag | 360 |
| atctgaggac acagccctttt attactgtgt aagacctctg taatggttac | 410 |

<210> SEQ ID NO 40
<211> LENGTH: 360
<212> TYPE: DNA
<213> ORGANISM: Mus musculus

<400> SEQUENCE: 40

| gaggtccagc tgcaggagtc tgggactgaa ctggtgaagc ctggggcttc agtgaagctg | 60 |
| tcctgcaagg cttctggcta caccttcacc agctactgga tgcactgggt gaagcagagg | 120 |
| cctggacaag gccttgagtg gattggaaat attaatccta gcaatggtgg tactaactac | 180 |
| aatgagaagt tcaagagcaa ggccacactg actgtagaca atcctccag cacagcctac | 240 |
| atgcagctca gcagcctgac atctgaggac tctgcggtct attattgtgc aagatgttac | 300 |
| tacggtagta acatatgctat ggactactgg ggccaaggga ccaccgtcac cgtctcctca | 360 |

<210> SEQ ID NO 41
<211> LENGTH: 360
<212> TYPE: DNA
<213> ORGANISM: Mus musculus

<400> SEQUENCE: 41

| gaggtcaagc tgcaggagtc agggactgaa ctggtgaagc ctggggcttc agtgaagctg | 60 |
| tcctgcaagg cttctggcta caccttcacc agctactgga tgcactgggt gaagcagagg | 120 |
| cctggacaag gccttgagtg gattggaaat attaatccta gcaatggtgg tactaactac | 180 |
| aatgagaagt tcaagagcaa ggccacactg actgtagaca aatcctccag cacagcctac | 240 |
| atgcagctca gcagcctgac atctgaggac tctgcggtct attattgtgc aagatgtagt | 300 |
| aactctatat tctatgctat ggactactgg ggccaaggga ccaccgtcac cgtctcctca | 360 |

<210> SEQ ID NO 42
<211> LENGTH: 360
<212> TYPE: DNA
<213> ORGANISM: Mus musculus

<400> SEQUENCE: 42

| gaggtgaaac tgcagcagtc tgggactgaa ctggtgaagc ctggggcttc agtgaagctg | 60 |
| tcctgcaagg cttctggcta caccttcacc agctactgga tgcactgggt gaagcagagg | 120 |
| cctggacaag gccttgagtg gattggaaat attaatccta gcaatggtgg tactaactac | 180 |
| aatgagaagt tcaagagcaa ggccacactg actgtagaca atcctccag cacagcctac | 240 |
| atgcagctca gcagcctgac atctgaggac tctgcggtct attattgtgc aagatcctac | 300 |
| tatggtaact actatgctat ggactactgg ggccaaggga ccaccgtcac cgtctcctca | 360 |

<210> SEQ ID NO 43
<211> LENGTH: 315
<212> TYPE: DNA
<213> ORGANISM: Mus musculus

<400> SEQUENCE: 43

| ctgcaggagt cagggactga actggtgaag cctggggctt cagtgaagct gtcctgcaag | 60 |
| gcttctggct acaccttcac cagctactgg atgcactggg tgaagcagag gcctggacaa | 120 |
| ggccttgagt ggattggaaa tattaatcct agcaatggtg gtactaacta caatgagaag | 180 |
| ttcaagagca aggccacact gactgtagac aaatcctcca gcacagccta catgcagctc | 240 | agcagcctga catctgagga ctctgcggtc tattattgtg caagatctta ctacggtagt    300 agctatgcta tgact                                                    315

<210> SEQ ID NO 44
<211> LENGTH: 348
<212> TYPE: DNA
<213> ORGANISM: Mus musculus

<400> SEQUENCE: 44
gaggtcaaac tgcagcagtc tggacctggc ctagtgcagc cctcacagag cctgtccatc    60
acctgcacag tctctggttt ctcattaact agctatggtg tacactgggt tcgccagtct   120
ccaggaaagg gtctggagtg gctgggagtg atatggagtg gtggaagcac agactataat   180
gcagctttca tatccagact gagcatcagc aaggacaatt ccaagagcca agttttcttt   240
aaaatgaaca gtctgcaagc tgatgacaca gccatatatt acgccctatg gtaactagtt   300
ctatgctatg gactactggg gccaagggac caccgtcacc gtctcctc                348

<210> SEQ ID NO 45
<211> LENGTH: 344
<212> TYPE: DNA
<213> ORGANISM: Mus musculus

<400> SEQUENCE: 45
gaggtccagc tgcaggagtc tggacctggc ctagtgcagc cctcacagag cctgtccatc    60
acctgcacag tctctggttt ctcattaact agctatggtg tacactgggt tcgccagtct   120
ccaggaaagg gtctggagtg gctgggagtg atatggagtg gtggaagcac agactataat   180
gcagctttca tatccagact gagcatcagc aaggacaatt ccaagagcca agttttcttt   240
aaaatgaaca gtctgcaagc tgatgacaca gccatatatt actgtgccag agacgggtat   300
ggtcctgact actggggcca agggaccacc gtcaccgtct cctc                    344

<210> SEQ ID NO 46
<211> LENGTH: 345
<212> TYPE: DNA
<213> ORGANISM: Mus musculus

<400> SEQUENCE: 46
gaggtccagc tgcaggagtc tggacctggc ctagtgcagc cctcacagag cctgtccatc    60
acctgcacag tctctggttt ctcattaact agctatggtg tacactgggt tcgccagtct   120
ccaggaaagg gtctggagtg gctgggagtg atatggagtg gtggaagcac agactataat   180
gcagctttca tatccagact gagcatcagc aaggacaatt ccaagagcca agttttcttt   240
aaaatgaaca gtctgcaagc tgatgacaca gccatatatt actgtgccag agacgggtat   300
ggtcctgact actggggcca agggaccacc gtcaccgtct cctca                   345

<210> SEQ ID NO 47
<211> LENGTH: 345
<212> TYPE: DNA
<213> ORGANISM: Mus musculus

<400> SEQUENCE: 47
gaggtccagc tgcaggagtc aggacctggc ctagtgcagc cctcacagag cctgtccatc    60
acctgcacag tctctggttt ctcattaact agctatggtg tacactgggt tcgccagtct   120
ccaggaaagg gtctggagtg gctgggagtg atatggagtg gtggaagcac agactataat   180

```
gcagctttca tatccagact gagcatcagc aaggacaatt ccaagagcca agttttcttt      240
aaaatgaaca gtctgcaagc tgatgacaca gccatatatt actgtgccag agacgggtat      300
ggtcctgact actggggcca aggaccacc gtcaccgtct cctca                      345
```

<210> SEQ ID NO 48
<211> LENGTH: 301
<212> TYPE: DNA
<213> ORGANISM: Mus musculus

<400> SEQUENCE: 48

```
aggtgaaggc gcaggagtca ggacctggcc tagtgcagcc ctcacagagc ctgtccatca      60
cctgcacagt ctctggtttc tcattaacta gctatggtgt acactgggtt cgccagtctc     120
caggaaaggg tctggagtgg ctgggagtga tatggagtgg tggaagcaca gactataatg     180
cagctttcat atccagactg agcatcagca aggacaattc caagagccaa gttttcttta     240
aaatgaacag tctgcaagct gatgacacag ccatatatta ctgtgccaga gatggtaatg     300
c                                                                     301
```

<210> SEQ ID NO 49
<211> LENGTH: 303
<212> TYPE: DNA
<213> ORGANISM: Mus musculus

<400> SEQUENCE: 49

```
aggtgaaggc gcaggagtca ggacctggcc tagtgcagcc ctcacagagc ctgtccatca      60
cctgcacagt ctctggtttc tcattaacta gctatggtgt acactgggtt cgccagtctc     120
caggaaaggg tctggagtgg ctgggagtga tatggagtgg tggaagcaca gactataatg     180
cagctttcat atccagactg agcatcagca aggacaattc caagagccaa gttttcttta     240
aaatgaacag tctgcaagct gatgacacag ccatatatta ctgtgccaga gacgggtatg     300
tct                                                                   303
```

<210> SEQ ID NO 50
<211> LENGTH: 286
<212> TYPE: DNA
<213> ORGANISM: Mus musculus

<400> SEQUENCE: 50

```
gcaggagtca ggggctgagc ttgtgaagcc tggggcttca gtgaagctgt cctgcaaggc      60
ttctggctac accttcacca gctactggat gcagtgggta aaacagaggc ctggacaggg     120
ccttgagtgg atcggagaga ttgatccttc tgatagctat actaactaca atcaaaagtt     180
caagggcaag gccacattga ctgtagacac atcctccagc acagcctaca tgcagctcag     240
cagcctgaca tctgaggact ctgcggtcta ttactgtgca agccta                    286
```

<210> SEQ ID NO 51
<211> LENGTH: 302
<212> TYPE: DNA
<213> ORGANISM: Mus musculus

<400> SEQUENCE: 51

```
ttgaggtgaa ggcgcagcag tcaggggctg agctggtgag gcctggggct tcagtgacgc      60
tgtcctgcaa ggcttcgggc tacacattta ctgactatga aatgcactgg gtgaagcaga     120
cacctgtgca tggcctggaa tggattggag ctattgatcc tgaaactggt ggtactgcct     180
acaatcagaa gttcaagggc aaggccatac tgactgcaga caaatcctcc agcacagcct     240
```
acatggagct ccgcagcctg acatctgagg actctgccgt ctattactgt acctaactga   300
ag   302

<210> SEQ ID NO 52
<211> LENGTH: 353
<212> TYPE: DNA
<213> ORGANISM: Mus musculus

<400> SEQUENCE: 52
gaggtcaaac tgcaggagtc aggaggtggc ctggtgcagc ctggaggatc cctgaaactc    60
tcctgtgcag cctcaggatt cgattttagt aaagactgga tgagttgggt ccggcaggct   120
acagggaaag gctagaatg aattggagaa attaatccag gtagcagtac gataaactat   180
actccatctc taaaggataa attcatcatc tccagagaca cgccaaaaa tacgctgtac   240 ctgcaaatga gcaaagtgag atctgaggac acagcccttt attactgtgc aagacctcac   300
cacggtggta cttcgatgtc tggggccaag ggaccaccgt caccgtctcc tca   353

<210> SEQ ID NO 53
<211> LENGTH: 344
<212> TYPE: DNA
<213> ORGANISM: Mus musculus

<400> SEQUENCE: 53
gaggtcaaac tgcaggagtc tggacctggc ctagtgcagc cctcacagag cctgtccatc    60
acctgcacag tctctggttt ctcattaact agctatggtg tacactgggt tcgccagtct   120
ccaggaaagg gtctggagtg gctgggagtg atatggagtg gtggaagcac agactataat   180
gcagctttca tatccagact gagcatcagc aaggacaatt ccaagagcca agttttcttt   240
aaaatgaaca gtctgcaagc tgatgacaca gccatatatt actgtgccag agacgggtat   300
ggtcctgact actggggcca aggaccacc gtcaccgtct cctc   344

<210> SEQ ID NO 54
<211> LENGTH: 299
<212> TYPE: DNA
<213> ORGANISM: Mus musculus

<400> SEQUENCE: 54
tgtaggtgaa ggcgcaggag tcaggggctg agcttgtgaa gcctggggct tcagtgaagc    60
tgtcctgcaa ggcttctggc tacaccttca ccagctactg gatgcactgg gtgaagcaga   120
ggcctggacg aggccttgag tggattggaa ggattgatcc taatagtggt ggtactaagt   180
acaatgagaa gttcaagagc aaggccacac tgactgtaga caaaccctcc agcacagcct   240
acatgcagct cagcagcctg acatctgagg actctgcggt ctattatgtg caagttgtg   299

<210> SEQ ID NO 55
<211> LENGTH: 381
<212> TYPE: DNA
<213> ORGANISM: Mus musculus

<400> SEQUENCE: 55
ctttgatatt gtgatgacgc aggctttatt gaggaagtga cagatgattc cagatttag    60 atctgtgtat tgtggaagac gcaggctcct gcttccttag ctgtatctct ggggcagagg   120
gccaccatct catacagggc cagcaaaagt gtcagtacat ctggctatag ttatatgcac   180
tggaaccaac agaaaccagg acagccaccc agactcctca tctatcttgt atccaaccta   240

```
gaatctgggg tccctgccag gttcagtggc agtgggtctg ggacagactt caccctcaac      300
atccatcctg tggaggagga ggatgctgca acctattact gtcagcacat tagggagctt      360
acacgttcgg aggtggacca a                                                 381

<210> SEQ ID NO 56
<211> LENGTH: 366
<212> TYPE: DNA
<213> ORGANISM: Mus musculus

<400> SEQUENCE: 56
gatattgtga tgacgcaggc tccatcctcc ctgagtgtgt cagcaggaga taaggtcact       60
atgagctgca agtccagtca gagtctgtta aacagtagaa accaaaagaa ctacttggcc      120
tggtaccagc agaaaccatg gcagcctcct aaactgctga tctacggggc atccactagg      180
gaatctgggg tccctgatcg cttcacaggc agtggatctg gaacagattt cactctcacc      240
atcagcagtg tgcaggctga agacctggca gtttattact gtcagaatga ttatagttat      300
ccatttacgt tcggcacggg gacaaaattg gaaataaaac gggctgatgc tgcaccaact      360
gtatcc                                                                  366

<210> SEQ ID NO 57
<211> LENGTH: 366
<212> TYPE: DNA
<213> ORGANISM: Mus musculus

<400> SEQUENCE: 57
gatattgtga tgacgcaggc tccatcctcc ctgagtgtgt cagcaggaga taaggtcact       60
atgagctgca agtccagtca gagtctgtta aacagtagaa accaaaagaa ctacttggcc      120
tggtaccagc agaaaccatg gcagcctcct aaactgctga tctacggggc atccactagg      180
gaatctgggg tccctgatcg cttcacaggc agtggatctg gaacagattt cactctcacc      240
atcagcagtg tgcaggctga agacctggca gtttattact gtcagaatga ttatagttat      300
ccattcacgt tcggcacggg gacaaaattg gaaataaaac gggctgatgc tgcaccaact      360
gtatcc                                                                  366

<210> SEQ ID NO 58
<211> LENGTH: 321
<212> TYPE: DNA
<213> ORGANISM: Mus musculus

<400> SEQUENCE: 58
ggagataggt cactatgagc tgcaagtcca gtcagagtct gttaaacagt agaaaccaaa       60
agaactactt ggcctggtac cagcagaaac catggcagcc tcctaaactg ctgatctacg      120
gggcatccac tagggaatct ggggtccctg atcgcttcac aggcagtgga tctggaacag      180
atttcactct caccatcagc agtgtgcagg ctgaagacct ggcagtttat tactgtcaga      240
atgattatag ttatccattc acgttcggca cggggacaaa attggaaata aaacgggctg      300
atgctgcacc aactgtatcc a                                                 321

<210> SEQ ID NO 59
<211> LENGTH: 318
<212> TYPE: DNA
<213> ORGANISM: Mus musculus

<400> SEQUENCE: 59
tgatattgtg atgacgcagg ctccatcctc cctgagtgtg tcagcaggag ataaggtcac       60
```

```
tatgagctgc aagtccagtc agagtctgtt aaacagtaga aaccaaaaga actacttggc    120
ctggtaccag cagaaaccat ggcagcctcc taaactgctg atctacgggg catccactag    180
ggaatctggg gtccctgatc gcttcacagg cagtggatct ggaacagatt tcactctcac    240
catcagcagt gtgcaggctg aagacctggc agtttattac tgtcagaatg attatagtta    300
tccatcacgt cggcacgg                                                   318
```

<210> SEQ ID NO 60
<211> LENGTH: 366
<212> TYPE: DNA
<213> ORGANISM: Mus musculus

<400> SEQUENCE: 60

```
gatattgtga tgacgcaggc tccatcctcc ctgagtgtgt cagcaggaga taaggtcact     60
atgagctgca agtccagtca gagtctgtta aacagtagaa accaaaagaa ctacttggcc    120
tggtaccagc agaaaccatg gcagcctcct aaactgctga tctacggggc atccactagg    180
gaatctgggg tccctgatcg cttcacaggc agtggatctg aacagatttc actctcacc    240 atcagcagtg tgcaggctga agacctggca gtttattact gtcagaatga ttatagttat    300
cctctcacgt tcggtgctgg gaccaagctg gagctgaaac gggctgatgc tgcaccaact    360
gtatcc                                                               366
```

<210> SEQ ID NO 61
<211> LENGTH: 363
<212> TYPE: DNA
<213> ORGANISM: Mus musculus

<400> SEQUENCE: 61

```
gatattgtga tgacgcaggc tccactctcc ctgcctgtca gtcttggaga tcaagcttcc     60
atctcttgca gatctagtca gagccttgta cacagcaatg aaacaccta tttatattgg    120 tacctgcaga agccaggcca gtctccaaag ctcctgatct acagggtttc caaccgattt    180
tctggggtcc cagacaggtt cagtggcagt ggatcaggga cagatttcac actcaagatc    240
agcagagtgg aggctgagga tctggagtt tatttctgct ttcaaggtac acatgttccg    300
tatgcgttcg gatcggggac caagctggaa ataaaacggg ctgatgctgc accaactgta    360
tcc                                                                  363
```

<210> SEQ ID NO 62
<211> LENGTH: 321
<212> TYPE: DNA
<213> ORGANISM: Mus musculus

<400> SEQUENCE: 62

```
cttggagatc agcttccatc tcttgcagat ctagtcagag ccttgtacac agcaatggaa     60
acacctattt atattggtac ctgcagaagc caggccagtc tccaaagctc ctgatctaca    120
gggtttccaa ccgatttct ggggtcccag acaggttcag tggcagtgga tcagggacag    180
atttcacact caagatcagc agagtggagg ctgaggatct gggagtttat ttctgctttc    240
aaggtacaca tgttccgtat acgttcggat cggggaccaa gctggaaata aaacgggctg    300
atgctgcaca aactgtatcc a                                              321
```

<210> SEQ ID NO 63
<211> LENGTH: 363
<212> TYPE: DNA

<213> ORGANISM: Mus musculus

<400> SEQUENCE: 63

| | |
|---|---|
| gatattgtga tgacgcaggc tccactctcc ctgcctgtca gtcttggaga tcaagcttcc | 60 |
| atctcttgca gatctagtca gagccttgta cacagcaatg gaaacaccta tttatattgg | 120 |
| tacctgcaga agccaggcca gtctccaaag ctcctgatct acagggtttc aaccgatttt | 180 |
| tctggggtcc cagacaggtt cagtggcagt ggatcaggga cagatttcac actcaagatc | 240 |
| agcagagtgg aggctgagga tctggagtt tatttctgct ttcaaggtac acatgttcct | 300 |
| cggacgttcg gtggaggcac caagctggaa atcaaacggg ctgatgctgc accaactgta | 360 |
| tcc | 363 |

<210> SEQ ID NO 64
<211> LENGTH: 332
<212> TYPE: DNA
<213> ORGANISM: Mus musculus

<400> SEQUENCE: 64

| | |
|---|---|
| ttgatattgt ggagacgcag gctccactct ccctgcctgt cagtcttgga gatcaagctt | 60 |
| ccatctcttg cagatctagt cagagccttg tacacagcaa tggaaacacc tatttatatt | 120 |
| ggtacctgca aagccaggc cagtctccaa agctcctgat ctacagggtt tccaaccgat | 180 |
| tttctggggt cccagacagg ttcagtggca gtggatcagg acagatttc acactcaaga | 240 |
| tcagcagagt ggaggctgag gatctggag tttatttctg ctttcaaggt acacatgttc | 300 |
| ctcagctcac gttcggtgct ggaccaagct ag | 332 |

<210> SEQ ID NO 65
<211> LENGTH: 326
<212> TYPE: DNA
<213> ORGANISM: Mus musculus

<400> SEQUENCE: 65

| | |
|---|---|
| ttgatattgt ggagacgcag gctccactct ccctgcctgt cagtcttgga gatcaagctt | 60 |
| ccatctcttg cagatctagt cagagccttg tacacagcaa tggaaacacc tatttatatt | 120 |
| ggtacctgca aagccaggc cagtctccaa agctcctgat ctacagggtt tccaaccgat | 180 |
| tttctggggt cccagacagg ttcagtggca gtggatcagg acagatttc acactcaaga | 240 |
| tcagcagagt ggaggctgag gatctggag tttatttctg ctttcaaggt acacatgttc | 300 |
| cgtatacgtt cggatcggga ccaagc | 326 |

<210> SEQ ID NO 66
<211> LENGTH: 316
<212> TYPE: DNA
<213> ORGANISM: Mus musculus

<400> SEQUENCE: 66

| | |
|---|---|
| tgatattgtg gagacgcag gctccactct ccctgcctgt cagtcttgga gatcaagctt | 60 |
| ccatctcttg cagatctagt cagagccttg tacacagcaa tggaaacacc tatttatatt | 120 |
| ggtacctgca aagccaggc cagtctccaa agctcctgat ctacagggtt tccaaccgat | 180 |
| tttctggggt cccagacagg ttcagtggca gtggatcagg acagatttc acactcaaga | 240 |
| tcagcagagt ggaggctgag gatctggag tttatttctg ctttcaaggt acacatgttc | 300 |
| cgtatacgtc ggatcg | 316 |

<210> SEQ ID NO 67
<211> LENGTH: 318
<212> TYPE: DNA
<213> ORGANISM: Mus musculus

<400> SEQUENCE: 67

```
tgatattttg agacgcaggc tccactctcc ctgcctgtca gtcttggaga tcaagcttcc      60
atctcttgca gatctagtca gagccttgta cacagcaatg gaaacaccta tttatattgg     120
tacctgcaga agccaggcca gtctccaaag ctcctgatct acagggtttc caaccgattt     180
tctggggtcc cagacaggtt cagtggcagt ggatcaggga cagatttcac actcaagatc     240
agcagagtgg aggctgagga tctgggagtt tatttctgct ttcaaggtac acatgttcct     300
catacgtcgg atcgggac                                                   318
```

<210> SEQ ID NO 68
<211> LENGTH: 363
<212> TYPE: DNA
<213> ORGANISM: Mus musculus

<400> SEQUENCE: 68

```
gatattgtga tgacgcaggc tccactctcc ctgcctgtca gtcttggaga tcaagcttcc      60
atctcttgca gatctagtca gagccttgta cacagcaatg gaaacaccta tttatattgg     120
tacctgcaga agccaggcca gtctccaaag ctcctgatct acagggtttc caaccgattt     180
tctggggtcc cagacaggtt cagtggcagt ggatcaggga cagatttcac actcaagatc     240
agcagagtgg aggctgagga tctgggagtt tatttctgct ttcaaggtac acatgttccg     300
tatacgttcg gatcggggac caagctggaa ataaaacggg ctgatgctgc accaactgta     360
tcc                                                                   363
```

<210> SEQ ID NO 69
<211> LENGTH: 363
<212> TYPE: DNA
<213> ORGANISM: Mus musculus

<400> SEQUENCE: 69

```
gatattgtga tgacgcaggc tccactgtct ttgtcggtta ccattggaca accagcctct      60
atctcttgca agtcaagtca gagcctctta tatagtgatg gaaagacata tttgaattgg     120
ttacaacaga ggccaggcca gtctccaaag cgcctaatgt atcaggtgtc caaactggac     180
cctggcatcc ctgacaggtt cagtggcagt ggatcagaga cagattttac acttaaaatc     240
agcagagtgg aggctgagga tttgggagtt tattactgct tgcaaggtac atattatccg     300
tatacgttcg gatcggggac caagctggaa ataaaacggg ctgatgctgc accaactgta     360
tcc                                                                   363
```

<210> SEQ ID NO 70
<211> LENGTH: 318
<212> TYPE: DNA
<213> ORGANISM: Mus musculus

<400> SEQUENCE: 70

```
tgatattgtg aagacgcag gctccactgt ctttgtcggt taccattgga caaccagcct       60
ctatctcttg caagtcaagt cagagcctct tatatagtga tggaaagaca tatttgaatt     120
ggttacaaca gaggccaggc cagtctccaa agcgcctaat gtatcaggtg tccaaactgg     180
accctggcat ccctgacagg ttcagtggca gtggatcaga gacagatttt acacttaaaa     240
```

```
tcagcagagt ggaggctgag gatttgggag tttattactg cttgcaaggt acatattatc    300
ctcagacgtt cggtgagc                                                  318
```

<210> SEQ ID NO 71
<211> LENGTH: 7
<212> TYPE: PRT
<213> ORGANISM: Artificial sequence
<220> FEATURE:
<223> OTHER INFORMATION: Dietary gluten

<400> SEQUENCE: 71

Tyr Pro Leu Gln Pro Gln Pro
1               5

<210> SEQ ID NO 72
<211> LENGTH: 7
<212> TYPE: PRT
<213> ORGANISM: Artificial sequence
<220> FEATURE:
<223> OTHER INFORMATION: Dietary gluten

<400> SEQUENCE: 72

Tyr Pro Leu Glu Pro Glu Pro
1               5

<210> SEQ ID NO 73
<211> LENGTH: 33
<212> TYPE: PRT
<213> ORGANISM: Mus musculus

<400> SEQUENCE: 73

Arg Glu Val Glu Asp Pro Gln Val Ala Gln Leu Glu Leu Gly Gly Gly
1               5                   10                  15

Pro Gly Ala Gly Asp Leu Gln Thr Leu Ala Leu Glu Val Ala Gln Gln
            20                  25                  30

Lys

<210> SEQ ID NO 74
<211> LENGTH: 29
<212> TYPE: PRT
<213> ORGANISM: Mus musculus

<400> SEQUENCE: 74

Glu Val Glu Asp Pro Gln Val Glu Gln Leu Glu Leu Gly Gly Ser Pro
1               5                   10                  15

Gly Asp Leu Gln Thr Leu Ala Leu Glu Val Ala Arg Gln
            20                  25

<210> SEQ ID NO 75
<211> LENGTH: 15
<212> TYPE: PRT
<213> ORGANISM: Mus musculus

<400> SEQUENCE: 75

Gly Ala Gly Asp Leu Gln Thr Leu Ala Leu Glu Val Ala Gln Gln
1               5                   10                  15

<210> SEQ ID NO 76
<211> LENGTH: 15
<212> TYPE: PRT
<213> ORGANISM: Mus musculus

<400> SEQUENCE: 76

-continued

Gly Gly Gly Pro Gly Ala Gly Asp Leu Glu Thr Leu Ala Leu Glu
1               5                   10                  15

<210> SEQ ID NO 77
<211> LENGTH: 15
<212> TYPE: PRT
<213> ORGANISM: Mus musculus

<400> SEQUENCE: 77

Gly Gly Gly Pro Gly Ala Gly Asp Leu Gln Thr Leu Ala Leu Glu
1               5                   10                  15

<210> SEQ ID NO 78
<211> LENGTH: 15
<212> TYPE: PRT
<213> ORGANISM: Mus musculus

<400> SEQUENCE: 78

Glu Leu Glu Leu Gly Gly Gly Pro Gly Ala Gly Asp Leu Glu Thr
1               5                   10                  15

<210> SEQ ID NO 79
<211> LENGTH: 15
<212> TYPE: PRT
<213> ORGANISM: Mus musculus

<400> SEQUENCE: 79

Gln Leu Glu Leu Gly Gly Gly Pro Gly Ala Gly Asp Leu Glu Thr
1               5                   10                  15

<210> SEQ ID NO 80
<211> LENGTH: 15
<212> TYPE: PRT
<213> ORGANISM: Mus musculus

<400> SEQUENCE: 80

Glu Leu Glu Leu Gly Gly Gly Pro Gly Ala Gly Asp Leu Gln Thr
1               5                   10                  15

<210> SEQ ID NO 81
<211> LENGTH: 15
<212> TYPE: PRT
<213> ORGANISM: Mus musculus

<400> SEQUENCE: 81

Gln Leu Glu Leu Gly Gly Gly Pro Gly Ala Gly Asp Leu Gln Thr
1               5                   10                  15

<210> SEQ ID NO 82
<211> LENGTH: 15
<212> TYPE: PRT
<213> ORGANISM: Mus musculus

<400> SEQUENCE: 82

Pro Glu Val Ala Glu Leu Glu Leu Gly Gly Gly Pro Gly Ala Gly
1               5                   10                  15

<210> SEQ ID NO 83
<211> LENGTH: 86
<212> TYPE: PRT
<213> ORGANISM: Mus musculus

<400> SEQUENCE: 83

Phe Val Lys Glu His Leu Cys Gly Ser His Leu Val Glu Ala Leu Tyr
1               5                   10                  15

```
Leu Val Cys Gly Glu Phe Gly Phe Phe Tyr Thr Pro Met Ser Arg Arg
            20                  25                  30

Glu Val Glu Asp Pro Gln Val Ala Glu Leu Glu Leu Gly Gly Pro
            35                  40                  45

Gly Ala Gly Asp Leu Thr Leu Ala Leu Glu Val Ala Gly Glu Lys
 50                  55                  60

Arg Gly Ile Val Asp Glu Cys Cys Thr Ser Ile Cys Ser Leu Tyr Glu
 65                  70                  75                  80

Leu Glu Asn Tyr Cys Asn
                85
```

<210> SEQ ID NO 84
<211> LENGTH: 15
<212> TYPE: PRT
<213> ORGANISM: Mus musculus

<400> SEQUENCE: 84

```
Glu Leu Gly Gly Ser Pro Gly Asp Leu Glu Thr Leu Ala Leu Glu
 1               5                  10                  15
```

<210> SEQ ID NO 85
<211> LENGTH: 15
<212> TYPE: PRT
<213> ORGANISM: Mus musculus

<400> SEQUENCE: 85

```
Glu Leu Gly Gly Ser Pro Gly Asp Leu Gln Thr Leu Ala Leu Glu
 1               5                  10                  15
```

<210> SEQ ID NO 86
<211> LENGTH: 14
<212> TYPE: PRT
<213> ORGANISM: Mus musculus

<400> SEQUENCE: 86

```
Gly Gly Gly Pro Gly Ala Gly Asp Leu Thr Leu Ala Leu Glu
 1               5                  10
```

<210> SEQ ID NO 87
<211> LENGTH: 14
<212> TYPE: PRT
<213> ORGANISM: Homo spaiens

<400> SEQUENCE: 87

```
Gly Gly Gly Pro Gly Ala Gly Ser Leu Pro Leu Ala Leu Glu
 1               5                  10
```

<210> SEQ ID NO 88
<211> LENGTH: 14
<212> TYPE: PRT
<213> ORGANISM: Mus musculus

<400> SEQUENCE: 88

```
Ser Pro Gly Asp Leu Thr Leu Ala Leu Glu Val Ala Gln Arg
 1               5                  10
```

<210> SEQ ID NO 89
<211> LENGTH: 14
<212> TYPE: PRT
<213> ORGANISM: Mus musculus

<400> SEQUENCE: 89

Gly Ala Gly Asp Leu Thr Leu Ala Leu Glu Val Ala Gln Gln
1               5                   10

<210> SEQ ID NO 90
<211> LENGTH: 14
<212> TYPE: PRT
<213> ORGANISM: Homo spaiens

<400> SEQUENCE: 90

Gly Ala Gly Ser Leu Pro Leu Ala Leu Glu Gly Ser Leu Gln
1               5                   10

<210> SEQ ID NO 91
<211> LENGTH: 10
<212> TYPE: PRT
<213> ORGANISM: Homo spaiens

<400> SEQUENCE: 91

Gly Pro Gly Ala Gly Ser Leu Glu Pro Leu
1               5                   10

<210> SEQ ID NO 92
<211> LENGTH: 8
<212> TYPE: PRT
<213> ORGANISM: Herpes virus

<400> SEQUENCE: 92

Pro Gly Ala Gly Ala Val Glu Pro
1               5

<210> SEQ ID NO 93
<211> LENGTH: 8
<212> TYPE: PRT
<213> ORGANISM: Herpes virus

<400> SEQUENCE: 93

Pro Gly Ala Cys Ala Leu Glu Pro
1               5

<210> SEQ ID NO 94
<211> LENGTH: 8
<212> TYPE: PRT
<213> ORGANISM: Herpes virus

<400> SEQUENCE: 94

Pro Gly Ala Gly Ala Pro Glu Pro
1               5

<210> SEQ ID NO 95
<211> LENGTH: 8
<212> TYPE: PRT
<213> ORGANISM: Herpes virus

<400> SEQUENCE: 95

Pro Gly Ala Gly Gly Pro Glu Pro
1               5

<210> SEQ ID NO 96
<211> LENGTH: 10
<212> TYPE: PRT
<213> ORGANISM: Herpes virus

<400> SEQUENCE: 96

Gly Ala Gly Ala Gly Glu Gly Glu Pro Leu
1               5                   10

<210> SEQ ID NO 97
<211> LENGTH: 9
<212> TYPE: PRT
<213> ORGANISM: Mus musculus

<400> SEQUENCE: 97

Phe Gln Gly Thr His Val Pro Tyr Ala
1               5

<210> SEQ ID NO 98
<211> LENGTH: 9
<212> TYPE: PRT
<213> ORGANISM: Mus musculus

<400> SEQUENCE: 98

Phe Gln Gly Thr His Val Pro Tyr Thr
1               5

<210> SEQ ID NO 99
<211> LENGTH: 9
<212> TYPE: PRT
<213> ORGANISM: Mus musculus

<400> SEQUENCE: 99

Phe Gln Gly Thr His Val Pro Arg Ala
1               5

<210> SEQ ID NO 100
<211> LENGTH: 86
<212> TYPE: PRT
<213> ORGANISM: Mus musculus

<400> SEQUENCE: 100

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Met Ser Arg Arg
            20                  25                  30

Glu Val Glu Asp Pro Gln Val Ala Gln Leu Glu Leu Gly Gly Gly Pro
        35                  40                  45

Gly Ala Gly Asp Leu Gln Thr Leu Ala Leu Glu Val Ala Gln Gln Lys
    50                  55                  60

Arg Gly Ile Val Asp Gln Cys Cys Thr Ser Ile Cys Ser Leu Tyr Gln
65                  70                  75                  80

Leu Glu Asn Tyr Cys Asn
                85

<210> SEQ ID NO 101
<211> LENGTH: 31
<212> TYPE: PRT
<213> ORGANISM: Homo spaiens

<400> SEQUENCE: 101

Glu Ala Glu Asp Leu Gln Val Gly Gln Val Glu Leu Gly Gly Gly Pro
1               5                   10                  15

Gly Ala Gly Ser Leu Glu Pro Leu Ala Leu Glu Gly Ser Leu Gln
            20                  25                  30

<210> SEQ ID NO 102
<211> LENGTH: 31
<212> TYPE: PRT
<213> ORGANISM: Homo spaiens -continued

```
<400> SEQUENCE: 102

Glu Ala Glu Asp Leu Glu Val Gly Gln Val Leu Gly Gly Gly Pro
1               5                   10                  15

Gly Ala Gly Ser Leu Gln Pro Leu Ala Leu Glu Gly Ser Leu Gln
                20                  25                  30

<210> SEQ ID NO 103
<211> LENGTH: 31
<212> TYPE: PRT
<213> ORGANISM: Homo spaiens

<400> SEQUENCE: 103

Glu Ala Glu Asp Leu Gln Val Gly Glu Val Leu Gly Gly Gly Pro
1               5                   10                  15

Gly Ala Gly Ser Leu Gln Pro Leu Ala Leu Gly Gly Ser Leu Gln
                20                  25                  30

<210> SEQ ID NO 104
<211> LENGTH: 31
<212> TYPE: PRT
<213> ORGANISM: Homo spaiens

<400> SEQUENCE: 104

Glu Ala Glu Asp Leu Gln Val Gly Gln Val Glu Leu Gly Gly Pro
1               5                   10                  15

Gly Ala Gly Ser Leu Gln Pro Leu Ala Leu Glu Gly Ser Leu Glu
                20                  25                  30

<210> SEQ ID NO 105
<211> LENGTH: 31
<212> TYPE: PRT
<213> ORGANISM: Homo spaiens

<400> SEQUENCE: 105

Glu Ala Glu Asp Leu Glu Val Gly Gln Val Leu Gly Gly Gly Pro
1               5                   10                  15

Gly Ala Gly Ser Leu Glu Pro Leu Ala Leu Glu Gly Ser Leu Gln
                20                  25                  30

<210> SEQ ID NO 106
<211> LENGTH: 31
<212> TYPE: PRT
<213> ORGANISM: Homo spaiens

<400> SEQUENCE: 106

Glu Ala Glu Asp Leu Gln Val Gly Glu Val Glu Leu Gly Gly Pro
1               5                   10                  15

Gly Ala Gly Ser Leu Glu Pro Leu Ala Leu Glu Gly Ser Leu Gln
                20                  25                  30

<210> SEQ ID NO 107
<211> LENGTH: 31
<212> TYPE: PRT
<213> ORGANISM: Homo spaiens

<400> SEQUENCE: 107

Glu Ala Glu Asp Leu Gln Val Gly Gln Val Glu Leu Gly Gly Pro
1               5                   10                  15

Gly Ala Gly Ser Leu Glu Pro Leu Ala Leu Glu Gly Ser Leu Glu
                20                  25                  30
```

<210> SEQ ID NO 108
<211> LENGTH: 31
<212> TYPE: PRT
<213> ORGANISM: Homo spaiens

<400> SEQUENCE: 108

Glu Ala Glu Asp Leu Glu Val Gly Glu Val Glu Leu Gly Gly Gly Pro
1               5                   10                  15

Gly Ala Gly Ser Leu Glu Pro Leu Ala Leu Glu Gly Ser Leu Gln
            20                  25                  30

<210> SEQ ID NO 109
<211> LENGTH: 31
<212> TYPE: PRT
<213> ORGANISM: Homo spaiens

<400> SEQUENCE: 109

Glu Ala Glu Asp Leu Glu Val Gly Gln Val Glu Leu Gly Gly Gly Pro
1               5                   10                  15

Gly Ala Gly Ser Leu Glu Pro Leu Ala Leu Glu Gly Ser Leu Glu
            20                  25                  30

<210> SEQ ID NO 110
<211> LENGTH: 31
<212> TYPE: PRT
<213> ORGANISM: Homo spaiens

<400> SEQUENCE: 110

Glu Ala Glu Asp Leu Gln Val Gly Glu Val Glu Leu Gly Gly Gly Pro
1               5                   10                  15

Gly Ala Gly Ser Leu Glu Pro Leu Ala Leu Glu Gly Ser Leu Glu
            20                  25                  30

<210> SEQ ID NO 111
<211> LENGTH: 31
<212> TYPE: PRT
<213> ORGANISM: Homo spaiens

<400> SEQUENCE: 111

Glu Ala Glu Asp Leu Glu Val Gly Glu Val Glu Leu Gly Gly Gly Pro
1               5                   10                  15

Gly Ala Gly Ser Leu Glu Pro Leu Ala Leu Glu Gly Ser Leu Glu
            20                  25                  30

<210> SEQ ID NO 112
<211> LENGTH: 14
<212> TYPE: PRT
<213> ORGANISM: Artificial sequence
<220> FEATURE:
<223> OTHER INFORMATION: Synthetic peptide

<400> SEQUENCE: 112

Gly Pro Gly Ala Gly Ser Leu Glu Pro Leu Ala Leu Glu Gly
1               5                   10